(12) United States Patent
Chi et al.

(10) Patent No.: US 8,497,260 B2
(45) Date of Patent: Jul. 30, 2013

(54) 2-ARYLBENZOTHIOPHENE DERIVATIVES OR PHARMACEUTICALLY ACCEPTABLE SALTS THEREOF, PREPARATION METHOD THEREOF, AND PHARMACEUTICAL COMPOSITION FOR THE DIAGNOSIS OR TREATMENT OF DEGENERATIVE BRAIN DISEASE CONTAINING THE SAME AS ACTIVE INGREDIENT

(75) Inventors: Dae Yoon Chi, Seoul (KR); Byoung Se Lee, Incheon (KR); Youjung Jung, Gyeonggi-do (KR); Uthaiwan Sirion, Chainat (TH); Yoo Jin Lim, Gyeonggi-do (KR); Yu Jin Bae, Incheon (KR); Heejun Kim, Seoul (KR); So Young Chu, Incheon (KR); Dae Hyuk Moon, Seoul (KR); Jin-Sook Ryu, Seoul (KR); Jae Seung Kim, Seoul (KR); Seung Jun Oh, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 452 days.

(21) Appl. No.: 12/579,789

(22) Filed: Oct. 15, 2009

(65) Prior Publication Data
US 2010/0261727 A1    Oct. 14, 2010

(30) Foreign Application Priority Data
Apr. 9, 2009    (KR) .......................... 10-2009-0030929

(51) Int. Cl.
A01N 43/00    (2006.01)
A61K 31/00    (2006.01)
C07F 1/00    (2006.01)

(52) U.S. Cl.
USPC .......................... 514/210.2; 514/209; 544/225

(58) Field of Classification Search
USPC .......................... 544/225; 514/210.2, 269, 209
See application file for complete search history.

(56) References Cited

U.S. PATENT DOCUMENTS

| | | | |
|---|---|---|---|
| 4,666,829 A | | 5/1987 | Glenner et al. |
| 5,231,000 A | | 7/1993 | Majocha et al. |
| 7,250,510 B2 * | | 7/2007 | Organ et al. ................ 544/225 |
| 7,547,691 B2 * | | 6/2009 | Dahnke et al. ............... 514/218 |
| 8,063,035 B2 * | | 11/2011 | Crich et al. ................. 514/210.2 |
| 2006/0106042 A1 * | | 5/2006 | Fischer et al. ............... 514/269 |
| 2007/0105833 A1 * | | 5/2007 | Ruah et al. ................. 514/210.2 |

FOREIGN PATENT DOCUMENTS

| WO | WO 89/06242 A1 | 7/1989 |
|---|---|---|
| WO | WO 92/17152 A2 | 10/1992 |
| WO | WO 93/04194 A1 | 3/1993 |

OTHER PUBLICATIONS

Aoyagi et al., Heterocycles (1992) 33(1), 257-72.*
Seggio et al.I, Cynlett (2008), (19), 2955-2960.*

* cited by examiner

Primary Examiner — Paul V. Ward
(74) Attorney, Agent, or Firm — Alston & Bird LLP

(57) ABSTRACT

2-arylbenzothiophene derivatives or pharmaceutically acceptable salts thereof, a preparation method thereof, and a pharmaceutical composition for the diagnosis or treatment of degenerative brain disease containing the same as an active ingredient. Since the 2-arylbenzothiophene derivatives of Formula 1 have a relatively high binding affinity for β-amyloid, they can be used as diagnostic reagents for diagnosing Alzheimer's disease at an early stage by non-invasive techniques when they are labeled with radioisotopes:

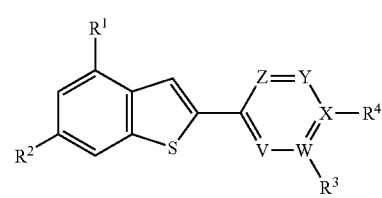

[Formula 1]

wherein $R^1$-$R^4$, V, W, X, Y and Z are as defined in the Detailed Descript of the specification. Further, when the pharmaceutical composition containing the 2-arylbenzothiophene derivative binds with a low-molecular weight β-amyloid peptide binding compound, generation of malignant high-molecular weight β-amyloid deposits is minimized. Accordingly, the pharmaceutical composition can be used as a therapeutic agent of degenerative brain disease such as Alzheimer's disease.

11 Claims, No Drawings

2-ARYLBENZOTHIOPHENE DERIVATIVES OR PHARMACEUTICALLY ACCEPTABLE SALTS THEREOF, PREPARATION METHOD THEREOF, AND PHARMACEUTICAL COMPOSITION FOR THE DIAGNOSIS OR TREATMENT OF DEGENERATIVE BRAIN DISEASE CONTAINING THE SAME AS ACTIVE INGREDIENT

CROSS-REFERENCE TO RELATED APPLICATION

This application claims the benefit under 35 U.S.C. §119 (a) of a Korean Patent Application filed in the Korean Intellectual Property Office on Apr. 9, 2009 and assigned Serial No. 10-2009-0030929, the entire disclosure of which is hereby incorporated by reference.

BACKGROUND (a) Technical Field

The present invention discloses 2-arylbenzothiophene derivatives or pharmaceutically acceptable salts thereof, a preparation method thereof, and a pharmaceutical composition for the diagnosis or treatment of degenerative brain disease, containing the same as an active ingredient.

(b) Background Art

With an increase of the aged population and an increase in the life span of human beings, the incidence of Alzheimer's disease (hereinafter, referred to simply as "AD") has been increasing. AD is one of representative degenerative neurological diseases and Dr. Alois Alzheimer first noticed characteristic signs and symptoms of AD in 1906. AD is known as one of the most common causes of dementia among older people, causing memory loss and other cognitive deficits (MaKhann et al., Neurology, 1984, 34, 939-944). Incidence of AD for prolonged periods may increase risks for complications and lead to even death. AD can strike people as young as 40-50 years of age, and the prevalence of AD increases with age, with estimates of the affected population reaching as high as 40-50% by ages 85-90. (Evans et al., The Journal of the American Medical Association, 1989, 262, 2551-2556; Katzman, Neurology, 1993, 43, 13-20).

Recently, results of research into AD are being reported by many scientists and development of pharmaceutical products for prevention and treatment of various diseases is actively under way. However, no available medication that has been developed so far can completely cure the disease once it onsets but can only slow delay the progression of the disease. Accordingly, the best way to cope with AD is to slow or delay the AD progression through early diagnosis. Since pathological changes of AD probably occur about 7 years before AD symptoms are noticeable, early diagnosis of the AD and the follow-up treatment for the early diagnosis are keenly needed.

Postmortem slices of AD patient's brain tissue exhibit the presence of amyloid plaque and neurofibrillary tangles (NFTs). The amyloid plaques are extracellular amyloid peptide deposits and the NFTs are intracellular deposits of microtubule associated tau protein. Although the issue as to which of the two types of lesions in the brain appears first has remained controversial, the presence of amyloid plaques as an early sign of AD is undoubtedly accepted by the majority of researchers. The presence of β-amyloid may cause considerable biochemical changes, leading to deposits of other proteins, thereby activating phagocytosis of microglial cells, and resulting in death of neurons and incurable loss of cognitive functions.

The initial deposition of β-amyloid probably occurs long before clinical symptoms are noticeable. The currently recommended "minimum microscopic criteria" for the diagnosis of AD is based on the number of neuritic plaques found in brain (Khachaturian, Arch. Neurol., 1985, 42, 1097-1105). Unfortunately, assessment of neuritic plaque counts must be delayed until after death. The amyloid of these neuritic plaques is a peptide composed of amino acids 39-43 called the β-amyloid that is arranged in a predominately beta-pleated sheet configuration (Kirschner et al., Proc. Natl. Acad. Sci., 1986, 83, 503-507). Specifically, β-amyloid 42 demonstrates higher neurotoxicity and much higher formation rate of amyloid plates than β-amyloid 40, which is due to its hydrophobic amino acid residues (Yoshiike, Y.; Takashima, A. Am. Soc. Biochem. Molecular Biol., 2003, 278, 23648-23655). Amino Acid Sequence for β-amyloid is as follows:

TABLE 1

| A 42 | A 40 | 1 | 2 | 3 | 4 | 5 | 6 | 7 | 8 | 9 | 10 |
|---|---|---|---|---|---|---|---|---|---|---|---|
| | | Asp | Ala | Glu | Phe | Arg | His | Asp | Ser | Gly | Tyr |
| | | 11 | 12 | 13 | 14 | 15 | 16 | 17 | 18 | 19 | 20 |
| | | Glu | Val | His | His | Gln | Lys | Leu | Val | Phe | Phe |
| | | 21 | 22 | 23 | 24 | 25 | 26 | 27 | 28 | 29 | 30 |
| | | Ala | Glu | Asp | Val | Gly | Ser | Asn | Lys | Gly | Ala |
| | | 31 | 32 | 33 | 34 | 35 | 36 | 37 | 38 | 39 | 40 |
| | | Ile | Ile | Gly | Leu | Met | Val | Gly | Gly | Val | Val |
| | | 41 | 42 | | | | | | | | |
| | | Ile | Ala | | | | | | | | |

Up to recently, there have been no antemortem probes for brain β-amyloid deposits of AD patients or patients who are suspected of having AD. Brain amyloid deposits were only analyzed by staining the brain sections after the patients died. Brain amyloid is readily demonstrated by staining brain sections with Thioflavin S of Formula I or Congo red of Formula II (Puchtler et al., J. Histochem. Cytochem., 1962, 10, 355-364). Congo red stained amyloid is characterized by a dichroic appearance, exhibiting a yellow-green polarization color. The dichroic binding is the result of the beta-pleated sheet structure of the amyloid proteins (Glenner, G. N. Eng. J. Med., 1980, 302, 1283-1292).

[Formula I]

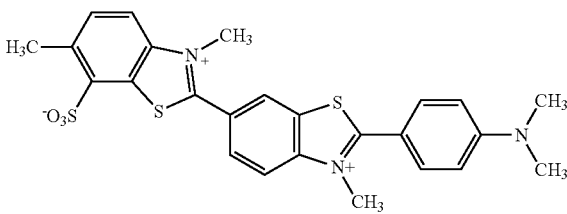

Thioflavin S

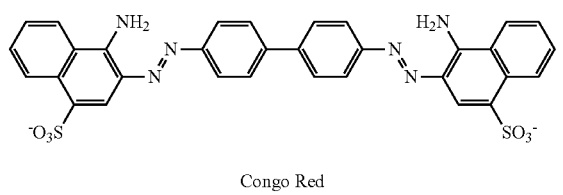

Congo Red

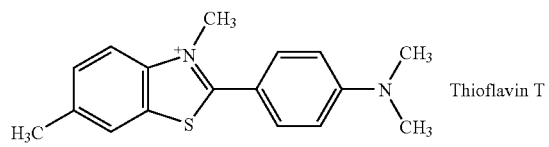

Thioflavin T

Thus far, diagnosis of AD has been achieved mostly through clinical criteria evaluation, brain biopsies and post-mortem tissue studies. Research efforts to develop methods for diagnosing Alzheimer's disease in vivo, including immunoassay methods and imaging techniques, have been attempted.

Immunoassay methods have been developed to detect the presence of neurochemical markers in AD patients and to detect an AD related amyloid protein in cerebral spinal fluid (Warner, Anal. Chem. 59: 1203A (1987); World Patent No. 92/17152 by Potter; Glenner et al., U.S. Pat. No. 4,666,829; Majocha et al., J. Nucl. Med., 1992, 33, 2184; Majocha et al., WO 89/06242; and Majocha et al., U.S. Pat. No. 5,231,000). One of major disadvantages with antibody probes is a difficulty in getting these large molecules across the blood-brain barrier (BBB). In order to gain access into the brain, using antibodies for in vivo diagnosis of AD would require marked abnormalities in the blood-brain barrier. There is no convincing functional evidence that abnormalities in the blood-brain barrier reliably exist in AD. Radiolabeled amyloid peptides have also been used to label diffuse, compact and neuritic type plaques in sections of AD brain (Edward et al., WO 93/04194). However, these peptides share all of the disadvantages of antibodies in that peptides do not normally cross the blood-brain barrier in amounts necessary for imaging.

As described above, Congo red and Thioflavin S are dyes used to stain β-amyloid deposits in postmortem brain tissues. The binding affinities and specific selectivity of Congo red and Thioflavin S imply possibilities of detecting the presence and amount of β-amyloid deposits in the amyloid in vivo. However, since these compounds have relatively large molecular weights, it is quite difficult for them to cross the blood brain barrier (BBB). In addition, sulfonate salt and quarternary ammonium salt contained in each compound make Congo red and Thioflavin S more difficult cross the blood brain barrier (BBB). Furthermore, Congo red has a diazo group, which is known to be carcinogenic, and is metabolized in the form of a free amine by intestinal bacteria, which is, however, disadvantageous, in that bioavailability is noticeably lowered in a case where a therapeutic compound is orally administered.

Thioflavin S is commonly used in the post-mortem study of amyloid deposition in AD brain where it has been shown to be one of the most sensitive techniques for demonstrating senile plaques. Vallet et al. Acta Neuropatholi., 1992, 84, 170). Thioflavin T of Formula III has been frequently used as a reagent to study the aggregation of soluble amyloid proteins into beta-sheet fibrils (LeVine Prot. Sci. 1993, 2, 404-410). Quaternary amine derivatives related to Thioflavin T have been proposed as amyloid imaging agents, although no evidence of brain uptake of these agents has been presented.

Recently, neutral derivative groups have been developed from Thioflavin T structure including an uncharged 2-arylbenzothiazole structure, and varying a variety of substituent groups led to findings that the neutral derivative groups strongly bind with β-amyloid deposits and easily cross the blood-brain barrier. In addition, other different analogs having diaryl or conjugated diaryl structures that are characteristic of the 2-arylbenzothiazole structure were developed by many researchers, who have studied detection methods and distribution of amyloid in vivo using compounds labeled with radioisotopes such as F-18, C-11, I-123, I-125 or the like, as of Formulas IV-VII. Details of each of the compounds of Formulas IV-VII, including abbreviated names, binding affinity ($K_i$) values, discoverers and documents cited (?) are listed below: Compound of Formula IV_[$^{11}$C]PIB, $K_i$=2.8 nM, Mathis, C. A., Wang, Y., Holt, D. P., Huang, G. F., Debnath, M. L., Klunk, W. E. Synthesis and evaluation of $^{11}$C-labeled 6-substituted 2-arylbenzothiazoles as amyloid imaging agents., J. Med. Chem., 2003, 46, 2740-2754; Compound of Formula V_[$^{18}$F]FDDNP, $K_i$=0.12 nM, Shoghi-Jadid, K., Small, G. W., Agdeppa, E. D., Kepe, V., Ercoli, L. M., Siddarth, P., Read, S., Satyamurthy, N., Petric, A., Huang, S. C., Barrio, J. R., Localization of neurofibrillary tangles and beta-amyloid plaques in the brains of living patients with Alzheimer disease., Am. J. Geriatr. Psychiatry, 2002, 10, 24-35; Compound of Formula VI_[$^{11}$C]SB-13, $K_i$=1.2 nM, Ono, M., Wilson, A., Nobrega, J., Westaway, D., Verhoeff, P., Zhuang, Z.-P., Kung, M.-P., Kung, H. F., $^{11}$C-Labeled Stilbene Derivatives as Ab-aggregate-specific PET Imaging Agents for Alzheimer's Disease, Nucl. Med. Biol., 2003, 30, 565-571; Compound of Formula VII_[$^{123}$I/$^{125}$I]IMPY, $K_i$=15.0 nM, Kung, M. P., Hou, C., Zhuang, Z. P., Zhang, B., Skovronsky, D., Trojanowski, J. Q., Lee, V. M., Kung, H. F., IMPY: an improved thioflavin-T derivative for in vivo labeling of beta-amyloid plaques., Brain Res., 2002, 956, 202-210).

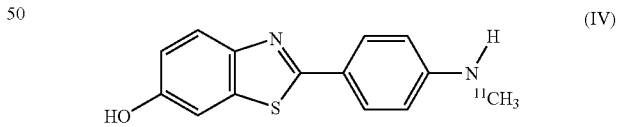

[$^{11}$C] Pittsburgh Compound B([$^{11}$C]PIB)

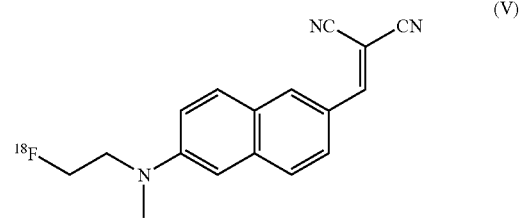

[$^{18}$F]FDDNP

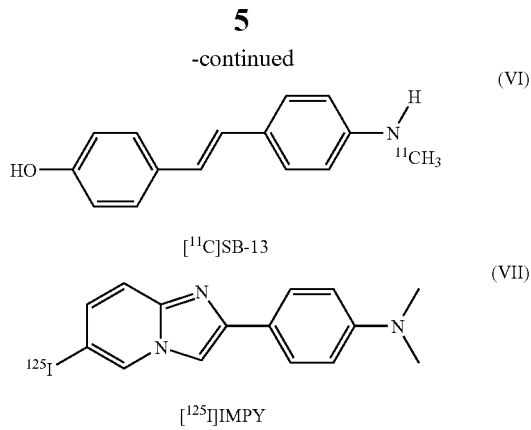

[¹¹C]SB-13

[¹²⁵I]IMPY

The compounds of Formulas IV, V, VI and VII are provided just as some representative compounds of a variety of compounds researched, which were developed for the diagnosis of the onset and progression of AD. The compounds of Formulas IV, V, VI and VII are radioactive tracers labeled with radioisotopes, allowing detection of β-amyloid deposits in vivo by positron emission tomorgraphy (PET) and single-photon emission computed tomography (SPECT).

In order to effectively detect and diagnose β-amyloid deposits in living patients, the following criteria must be satisfied: a high binding affinity for β-amyloid deposits; high selectivity to biological substance analogs such as neurofibrillary tangle (NFT); use of the minimum dosage concentration without toxicity, or the normally amount necessary for tomography using radioisotopes in crossing the blood-brain barrier to finally reach target β-amyloid deposits. In conclusion, it is important to obtain AD amyloid deposits in brain, which can be definitely distinguished from AD brain from normal brain.

Currently, existing methods for quantifying antemortem probes for brain amyloid deposits have been achieved mostly by diagnosis through doctors' clinical consultation and monitoring the effectiveness of therapies targeted at preventing β-amyloid deposits. However, it has turned out that the existing methods are not so accurate and the therapies associated with β-amyloid deposits are pointless once clinical signs are detected. Therefore, it remains of utmost importance to develop safe and specific methods for diagnosing AD by imaging amyloid in brain in vivo. In addition, these methods are also important for research into AD, for which there are no known preventive or therapeutic means available yet, and for diagnosis patients of Down's syndrome featured by amyloid-containing neuritic plaques and persons homozygous for the apolipoprotein E4 allele who are very likely to develop AD.

Even though various attempts have been made to diagnose AD in vivo, there are no antemortem probes for brain amyloid yet, and thus far no in vivo methods for AD diagnosis have been demonstrated to meet these criteria.

Although additional radioligand binding sites have been identified, the currently known status for radioligand binding is that there are three different radioligand binding sites developing in each β-amyloid deposits, including binding sites of Congo red, Thioflavin T and FDDNP (Cai, Innis, and Pike, Cur. Med. Chem., 2007, 14, 19-52).

Recently, laboratory results have been reported, suggesting that Congo red inhibits β-amyloid induced neurotoxicity and cell degeneration in vitro. (Burgevin et al., NeuroReport, 1994, 5, 2429; Lorenzo and Yankner, Proc. Natl. Acad. Sci., 1994, 91, 12243-12247; Pollack et al., Neuroscience Letters, 1995, 184, 113; Pollack et al., Neuroscience Letters, 1995, 197, 211). The mechanism appears to involve both inhibition of fibril formation and prevention of the neurotoxic properties of formed fibrils (Lorenzo and Yankner, Proc. Natl. Acad. Sci., 1994, 91, 12243-12247). Congo red is also known to protect pancreatic cells from toxic amylin, which is similar to β-amyloid plaques or fibrils of the pancreas of patients' with Type II diabetes (Lorenzo and Yankner, Proc. Natl. Acad. Sci., 1994, 91, 12243-12247). These findings imply that a compound that specifically binds to β-amyloid deposits and inhibits β-amyloid plaque formation can be a composition candidate of a single therapeutic agent or a combination of therapeutic agents for preventing or treating AD associated with β-amyloid deposits.

Under the circumstances, the present inventors have researched preparation methods of novel compounds for diagnosis and treatment of AD and found that when the pharmaceutical composition containing the 2-arylbenzothiophene derivative binds with a low-molecular weight β-amyloid peptide binding compound, generation of malignant high-molecular weight β-amyloid deposits is suppressed. Accordingly, the pharmaceutical composition can be used as a therapeutic agent of a degenerative brain disease such as Alzheimer's disease. Based on these findings, the inventors of the present invention have completed the invention.

SUMMARY OF THE DISCLOSURE

To solve the above-described problems, it is an object of the present invention is to provide 2-aryl benzothiophene derivatives or pharmaceutically acceptable salts thereof.

It is another object of the present invention is to provide a preparation method of the 2-aryl benzothiophene derivatives.

It is still another object of the present invention is to provide precursors of the 2-aryl benzothiophene derivatives.

It is a further object of the present invention to provide a preparation method of the precursors of the 2-aryl benzothiophene derivatives.

It is yet another object of the present invention to provide a method of labeling the 2-aryl benzothiophene derivatives with a radioisotope.

It is a still further object of the present invention to provide a pharmaceutical composition for the diagnosis or treatment of degenerative brain disease containing the same as an active ingredient.

To accomplish the above and other objects of the present invention, the present invention provides a 2-aryl benzothiophene derivative of Formula 1, or a pharmaceutically acceptable salt thereof:

[Formula 1]

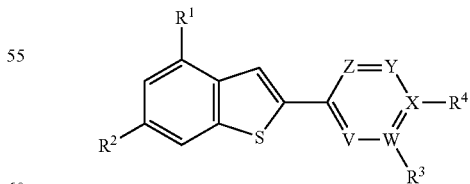

wherein, $R^1$-$R^4$ are independently or optionally hydrogen, halogen, hydroxy, $C_1$-$C_4$ linear or branched alkoxy which is unsubstituted or substituted with hydroxy or fluorine, nitro, amino, $C_1$-$C_4$ linear or branched alkylamino which is unsubstituted or substituted with fluorine, or dimethylamino;

and V, W, X, Y and Z are independently carbon or nitrogen, where fluorine is in the form of $^{18}$F or $^{19}$F.

The present invention also provides a preparation method of the 2-aryl benzothiophene derivative.

The present invention also provides a precursor of the 2-aryl benzothiophene derivative.

The present invention also provides a preparation method of the precursor of the 2-arylbenzothiophene derivative.

The present invention also provides a method of labeling the 2-aryl benzothiophene derivative with a radioisotope.

The present invention also provides a pharmaceutical composition for the diagnosis or treatment of degenerative brain disease, the pharmaceutical composition containing the same as an active ingredient.

Since the derivatives according to the present invention have a relatively high binding affinity for β-amyloid, they can be used as diagnostic reagents for diagnosing AD at an early stage by non-invasive techniques when they are labeled with radioisotopes. Further, when the pharmaceutical composition containing the derivative is bound with a low-molecular weight β-amyloid peptide binding compound, since formation of malignant high-molecular weight β-amyloid deposits is suppressed, the pharmaceutical composition can be useful as a therapeutic agent of a degenerative brain disease such as AD.

DETAILED DESCRIPTION

Reference will now be made in detail to the preferred embodiments of the present invention.

In an aspect, the present invention discloses a novel 2-aryl-benzothiophene derivative of Formula 1 or a pharmaceutically acceptable salt thereof:

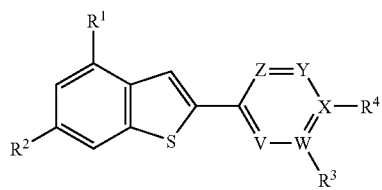

[Formula 1]

wherein $R^1$-$R^4$ are independently or optionally hydrogen, halogen, hydroxy, $C_1$-$C_4$ linear or branched alkoxy which is unsubstituted or substituted with hydroxy or fluorine, nitro, amino, $C_1$-$C_4$ linear or branched alkylamino which is unsubstituted or substituted with fluorine, or dimethylamino, and V, W, X, Y and Z are independently carbon or nitrogen, where fluorine is in the form of $^{18}$F or $^{19}$F.

Preferably, $R^1$ and $R^2$ are independently or optionally hydrogen, hydroxy, $C_1$-$C_4$ linear or branched alkoxy which is unsubstituted or substituted with hydroxy or fluorine, nitro, amino, or $C_1$-$C_4$ linear or branched alkylamino; $R^3$ and $R^4$ are independently or optionally hydrogen, halogen, hydroxy, $C_1$-$C_4$ linear or branched alkoxy which is unsubstituted or substituted with hydroxy or fluorine, nitro, amino, $C_1$-$C_4$ linear or branched alkylamino which is unsubstituted or substituted with hydroxy or fluorine, or dimethylamino; and V, W, X, Y and Z are independently carbon or nitrogen, where fluorine is in the form of $^{18}$F or $^{19}$F.

More preferably, $R^1$ and $R^2$ are independently or optionally hydrogen, hydroxyl, methoxy, ethoxy, fluoroethoxy, fluoropropoxy, nitro, or amino or methylamino; $R^3$ and $R^4$ are independently or optionally hydrogen, fluorine, chlorine, hydroxy, methoxy, ethoxy, fluoroethoxy, fluoropropoxy, nitro, amino, methylamino, or fluoroethylamino or fluoropropylamino; and V, W, X, Y and Z are independently carbon or nitrogen, where fluorine is in the form of $^{18}$F or $^{19}$F.

Preferable examples of the novel 2-arylbenzothiophene derivative of Formula 1 include, but are not limited to, (1) 2-(4-nitrophenyl)-4-methoxybenzothiophene;
(2) 2-(3-nitrophenyl)-6-methoxybenzothiophene;
(3) 2-(4-nitrophenyl)-6-methoxybenzothiophene;
(4) 2-(4-nitrophenyl)-6-hydroxybenzothiophene;
(5) 2-(4-nitrophenyl)-6-(2-fluoroethoxy)benzothiophene;
(6) 2-(4-nitrophenyl)-6-(3-fluoropropoxy)benzothiophene;
(7) 2-(4-aminophenyl)-4-methoxybenzothiophene;
(8) 2-(4-aminophenyl)-6-methoxybenzothiophene;
(9) 2-(4-aminophenyl)-6-(2-fluoroethoxy)benzothiophene;
(10) 2-(4-aminophenyl)-6-(3-fluoropropoxy)benzothiophene;
(11) 2-[4-(N-monomethylamino)phenyl]-6-methoxybenzothiophene;
(12) 2-[4-(N-monomethylamino)phenyl]-6-(2-fluoroethoxy)benzothiophene;
(13) 2-[4-(N-monomethylamino)phenyl]-6-(3-fluoropropoxy)benzothiophene;
(14) 2-[4-(N,N-dimethylamino)phenyl]-4-methoxybenzothiophene;
(15) 2-[4-(N,N-dimethylamino)phenyl]-6-methoxybenzothiophene;
(16) 2-[4-(N,N-dimethylamino)phenyl]-6-(2-fluoroethoxy)benzothiophene;
(17) 2-[4-(N,N-dimethylamino)phenyl]-6-(3-fluoropropoxy)benzothiophene;
(18) 2-[2-(2-fluoroethoxy)pyridine-5-yl]-6-methoxybenzothiophene;
(19) 2-[2-(3-fluoropropoxy)pyridine-5-yl]-6-methoxybenzothiophene;
(20) 2-(2-methoxypyridine-5-yl)-6-(2-fluoroethoxy)benzothiophene;
(21) 2-(2-aminopyridine-5-yl)-6-(2-fluoroethoxy)benzothiophene;
(22) 2-[2-(N-monomethylamino)phenyl]-6-(2-fluoroethoxy)benzothiophene;
(23) 2-[2-(N,N-dimethylamino)phenyl]-6-(2-fluoroethoxy)benzothiophene;
(24) 2-(2-aminopyridine-5-yl)-6-(3-fluoropropoxy)benzothiophene;
(25) 2-[2-(N-monomethylamino)pyridine-5-yl]-6-(3-fluoropropoxy)benzothiophene;
(26) 2-[2-(N,N-dimethylamino)pyridine-5-yl]-6-(3-fluoropropoxy)benzothiophene;
(27) 2-[2-(2-fluoroethoxy)pyridine-4-yl]-6-methoxybenzothiophene;
(28) 2-[2-(3-fluoropropoxy)pyridine-4-yl]-6-methoxybenzothiophene;
(29) 2-(2-methoxypyridine-4-yl)-6-(2-fluoroethoxy)benzothiophene;
(30) 2-(2-methoxypyridine-4-yl)-6-(3-fluoropropoxy)benzothiophene;
(31) 2-[2-(2-fluoroethoxy)pyrimidine-4-yl]-6-methoxybenzothiophene;
(32) 2-[2-(3-fluoropropoxy)pyrimidine-4-yl]-6-methoxybenzothiophene;
(33) 2-[2-(N-(2-fluoroethyl)amino)pyrimidine-4-yl]-6-methoxybenzothiophene;
(34) 2-(2-methoxypyrimidine-4-yl)-6-(2-fluoroethoxy)benzothiophene;
(35) 2-[2-(N-monomethylamino)pyrimidine-4-yl]-6-(2-fluoroethoxy)benzothiophene;

(36) 2-[2-(N,N-dimethylamino)pyrimidine-4-yl]-6-(2-fluoroethoxy)benzothiophene;
(37) 2-(2-methoxypyrimidine-4-yl)-6-(3-fluoropropoxy)benzothiophene;
(38) 2-[2-(N-monomethylamino)pyrimidine-4-yl]-6-(3-fluoropropoxy)benzothiophene;
(39) 2-[2-(N,N-dimethylamino)pyrimidine-4-yl]-6-(3-fluoropropoxy)benzothiophene;
(40) 2-[4-(2-fluoroethoxy)pyrimidine-2-yl]-6-methoxybenzothiophene;
(41) 2-[4-(N-monomethylamino)pyrimidine-2-yl]-6-(2-fluoroethoxy)benzothiophene;
(42) 2-[4-(N,N-dimethylamino)pyrimidine-2-yl]-6-(2-fluoroethoxy)benzothiophene;
(43) 2-[4-(N-monomethylamino)pyrimidine-2-yl]-6-(3-fluoropropoxy)benzothiophene;
(44) 2-[3-(2-fluoroethoxy)pyridazine-6-yl]-6-methoxybenzothiophene;
(45) 2-[3-(3-fluoropropoxy)pyridazine-6-yl]-6-methoxybenzothiophene;
(46) 2-(3-methoxypyridazine-6-yl)-6-(2-fluoroethoxy)benzothiophene;
(47) 2-(3-aminopyridazine-6)-6-(2-fluoroethoxy)benzothiophene;
(48) 2-[3-(N-monomethylamino)pyridazine-6-yl]-6-(2-fluoroethoxy)benzothiophene;
(49) 2-[3-(N,N-dimethylamino)pyridazine-6-yl]-6-(2-fluoroethoxy)benzothiophene;
(50) 2-(3-methoxypyridazine-6-yl)-6-(3-fluoropropoxy)benzothiophene;
(51) 2-(3-aminopyridazine-6-yl)-6-(3-fluoropropoxy)benzothiophene;
(52) 2-[3-(N-monomethylamino)pyridazine-6-yl]-6-(3-fluoropropoxy)benzothiophene;
(53) 2-[3-(N,N-dimethylamino)pyridazine-6-yl]-6-(3-fluoropropoxy)benzothiophene;
(54) 2-[2-(2-fluoroethoxy)pyrazine-6-yl]-6-methoxybenzothiophene; and
(55) 2-[2-(3-fluoropropoxy)pyrazine-6-yl]-6-methoxybenzothiophene.

Structures of formulas of the compounds according to the present invention are given below:

TABLE 2

| Comp'd | Structure |
| --- | --- |
| 1 | 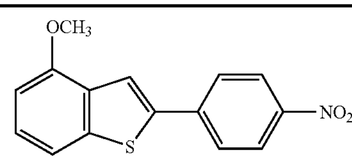 |
| 2 | 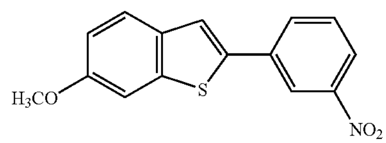 [SMILES: COc1ccc2cc(-c3cccc([N+](=O)[O-])c3)sc2c1] |
| 3 | 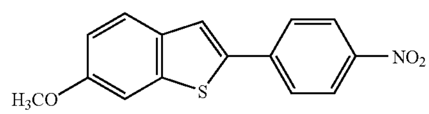 |
| 4 | 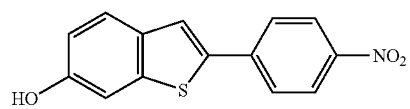 [SMILES: O=[N+]([O-])c1ccc(-c2cc3ccc(O)cc3s2)cc1] |
| 5 | 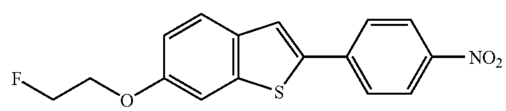 [SMILES: O=[N+]([O-])c1ccc(-c2cc3ccc(OCCF)cc3s2)cc1] |
| 6 | 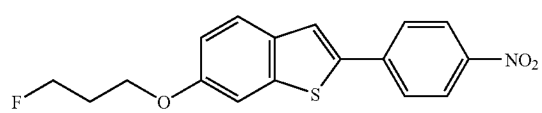 |
| 7 | 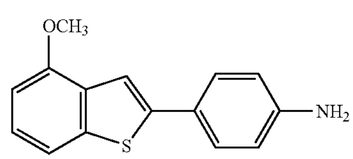 |
| 8 | 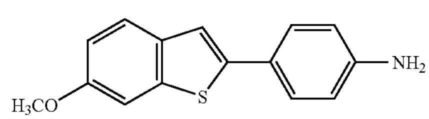 |

TABLE 2-continued

| Comp'd | Structure |
|---|---|
| 9 | 6-(2-fluoroethoxy)benzothiophen-2-yl linked to 4-aminophenyl |
| 10 | 6-(3-fluoropropoxy)benzothiophen-2-yl linked to 4-aminophenyl |
| 11 | 6-methoxybenzothiophen-2-yl linked to 4-(methylamino)phenyl |
| 12 | 6-(2-fluoroethoxy)benzothiophen-2-yl linked to 4-(methylamino)phenyl |
| 13 | 6-(3-fluoropropoxy)benzothiophen-2-yl linked to 4-(methylamino)phenyl |
| 14 | 4-methoxybenzothiophen-2-yl linked to 4-(dimethylamino)phenyl |
| 15 | 6-methoxybenzothiophen-2-yl linked to 4-(dimethylamino)phenyl |
| 16 | 6-(2-fluoroethoxy)benzothiophen-2-yl linked to 4-(dimethylamino)phenyl |
| 17 | 6-(3-fluoropropoxy)benzothiophen-2-yl linked to 4-(dimethylamino)phenyl |
| 18 | 6-methoxybenzothiophen-2-yl linked to 6-(2-fluoroethoxy)pyridin-3-yl |
| 19 | 6-methoxybenzothiophen-2-yl linked to 6-(3-fluoropropoxy)pyridin-3-yl |
| 20 | 6-(2-fluoroethoxy)benzothiophen-2-yl linked to 6-methoxypyridin-3-yl |
| 21 | 6-(2-fluoroethoxy)benzothiophen-2-yl linked to 6-aminopyridin-3-yl |

TABLE 2-continued

| Comp'd | Structure |
|---|---|
| 22 | 6-(2-fluoroethoxy)benzothiophen-2-yl linked to 6-(methylamino)pyridin-3-yl |
| 23 | 6-(2-fluoroethoxy)benzothiophen-2-yl linked to 6-(dimethylamino)pyridin-3-yl |
| 24 | 6-(3-fluoropropoxy)benzothiophen-2-yl linked to 6-aminopyridin-3-yl |
| 25 | 6-(3-fluoropropoxy)benzothiophen-2-yl linked to 6-(methylamino)pyridin-3-yl |
| 26 | 6-(3-fluoropropoxy)benzothiophen-2-yl linked to 6-(dimethylamino)pyridin-3-yl |
| 27 | 6-methoxybenzothiophen-2-yl linked to 2-(2-fluoroethoxy)pyridin-4-yl |
| 28 | 6-methoxybenzothiophen-2-yl linked to 2-(3-fluoropropoxy)pyridin-4-yl |
| 29 | 6-(2-fluoroethoxy)benzothiophen-2-yl linked to 2-methoxypyridin-4-yl |
| 30 | 6-(3-fluoropropoxy)benzothiophen-2-yl linked to 6-methoxypyridin-3-yl |
| 31 | 6-methoxybenzothiophen-2-yl linked to 2-(2-fluoroethoxy)pyrimidin-4-yl |
| 32 | 6-methoxybenzothiophen-2-yl linked to 2-(3-fluoropropoxy)pyrimidin-4-yl |

TABLE 2-continued
| Comp'd | Structure |
|---|---|
| 33 | 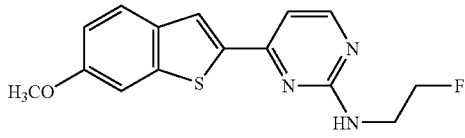 |
| 34 | 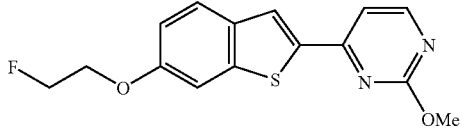 [SMILES: COc1nccc(-c2cc3ccc(OCCF)cc3s2)n1] |
| 35 | 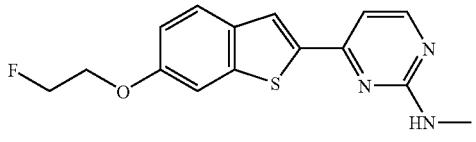 |
| 36 | 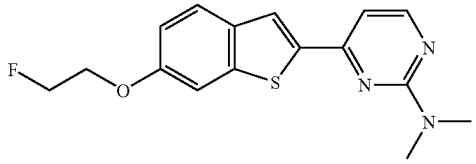 [SMILES: CN(C)c1nccc(-c2cc3ccc(OCCF)cc3s2)n1] |
| 37 | 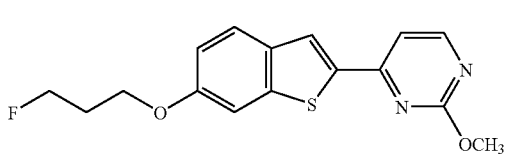 |
| 38 | 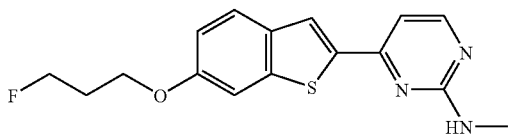 [SMILES: CNc1nccc(-c2cc3ccc(OCCCF)cc3s2)n1] |
| 39 | 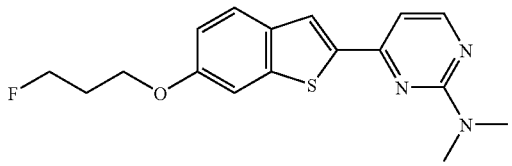 [SMILES: CN(C)c1nccc(-c2cc3ccc(OCCCF)cc3s2)n1] |
| 40 | 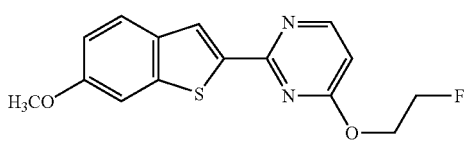 [SMILES: COc1ccc2cc(-c3nccc(OCCF)n3)sc2c1] |
| 41 | 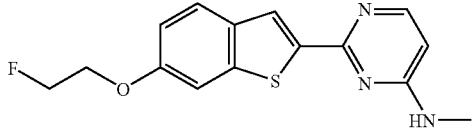 |
| 42 | 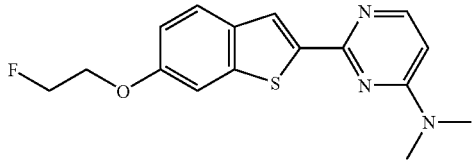 |

TABLE 2-continued
| Comp'd | Structure |
|---|---|
| 43 | 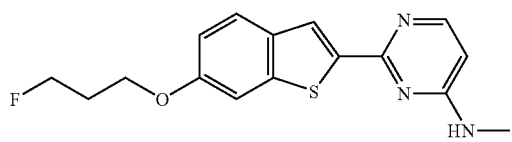 |
| 44 | 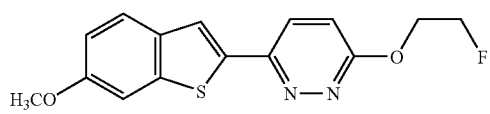 [SMILES: COc1ccc2cc(-c3ccc(OCCF)nn3)sc2c1] |
| 45 | 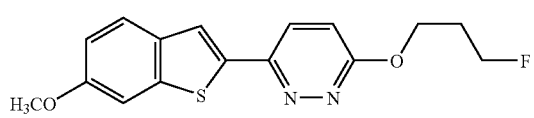 [SMILES: COc1ccc2cc(-c3ccc(OCCCF)nn3)sc2c1] |
| 46 | 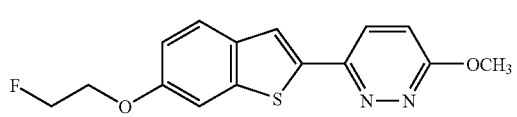 [SMILES: COc1ccc(-c2cc3ccc(OCCF)cc3s2)nn1] |
| 47 | 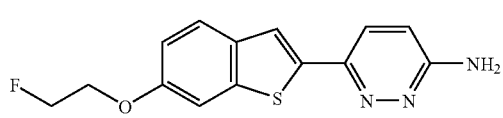 [SMILES: Nc1ccc(-c2cc3ccc(OCCF)cc3s2)nn1] |
| 48 | 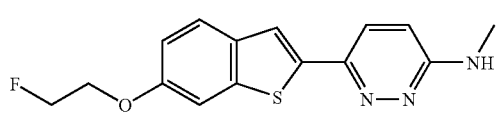 |
| 49 | 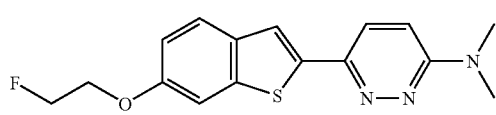 |
| 50 | 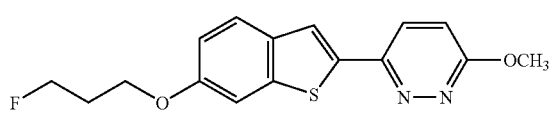 |
| 51 | 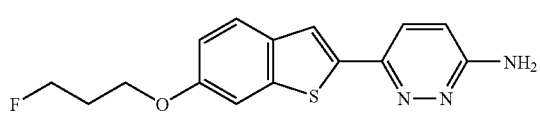 [SMILES: Nc1ccc(-c2cc3ccc(OCCCF)cc3s2)nn1] |
| 52 | 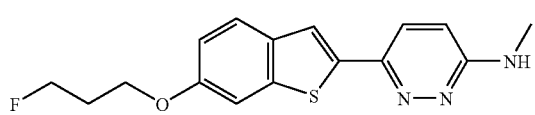 |
| 53 | 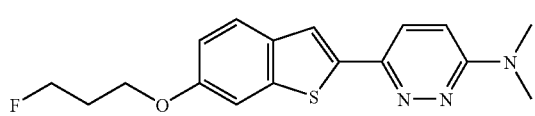 |
| 54 | 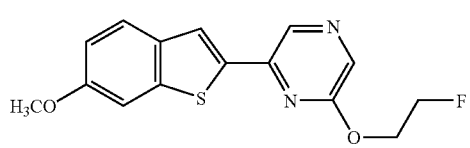 |

TABLE 2-continued

| Comp'd | Structure |
|---|---|
| 55 | 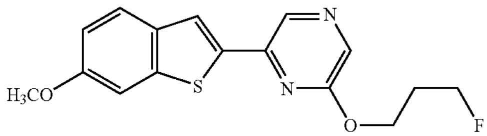 [SMILES: COc1ccc2cc(-c3cncc(OCCCF)n3)sc2c1] |

The novel aryl derivative of Formula 1 according to the present invention can be used in the form of pharmaceutically acceptable salts. Examples of useful salts include prepared by various organic acids or inorganic acids which are pharmaceutically or physiologically acceptable acid-addition salts. Examples of suitable organic acids include carboxylic acid, phosphonic acid, sulphonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, salicylic acid, phthalic acid, phenylacetic acid, benzenesulphonic acid, 2-naphthalene sulphonic acid, methylsulphuric acid, ethylsulphuric acid, dodecylsulphuric acid, and so on. Examples of suitable inorganic acids include hydrochloric acid, sulphuric acid, and phosphoric acid.

The 2-aryl derivative of Formula 1 according to the present invention may comprise not only pharmaceutically acceptable salts but also all salts, hydrates and solvates that can be prepared by generally known methods.

In addition, the present invention may provide a preparation method of the 2-aryl benzothiophene derivative of Formula 1.

In detail, the preparation method of the 2-aryl benzothiophene derivative according to the present invention may include, (1) reacting a benzothiophene derivative of Formula 3 with a boron compound $(iPrO)_3B$ in an organic solvent and catalyst to obtain a compound of Formula 4, as given in the Reaction Scheme 1; and (2) reacting the compound of Formula 4 with aryl halide in an organic solvent in the presence of catalyst to obtain the 2-arylbenzothiophene derivative according to claim 1:

[Reaction Scheme 1]

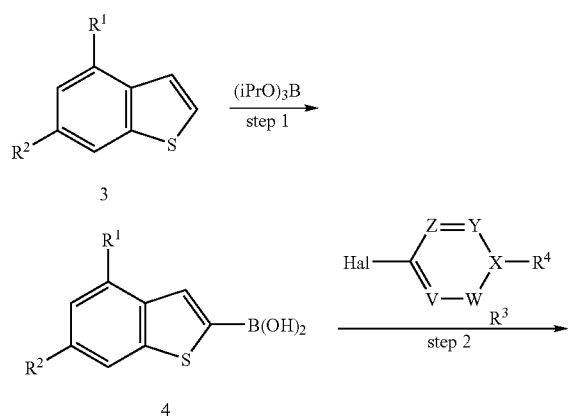

wherein $R^1$-$R^4$, V, W, X, Y and Z are the same as defined above for the Formula 1, and 'Hal' denotes a halogen element.

Hereinafter, the preparation method of the 2-aryl benzothiophene derivative according to present invention will be described in greater detail.

In the preparation method according to present invention, Step 1 is a process of reacting a benzothiophene derivative of Formula 3 with a boron compound $(iPrO)_3B$ in an organic solvent to obtain a compound of Formula 4. Here, tetrahydrofuran, diethyl ether, diisopropyl ether, t-butyl methyl ether, etc., can be used as the organic solvent, and tetrahydrofuran is preferred. First, the benzothiophene derivative of Formula 3 is introduced to the reaction using an n-butyl lithium reagent dissolved in hexane as a reaction starting material in an organic solvent under a nitrogen atmosphere. In this case, since the reaction is carried out explosive, it is necessary to cool the resultant solution, preferably to a temperature in a range of −70 to −80° C. To the cooled solution is slowly added n-butyl lithium, followed by stirring for about one hour. After the reaction is complete, the reaction temperature is raised to room temperature, triisopropylborate $((iPrO)_3B)$ is added to the reaction mixture, and the mixture is stirred for about 0.5 to 3 hours. To the mixture, 2N hydrochloric acid is added for completing the reaction, thereby obtaining the compound of Formula 4.

In the preparation method according to present invention, Step 2 is a process of reacting the compound of Formula 4 with aryl halide in an organic solvent in the presence of catalyst to obtain the 2-arylbenzothiophene derivative obtained in Step 1. 1,2-Dimethoxyethane, tetrahydropyran, isopropanol, benzene, dioxane, etc., can be used as the organic solvent, and 1,2-dimethoxyethane is preferred. In addition, palladium tetrakis catalyst $(Pd(PPh_3)_4)$ or palladium acetate $(Pd(OAc)_2)$ can be used as the catalyst. For example, arylhalide is added to 0.02 to 0.05 equivalents of $Pd(PPh_3)_4$ dissolved in a 1,2-dimethoxyethane solution and stirred at room temperature for about 10 minutes. The compound of Formula 4 dissolved in a minimum methanol solvent and an aqueous solution of 2.0 M sodium carbonate are added to the resultant mixture. The mixed solution is heated at a temperature higher than a boiling point of the organic solvent to reflux for about 6-12 hours to obtain the 2-arylbenzothiophene derivative of Formula 1.

The preparation method may further include additional substitutions to give other substituents to the 2-arylbenzothiophene derivative. The additional substitutions may be performed by conventional substitution reactions.

Further, the present invention provides a precursor of Formula 2 for labeling the 2-arylbenzothiophene derivative of Formula 1 or the pharmaceutically acceptable salt thereof with $^{18}$F:

[Formula 2]

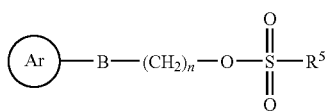

wherein

is the 2-arylbenzothiophene derivative of Formula 1 according to claim 1,

B is —NH— or —O—,

R$^5$ is methyl, trifluoromethyl, p-toluenyl, or p-nitrophenyl, and n is 2 or 3.

Preferred examples of the precursor of Formula 2 for labeling the 2-arylbenzothiophene derivative of Formula 1 or the pharmaceutically acceptable salt thereof with $^{18}$F are given below:

TABLE 3

| Comp'd | Structure |
|---|---|
| 56 | 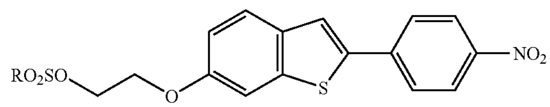 |
| 57 | 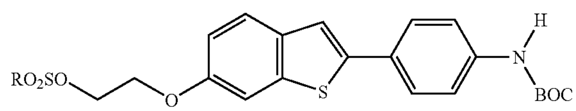 |
| 58 | 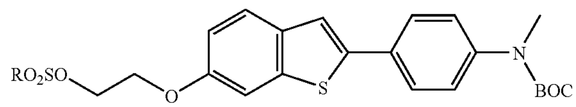 |
| 59 | 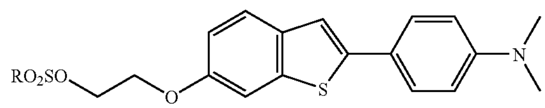 |
| 60 | 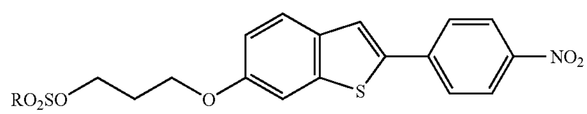 |
| 61 | 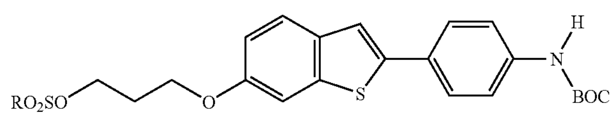 |
| 62 | 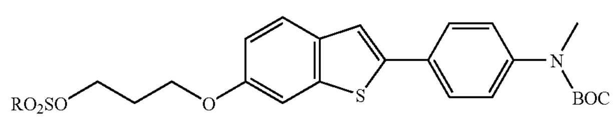 |
| 63 | 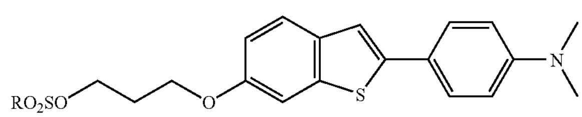 |
| 64 | 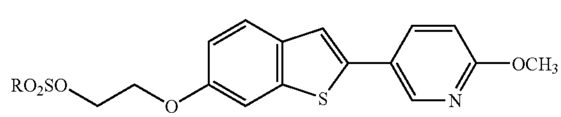 |
| 65 | 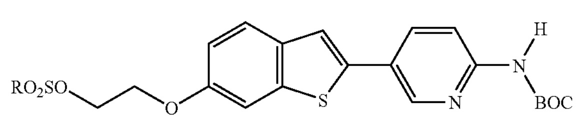 |

TABLE 3-continued

| Comp'd | Structure |
|---|---|
| 66 | RO₂SO-(CH₂)₂-O-[benzothiophene]-2-yl-[pyridin-5-yl]-N(CH₃)(BOC) |
| 67 | RO₂SO-(CH₂)₂-O-[benzothiophene]-2-yl-[pyridin-5-yl]-N(CH₃)₂ |
| 68 | RO₂SO-(CH₂)₃-O-[benzothiophene]-2-yl-[pyridin-5-yl]-NH-BOC |
| 69 | RO₂SO-(CH₂)₃-O-[benzothiophene]-2-yl-[pyrimidin-5-yl]-N(CH₃)(BOC) |
| 70 | RO₂SO-(CH₂)₃-O-[benzothiophene]-2-yl-[pyridin-5-yl]-N(CH₃)₂ |
| 71 | RO₂SO-(CH₂)₂-O-[benzothiophene]-2-yl-[pyridin-4-yl]-2-OCH₃ |
| 72 | RO₂SO-(CH₂)₃-O-[benzothiophene]-2-yl-[pyridin-4-yl]-2-OCH₃ |
| 73 | RO₂SO-(CH₂)₂-O-[benzothiophene]-2-yl-[pyrimidin-4-yl]-2-OCH₃ |
| 74 | RO₂SO-(CH₂)₂-O-[benzothiophene]-2-yl-[pyrimidin-4-yl]-2-N(CH₃)(BOC) |
| 75 | RO₂SO-(CH₂)₂-O-[benzothiophene]-2-yl-[pyrimidin-4-yl]-2-N(CH₃)₂ |
| 76 | RO₂SO-(CH₂)₃-O-[benzothiophene]-2-yl-[pyrimidin-4-yl]-2-OCH₃ |

TABLE 3-continued
| Comp'd | Structure |
|---|---|
| 77 | 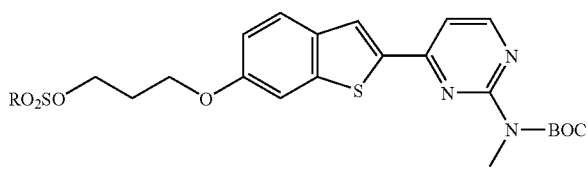 |
| 78 | 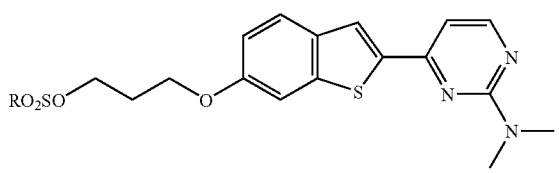 |
| 79 | 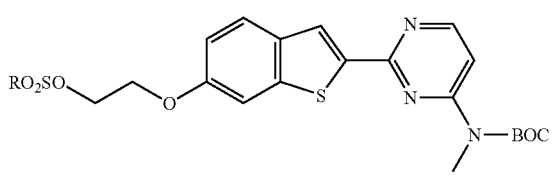 |
| 80 | 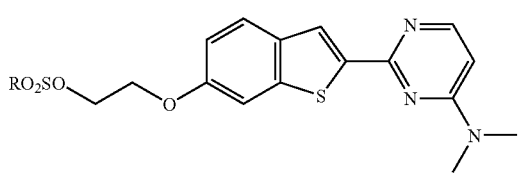 |
| 81 | 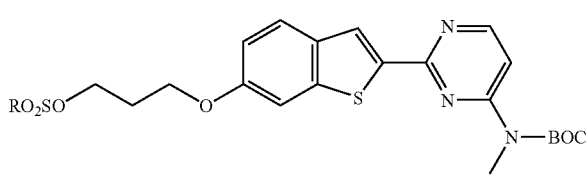 |
| 82 | 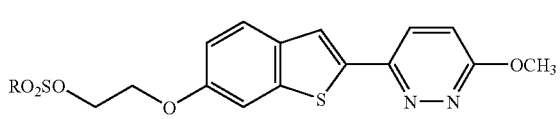 |
| 83 | 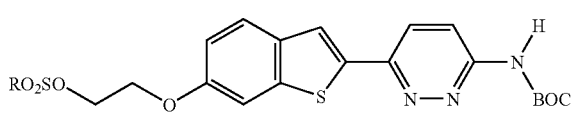 |
| 84 | 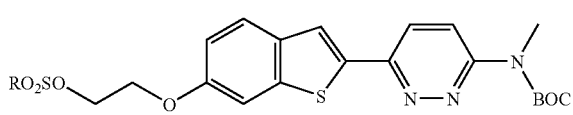 |
| 85 | 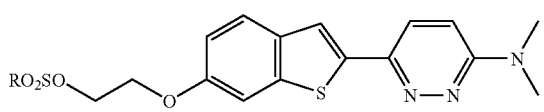 |
| 86 | 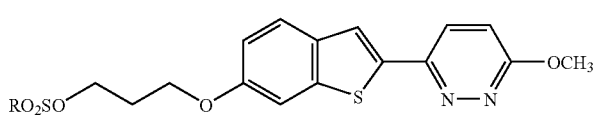 |
| 87 | 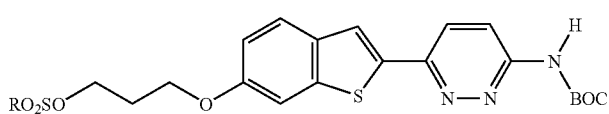 |

TABLE 3-continued

| Comp'd | Structure |
|---|---|
| 88 | 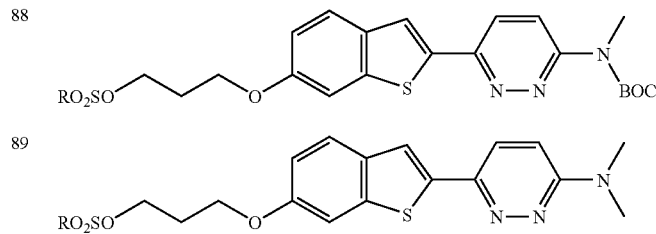 |
| 89 | 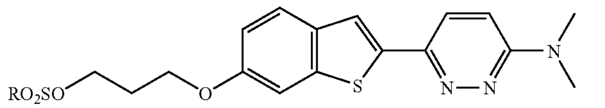 |

Further, the present invention also provides a preparation method of a precursor of Formula 2 for labeling the 2-arylbenzothiophene derivative of Formula 1 with $^{18}$F, the preparation method including reacting a 2-arylbenzothiophene derivative of Formula 6 with methane sulfonyl chloride or anhydrous methanesulfonate in an organic solvent and a base to obtain the precursor of the 2-arylbenzothiophene derivative, as given in the following Reaction Scheme 2:

[Reaction Scheme 2]

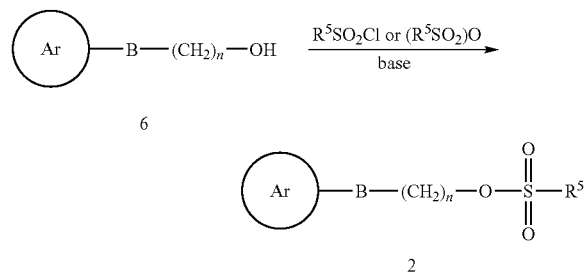

wherein

,

B, R$^5$ and n are the same as defined in claim 2 for the Formula 2.

Here, examples of the useful base may be selected from the group consisting of triethylamine, diisopropylamine, pyridine, 2,6-lutidine, 2,6-di-t-butylpyridine and 4-N,N-dimethylaminopyridine. The reaction is preferably carried out in a solvent of dichloromethane or pyridine at a temperature in a range of −10-0° C. for about 0.5-3 hours.

The preparation method of the precursor will now be described in detail.

When R$^5$ is methyl, the 2-arylbenzothiophene derivative of Formula 6 is dissolved in a dichloromethane solvent and methanesulfonyl chloride (or anhydrous methanesulfonate is added thereto. Thereafter, to the mixture solution is slowly added dropwise of triethylamine at 0° C., and stirred at the same temperature for about 30 minutes. The reaction is terminated by adding water to the resulting product to isolate an organic layer while extracting an organic compound in water using dichloromethane, giving a target product by column chromatography.

When R$^5$ is anhydrous trifluoromethanesulfonate, the 2-arylbenzothiophene derivative of Formula 6 is dissolved in a dichloromethane solvent and methanesulfonyl chloride (or anhydrous methanesulfonate is added thereto. Thereafter, to the mixture solution is slowly added dropwise of 2,6-rutidine or 2,6-di-t-butylpyridinen at −10° C., and stirred at the same temperature for about 30 minutes. The reaction is terminated by adding water to the resulting product to isolate an organic layer while repeatedly extracting an organic compound in water several times using dichloromethane. The isolated organic layer is subjected to rapid column chromatography and evaporated under reduced pressure, thereby obtaining a target product.

When R$^5$ is p-toluenyl, the 2-arylbenzothiophene derivative of Formula 6 is dissolved in a pyridine solvent. Here, 4-N,N-dimethylaminopyridine may be further added. p-toluenesulfonyl chloride is slowly added at 0° C. to the resulting product and stirred at the same temperature for about one hour. The reaction is terminated by adding to the reaction mixture. A resultant organic compound is extracted with ethyl acetate, washed with ammonium chloride and dried with sodium sulfate to remove water, followed by subjecting to column chromatography, thereby obtaining a target product.

When R$^5$ is p-nitrophenyl, the 2-arylbenzothiophene derivative of Formula 6 is dissolved in a pyridine solvent. Here, 4-N,N-dimethylaminopyridine may further be added. p-nitrobenzenesulfonyl chloride is slowly added at 0° C. to the resulting product and stirred at the same temperature for about one hour. The reaction is terminated by adding to the reaction mixture. A resultant organic compound is extracted with ethyl acetate, washed with ammonium chloride and dried with sodium sulfate to remove water, followed by subjecting to column chromatography, thereby obtaining a target product.

Further, the present invention provides a $^{18}$F labeling method including reacting a precursor of Formula 2 for labeling 2-arylbenzothiophene derivative with $^{18}$F to obtain a $^{18}$F labeled compound of Formula 7, as given in the following Reaction Scheme 3:

[Reaction Scheme 3]

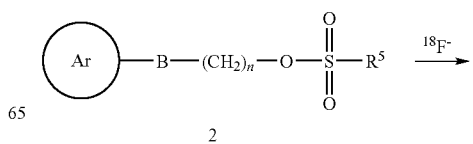

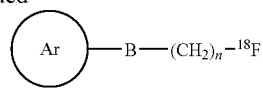

7 wherein

B, $R^5$ and n are the same as defined in claim 2 for the Formula 2.

Here, the useful organic solvent may be selected from the group consisting of acetonitrile, dimethylformamide (DMF), dimethylsulfoxide (DMSO), tertiary alcohol, and mixed solvents thereof.

The $^{18}F$ labeling method according to the present invention may be performed in various manners according to whether a polymer cartridge is used or not.

First, when a polymer cartridge is used, an aqueous solution of [$^{18}F$]fluoride/[$^{18}O$]H$_2$O produced by cyclotron is captured in a Chromafix or QMA cartridge and water in the cartridge is removed using a methanol solution. That is to say, [$^{18}F$]fluoride captured in the cartridge is eluted using the methanol solution containing in 83.8% acetonitrile/water by passing through the cartridge. The water and methanol solvent are completely removed by blowing nitrogen with heating to 100-120° C. for 1-3 minutes. The $^{18}F$ labeled compound precursor of Formula 2 is put into the reaction vessel, and suitable reaction solvents are added thereto for dissolution. The dissolved reaction mixture is heated for 3-30 minutes at 100-130° C., and the solvent is removed at the same temperature while drying by blowing with nitrogen gas. Acetonitrile is added to solvent-free residues to dissolve the remaining compounds. 1N HCl is added, heated at 50-100° C. for 2-10 minutes, cooled to room temperature, and then neutralized using an aqueous solution of 1N sodium hydrogen carbonate. To the neutralized mixture is added distilled water, and the reaction mixture is allowed to pass through a C-18 cartridge (SepPak) and then washed with distilled water. Acetonitrile is allowed to flow into the cartridge so that the compounds remaining in the C-18 cartridge is eluted and some or all of the compound residues are injected into high performance liquid chromatography (HPLC), thereby isolating the $^{18}F$ labeled compounds.

Next, when a polymer cartridge is not used, an aqueous solution of [$^{18}F$]fluoride/[$^{18}O$]H$_2$O produced by cyclotron is put into a reaction vessel, and TBAHCO$_3$ or TBAOH is added thereto. Then, acetonitrile is added to remove water while blowing nitrogen gas with heating to 100-120° C. The processes of adding acetonitrile and removing water are repeatedly performed 3-4 times until the water in the reaction mixture is completely removed. The $^{18}F$ labeled compound precursor of Formula 2 are put into the reaction vessel, and suitable reaction solvents are added thereto for dissolution. The dissolved reaction mixture is heated for 3-30 minutes at 100-130° C., and the solvent is removed at the same temperature while drying by blowing with nitrogen gas. Acetonitrile is added to solvent-free residues to dissolve the remaining compound. 1N HCl is added, heated at 50-100° C. for 2-10 minutes, cooled to room temperature, and then neutralized using an aqueous solution of 1N sodium hydrogen carbonate. To the neutralized mixture is added distilled water, and the reaction mixture is allowed to pass through a C-18 cartridge (SepPak) and then washed with distilled water. Acetonitrile is allowed to flow into the cartridge so that the compounds remaining in the C-18 cartridge is eluted and some or all of the compound residues are injected into HPLC, thereby isolating the $^{18}F$ labeled compounds.

Further, the present invention provides a pharmaceutical composition for diagnosis or treatment of degenerative brain disease containing 2-arylbenzothiophene derivative or a pharmaceutically acceptable salt thereof as an active ingredient.

Here, the degenerative brain disease is Alzheimer's disease. AD is the most common form of primary dementia. However, since diagnosis of AD is difficult to confirm simply by clinical dementia, AD is usually diagnosed by a physician observing patients' symptoms and ruling out other possible causes of dementia.

A variety of pathological features are seen from AD patients. However, AD is above all accompanied by two major morphological changes, including senile plaques generally distributed in the neocortex and neurofibrillary degeneration. neurofibrillary tangles. The neurofibrillary degeneration is observed in forms of neurofibrillary tangles and neuropil threads containing paired helical filaments, which are abnormally phosphorylated tau filaments. Several lines of evidence suggest that beta-amyloid (Aβ) is the major protein found in amyloid plaques and the deposition of Aβ plays a key role in the pathogenesis of AD, which are suggested by several lines of empirical evidence.

The Aβ, which is an internal polypeptide derived from a type 1 integral membrane protein, termed amyloid precursor protein (APP), is a 39-43 amino acid peptide composed of an extracellular domain and a membrane domain. The mechanism of the Aβ to cause neuronal cell death will now be described briefly. In general, it is hypothetically accepted that the Aβ is derived by sequential proteolytic processing of amyloid precursor protein (APP) and that agglomeration of the Aβ produces a beta-pleated sheet, eventually inducing neuronal cell death. Accordingly, if detection of the presence of Aβ is available before senile plaques or neurofibrillary tangles are observed, diagnosis of AD can be made at an earlier stage.

The 2-arylbenzothiophene derivative of Formula 1, or the pharmaceutically acceptable salt thereof may be administered in varying formulations for oral or parenteral administration in clinical use. When formulated into suitable pharmaceutical preparations for clinical use, the 2-arylbenzothiophene derivative of Formula 1, or the pharmaceutically acceptable salt thereof can be presented as generally used diluents or adjuvants, for example, fillers, bulking agents, binders, wetting agents, disintegrating agents, or surfactants.

Solid formulations for oral use may include tablets, pills, powders, capsules, troches, and the like, and the aryl derivative of Formula 1 or the pharmaceutically acceptable salt thereof may be mixed with one or more adjuvants, such as starch, calcium carbonate, sucrose, lactose or gelatin. In addition to the simple adjuvants, lubricants such as magnesium stearate, talc, or the like may be used. Liquid formulations for oral administration are suspending agents, emulsifying agents, or syrups, and may include generally used simple diluents such as water, liquids, paraffin, and other adjuvants, for example, wetting agents, sweetening agents, perfuming agents and preservatives.

Formulations for parenteral administration may include sterilized aqueous solutions, water-insoluble excipients, suspensions, emulsions, freeze drying agents and suppositories.

The water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

In addition, the 2-arylbenzothiophene derivative of Formula 1 or the pharmaceutically acceptable salt thereof may be administered to a patient in varying amounts according to factors such as the age, sex, and weight of the patient, the type of administration, the patient's physical condition and severity of the condition being treated, and the like. In a case of an adult patient weighing 70 kg, for example, the dosage of administration is generally about 0.1-1000 mg/day, preferably about 1-500 mg/day. Further, the 2-arylbenzothiophene derivative of Formula 1 or the pharmaceutically acceptable salt thereof may be administered in more than one dose of injection at regular intervals per day according to physician's or pharmacist's determination.

The following examples illustrate the invention described above, but do not imply any limitation of scope beyond the disclosure above.

Preparation Examples 1-2

Preparation of 4-methoxybenzothiophene and 6-methoxybenzothiophene

Bromoacetaldehydediethylacetal (2.15 g, 15.0 mmol) was slowly added to an acetone solution (50 mL) containing 2-methoxythiophenol (90, 1.92 mL, 12.8 mmol) and potassium carbonate (2.65 g, 19 mmol) at room temperature, and the reaction mixture was stirred at room temperature for 12 hours. Water (100 mL) was added to the reaction mixture and organic compounds were extracted with ethyl acetate, evaporated after a treatment with sodium sulfate, and concentrated under reduced pressure, and purified by column chromatography to give the target compound (2,2-diethoxyethyl)(3-methoxyphenyl)sulfane as a pale yellow liquid (91, 2.61 g, 80%) having the following physical data:

$^1$H NMR (400 MHz, CDCl$_3$) δ 1.20 (t, J=7.2 Hz, 6H), 3.13 (d, J=5.6 Hz, 2H), 3.65-3.76 (m, 2H), 3.52-3.56 (m, 2H), 3.82 (s, 3H), 4.65 (t, J=5.6 Hz, 1H), 6.70 (dd, J=8.0 Hz, 2.0 Hz, 1H), 6.94 (m, 2H), 7.17 (t, J=4.0 Hz, 1H); $^{13}$C NMR (100 MHz, CDCl$_3$) δ 15.4, 37.4, 55.4, 62.3, 101.9, 111.9, 114.6, 121.3, 129.9, 138.0, 160.0.

To the obtained (2,2-diethoxyethyl)(3-methoxyphenyl)sulfane (91, 3.6 g, 14.0 mmol) dissolved in a dichloromethane solution (70 mL) was slowly added trifluoroborane etherate (BF$_3$-Et$_2$O; 1.75 mL, 13.72 mmol) at room temperature under nitrogen, and the reaction mixture was stirred for one hour and neutralized with a sodium bicarbonate solution at room temperature. Organic layer was isolated, organic compounds in water were extracted with dichloromethane, the recovered organic solution was evaporated after a treatment with sodium sulfate, and concentrated under reduced pressure. After concentration, residues were purified by column chromatography to give the target compounds 4-methoxybenzothiophene (92a, 368 mg, 16%) and 6-methoxybenzothiophene compounds (92b, 1.38 g, 60%) as transparent liquids.

Preparation Example 1

4-methoxybenzothiophene (92a); $^1$H NMR (400 MHz, CDCl$_3$) δ 3.95 (s, 3H), 6.74 (d, J=7.6 Hz, 1H), 7.27 (d, J=8.0 Hz, 1H), 7.32 (d, J=5.6 Hz, 1H), 7.46 (dd, J=0.8, 7.2 Hz, 1H), 7.50 (d, J=5.6 Hz, 1H); $^{13}$C NMR (100 MHz, CDCl$_3$) δ 55.42, 103.72, 114.76, 120.44, 124.48, 125.15, 130.35, 141.21, 154.93.

Preparation Example 2

6-methoxybenzothiophene (92b); $^1$H NMR (400 MHz, CDCl$_3$) δ 3.82 (s, 3H), 7.01 (dd, J=8.8, 2.0 Hz, 1H), 7.56 (d, J=2.0 Hz, 2H), 7.82 (m, 2H); $^{13}$C NMR (100 MHz, CDCl$_3$) δ 56.0, 105.3, 114.9, 125.1, 131.4, 135.3, 138.9, 144.9, 158.0.

Preparation Example 3

Preparation of 6-hydroxybenzothiophene

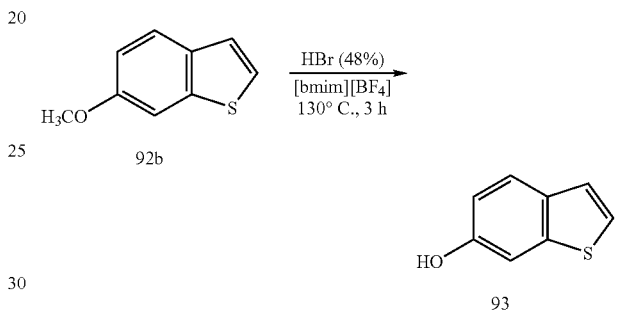

6-Methoxybenzothiophene (92b, 1.00 g, 6.09 mmol) obtained in Preparation Example 2 and concentrated boric acid (48% aqueous solution, 3.00 mL, 18.27 mmol) were added to [bmim][BF$_4$] (10 mL) and heated at 130° C. for 3 hours. The reaction mixture was cooled to room temperature and water was added thereto. Then, organic compounds were extracted with ethyl acetate, and the solvents were removed under reduced pressure and purified by column chromatography to give the target compound 6-hydroxybenzothiophene (93, 732 mg, 80%) as a pale pink solid.

$^1$H NMR (200 MHz, CDCl$_3$) δ 5.67 (brs, 1H, OH), 6.90 (dd, J=1.8, 2.2 Hz, 1H), 7.22 (s, 2H), 7.29 (d, J=1.8 Hz, 1H), 7.64 (d, J=8.4 Hz, 1H); $^{13}$C NMR (50 MHz, CDCl$_3$) δ 107.8, 114.2, 123.4, 123.8, 124.3, 133.9, 141.2, 152.9.

Preparation Examples 4-6

Preparation Example 4

Preparation of 6-(2-fluoroethoxy)benzothiophene (94a)

To a reaction vessel containing 6-hydroxybenzothiophene (93, 3.137 g, 20.9 mmol) obtained in Preparation Example 3 and sodium hydride (60% NaH, 1.254 g, 31.4 mmol) was put anhydrous tetrahydrofuran (50 mL) under nitrogen to be dissolved, stirred at 0° C. for 15 minutes. 2-Fluoroethylmethane sulfonate (FCH$_2$CH$_2$OMs, 2.969 g, 20.9 mmol) was slowly added at 0° C., heated to reflux for 12 hours, and cooled to room temperature, followed by adding water. The resulting product was extracted with ethyl acetate, and the extracted organic solution was washed with a saturated solution of sodium chloride, evaporated after a treatment with sodium sulfate, and purified by column chromatography to give the target compound 6-(2-fluoroethoxy)benzothiophene (94a, 2.897 g, 71%).

$^1$H NMR (400 MHz, CDCl$_3$) δ 4.24 (dm, J=28.0 Hz, 2H), 4.76 (dm, J=47.2 Hz, 2H), 7.02 (dd, J=8.8, 2.4 Hz, 1H), 7.27-7.22 (m, 2H), 7.34 (d, J=2.4 Hz, 1H), 7.69 (d, J=8.8 Hz, 1H); $^{13}$C NMR (100 MHz, CDCl$_3$) δ 67.9 (d, J=20.5 Hz), 82.2 (d, J=169.8 Hz), 106.2, 115.0, 123.6, 124.3, 124.4, 134.3, 141.2, 156.3.

Preparation Example 5

Preparation of 6-(3-fluoropropoxy)benzothiophene (94b)

6-(3-Fluoropropoxy)benzothiophene (94b, 2.440 mg, 87%) was prepared in the same manner as in Preparation Example 4 using 6-hydroxybenzothiophene (93, 2.00 g, 13.32 mmol) obtained in Preparation Example 3, sodium hydride (60% NaH, 799 mg, 19.97 mmol) and 3-fluoropropylmethane sulfonate (FCH$_2$CH$_2$CH$_2$OMs, 2.288 g, 14.65 mmol).

$^1$H NMR (400 MHz, CDCl$_3$) δ 2.18 (dm, J=26.0 Hz, 2H), 4.13 (t, J=6.0 Hz, 2H), 4.65 (dt, J=46.8, 6.0 Hz, 2H), 6.98 (dd, J=8.8, 2.4 Hz, 1H), 7.21-7.25 (m, 2H), 7.34 (d, J=2.0 Hz, 1H), 7.67 (d, J=8.4 Hz, 1H); $^{13}$C NMR (100 MHz, CDCl$_3$) δ 30.1 (d, J=20.5 Hz), 63.6 (d, J=5.3 Hz), 80.4 (d, J=163.0 Hz), 105.3, 114.2, 122.9, 123.4, 123.7, 133.4, 140.7, 156.1.

Preparation Example 6

Preparation of 6-(3-t-butyldimethylsilyloxypropoxy)benzothiophene (94c)

6-(3-t-Butyldimethylsilyloxypropoxy)benzothiophene (94c, 2.95 g, 99%) was prepared in the same manner as in Preparation Example 4 using 6-hydroxybenzothiophene (93, 1.38 g, 9.19 mmol) obtained in Preparation Example 3, sodium hydride (60% NaH, 551 mg, 13.78 mmol) and 3-(t-butyldimethylsilyloxy)propylbromide (TBDMS-OCH$_2$CH$_2$CH$_2$Br, 2.560 g, 10.11 mmol).

$^1$H NMR (400 MHz, CDCl$_3$) δ 0.05 (s, 6H), 0.89 (s, 9H), 2.04-1.98 (m, 2H), 3.82 (t, J=6.0 Hz, 2H), 4.11 (t, J=6.0 Hz, 2H), 6.98 (dd, J=8.4, 2.0 Hz, 1H), 7.24-7.22 (m, 2H), 7.35 (d, J=2.4 Hz, 1H), 7.66 (d, J=8.4 Hz, 1H); $^{13}$C NMR (100 MHz, CDCl$_3$) δ −5.2, 18.4, 26.0, 32.5, 59.5, 64.9, 105.6, 114.7, 123.3, 123.5, 123.9, 133.4, 141.0, 156.7.

Preparation Examples 7-11

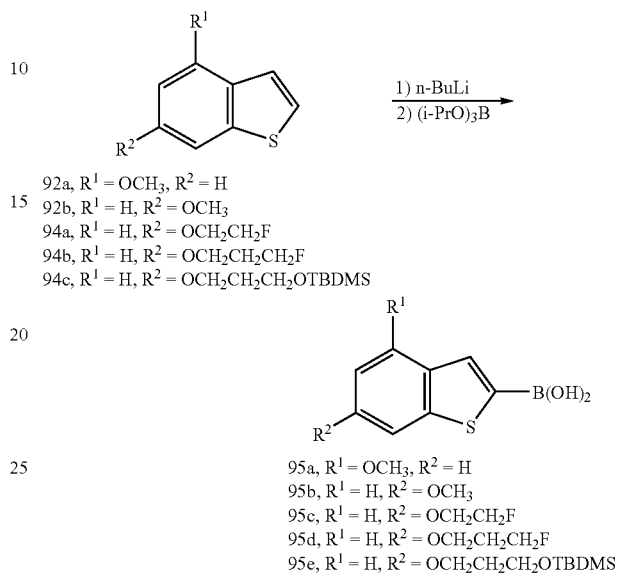

92a, R$^1$ = OCH$_3$, R$^2$ = H
92b, R$^1$ = H, R$^2$ = OCH$_3$
94a, R$^1$ = H, R$^2$ = OCH$_2$CH$_2$F
94b, R$^1$ = H, R$^2$ = OCH$_2$CH$_2$CH$_2$F
94c, R$^1$ = H, R$^2$ = OCH$_2$CH$_2$CH$_2$OTBDMS

95a, R$^1$ = OCH$_3$, R$^2$ = H
95b, R$^1$ = H, R$^2$ = OCH$_3$
95c, R$^1$ = H, R$^2$ = OCH$_2$CH$_2$F
95d, R$^1$ = H, R$^2$ = OCH$_2$CH$_2$CH$_2$F
95e, R$^1$ = H, R$^2$ = OCH$_2$CH$_2$CH$_2$OTBDMS

Preparation Example 7

Preparation of 4-methoxybenzothiophene-2-boronic acid (95a)

2.5 M Hexane solution of normal butyl lithium (1.07 mL, 2.67 mmol) was slowly added under nitrogen to the 4-methoxybenzothiophene (92a, 368 mg, 2.24 mmol) obtained in Preparation Example 1 dissolved in an anhydrous tetrahydrofuran solution at −78° C., and the reaction mixture was stirred for 30 minutes. To the reaction mixture was slowly added a triisopropylborate solution (i-PrO)$_3$B) (0.55 mL, 2.69 mmol) at room temperature, stirred for one hour, and the reaction was terminated by adding a solution of 2N hydrochloride. The resulting product was extracted with ethyl acetate, evaporated after a treatment with sodium sulfate, and concentrated under reduced pressure, recrystallized and filtered using hexane and ethyl acetate to give the target product 4-methoxybenzothiophene-2-boronic acid (95a, 289 mg, 62%).

$^1$H NMR (400 MHz, CDCl$_3$ and DMSO-d$_6$) δ 3.72 (s, 3H), 6.48 (d, J=8.0 Hz, 1H), 7.04 (dd, J=0.8, 7.2 Hz, 1H), 7.20 (d, J=5.6 Hz, 1H), 7.85 (s, 1H); $^{13}$C NMR (100 MHz, CDCl$_3$ and DMSO-d$_6$) δ 54.8, 77.3, 102.7, 114.2, 125.4, 129.0, 131.0, 144.4, 154.6.

Preparation Example 8

Preparation of 6-methoxybenzothiophene-2-boronic acid (95b)

6-Methoxybenzothiophene-2-boronic acid (95b, 1.73 g, 99%) was prepared in the same manner as in Preparation Example 7 using 6-methoxybenzothiophene (92b, 1.38 g, 8.38 mmol) obtained in Preparation Example 2.

$^1$H NMR (400 MHz, CDCl$_3$) δ 3.82 (s, 3H), 7.01 (dd, J=8.8 Hz, 2.0 Hz, 1H), 7.56 (d, J=2.0 Hz, 2H), 7.82 (m, 2H); $^{13}$C NMR (100 MHz, CDCl$_3$) δ 56.0, 105.3, 114.9, 125.1, 131.4, 135.3, 138.9, 144.9, 158.0.

Preparation Example 9

Preparation of 6-(2-fluoroethoxy)benzothiophene-2-boronic acid (95c)

6-(2-Fluoroethoxy)benzothiophene-2-boronic acid (95c, 3.478, 100%) was prepared in the same manner as in Preparation Example 7 using 6-(2-fluoroethoxy)benzothiophene (94a, 2.845 g, 14.50 mmol) obtained in Preparation Example 4.

$^1$H NMR (400 MHz, CD$_3$OD) δ 4.28 (dm, J=29.2 Hz, 2H), 4.74 (dm, J=48.0 Hz, 2H), 7.01 (d, J=8.8 Hz, 1H), 7.43 (s, 1H), 7.76 (m, 2H); $^{13}$C NMR (100 MHz, CD$_3$OD) δ 67.7 (d, J=19.7), 82.0 (d, J=168.3 Hz), 104.7, 114.8, 124.8, 132.9, 135.4, 144.8, 157.4.

Preparation Example 10

Preparation of 6-(2-fluoropropoxy)benzothiophene-2-boronic acid (95d)

6-(3-Fluoropropoxy)benzothiophene-2-boronic acid (95d, 2.20 g, 77%) was prepared in the same manner as in Preparation Example 7 using 6-(3-fluoropropoxy)benzothiophene (94b, 2.377 g, 11.30 mmol) obtained in Preparation Example 5.

$^1$H NMR (400 MHz, CD$_3$OD) δ 2.18 (dm, J=25.2 Hz, 2H), 4.16 (t, J=6.0 Hz, 2H), 4.64 (dt, J=47.2, 6.0 Hz, 2H), 6.98 (dd, J=8.8, 2.0 Hz, 1H), 7.42 (s, 1H), 7.74 (d, J=8.4 Hz, 1H), 7.78 (s, 1H); $^{13}$C NMR (100 MHz, CD$_3$OD) δ 30.4 (d, J=20.0), 63.9 (d, J=6.0 Hz), 80.5 (d, J=162.1 Hz), 104.6, 114.8, 124.7, 133.0, 135.2, 144.9, 157.7.

Preparation Example 11

Preparation of 6-(3-t-butyldimethylsilyloxypropoxy)benzothiophene-2-boronic acid (95e)

6-(3-t-Butyldimethylsilyloxypropoxy)benzothiophene-2-boronic acid (95e, 1.157 g, 78%) was prepared in the same manner as in Preparation Example 7 using 6-(3-t-butyldimethylsilyloxypropoxy)benzothiophene (94c, 1.307 g, 4.05 mmol) obtained in Preparation Example 6.

$^1$H NMR (400 MHz, CD$_3$OD) δ 0.01 (s, 6H), 0.85 (s, 9H), 1.91 (q, J=6.0 Hz, 2H), 3.76 (t, J=6.0 Hz, 2H), 4.02 (t, J=6.0 Hz, 2H), 6.90 (dd, J=8.8, 2.4 Hz, 1H), 7.30 (d, J=2.4 Hz, 1H), 7.65 (d, J=8.8 Hz, 1H), 7.71 (s, 1H); $^{13}$C NMR (100 MHz, CD$_3$OD) δ −6.3, 18.0, 25.3, 32.3, 59.4, 64.4, 104.6, 114.8, 124.6, 132.4, 135.1, 145.2, 157.7.

Examples 1-3

Preparation of 2-arylbenzothiophene derivatives

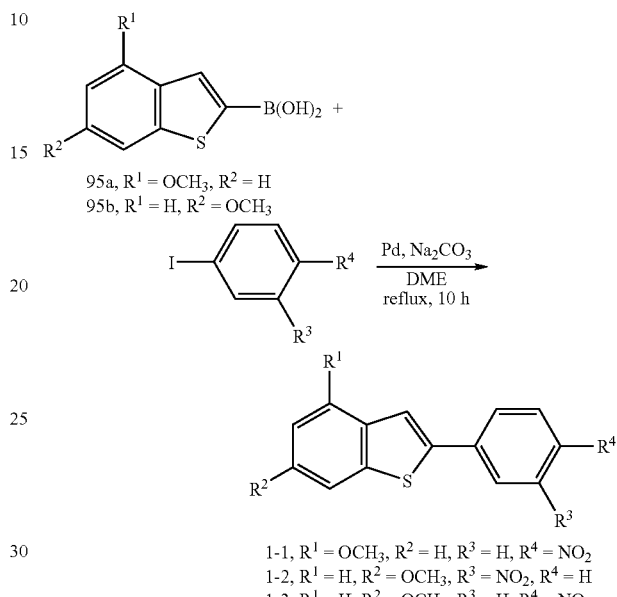

95a, R$^1$ = OCH$_3$, R$^2$ = H
95b, R$^1$ = H, R$^2$ = OCH$_3$ 1-1, R$^1$ = OCH$_3$, R$^2$ = H, R$^3$ = H, R$^4$ = NO$_2$
1-2, R$^1$ = H, R$^2$ = OCH$_3$, R$^3$ = NO$_2$, R$^4$ = H
1-3, R$^1$ = H, R$^2$ = OCH$_3$, R$^3$ = H, R$^4$ = NO$_2$

Example 1

Preparation of 2-(4-nitrophenyl)-4-methoxybenzothiophene (1-1)

To a suspension of anhydrous 1,2-dimethoxyethane (DME, 20 mL) containing a palladium tetrakis catalyst (Pd (PPh$_3$)$_4$ (49.7 mg, 0.043 mmol) was added 4-iodonitrobenzene (535.8 mg, 2.15 mmol), stirred at room temperature for 10 minutes, followed by adding 4-methoxybenzothiophene-2-boronic acid (95a, 470 mg, 2.26 mmol) and 2.0 M sodium carbonate aqueous solution (43 mL, 0.086 mmol). The reaction mixture was heated to reflux for 10 hours and cooled to room temperature, and ice water was added. The resulting product was extracted with ethyl acetate, evaporated after a treatment with, and purified by column chromatograph to give the target compound 2-(4-nitrophenyl)-4-methoxybenzothiophene (1-1, 560 mg, 87%).

$^1$H NMR (400 MHz, CDCl$_3$) δ 7.02 (dd, J=8.8 Hz, 2.4 Hz, 1H), 7.31 (d, J=2.4 Hz, 1H), 7.63 (s, 1H), 7.70 (d, J=8.8 Hz, 1H), 7.79 (d, J=8.8 Hz, 2H), 8.26 (d, J=8.8 Hz, 2H); $^{13}$C NMR (100 MHz, CDCl$_3$) δ 55.6, 104.7, 115.3, 122.1, 124.4, 125.0, 126.3, 134.3, 138.5, 140.8, 141.9, 146.7, 158.4.

Example 2

Preparation of 2-(3-nitrophenyl)-6-methoxybenzothiophene (1-2)

2-(3-Nitrophenyl)-6-methoxybenzothiophene (1-2, 393 mg, 65%) was prepared as a pale yellow solid in the same manner as in Example 1 using 6-methoxybenzothiophene-2- boronic acid (95b, 500 mg, 2.40 mmol) obtained in Preparation Example 8 and 3-iodonitrobenzene (586 mg, 2.30 mmol).

$^1$H NMR (400 MHz, CDCl$_3$) δ 3.90 (s, 3H), 7.01 (dd, J=0.8, 2.4 Hz, 1H), 7.32 (s, 1H), 7.55-7.59 (m, 2H), 7.69 (d, J=8.8 Hz, 1H), 7.95 (d, J=6.0 Hz, 1H), 8.91 (d, J=8 Hz, 1H), 8.51 (s, 1H), $^{13}$C NMR (100 MHz, CDCl$_3$) δ 55.6, 104.8, 115.1, 120.6, 121.0, 122.1, 124.8, 129.9, 131.7, 134.3, 136.3, 138.4, 141.4, 148.0, 158.1.

Example 3

2-(4-nitrophenyl)-6-methoxybenzothiophene (1-3)

2-(4-Nitrophenyl)-6-methoxybenzothiophene (1-3, 560 mg, 87%) was prepared as a pale yellow solid in the same manner as in Example 1 using 6-methoxybenzothiophene-2-boronic acid (95b, 470 mg, 2.26 mmol) obtained in Preparation Example 8 and 4-iodonitrobenzene (536 mg, 2.15 mmol).

$^1$H NMR (400 MHz, CDCl$_3$) δ 7.02 (dd, J=8.8 Hz, 2.4 Hz, 1H), 7.31 (d, J=2.4 Hz, 1H), 7.63 (s, 1H), 7.70 (d, J=8.8 Hz, 1H), 7.79 (d, J=8.8 Hz, 2H), 8.26 (d, J=8.8 Hz, 2H); $^{13}$C NMR (100 MHz, CDCl$_3$) δ 55.6, 104.7, 115.3, 122.1, 124.4, 125.0, 126.3, 134.3, 138.5, 140.8, 141.9, 146.7, 158.4.

Example 4

Preparation of 2-(4-nitrophenyl)-6-hydroxybenzothiophene (1-4)

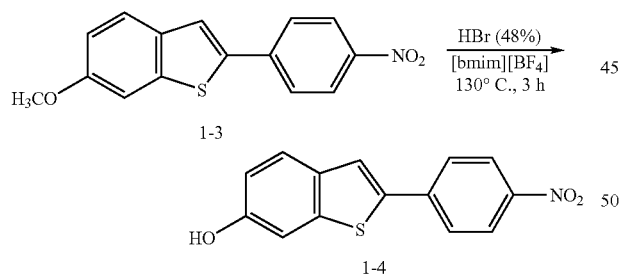

2-(4-Nitrophenyl)-6-hydroxybenzothiophene (1-4, 323 mg, 81%) was prepared as a pale orange solid in the same manner as in Preparation Example 3 using 2-(4-nitrophenyl)-6-methoxybenzothiophene (1-3, 419 mg, 1.47 mmol) obtained in Example 3. The obtained target compound 1-4 had a melting point of 265.0-265.2° C., and the following physical data;

$^1$H NMR (400 MHz, DMSO-d$_6$) δ 6.92 (dd, J=8.8 Hz, 2.4 Hz, 1H), 7.31 (d, J=2.0 Hz, 1H), 7.72 (d, J=8.4 Hz, 1H), 7.94 (dd, J=7.2, 2.0 Hz, 2H), 7.98 (s, 1H), 8.27 (dd, J=7.2, 2.0 Hz, 2H); $^{13}$C NMR (100 MHz, DMSO-d$_6$) δ 107.4, 115.8, 123.6, 124.7, 125.7, 126.4, 133.3, 136.7, 140.5, 141.6, 146.3, 156.5.

Examples 5-6

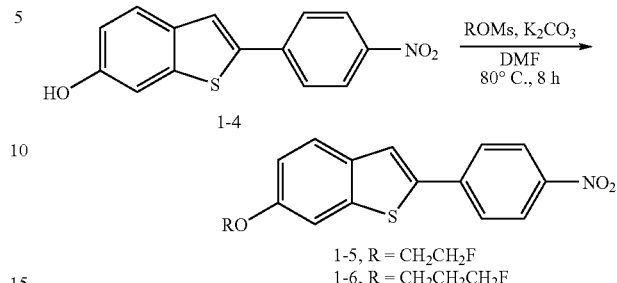

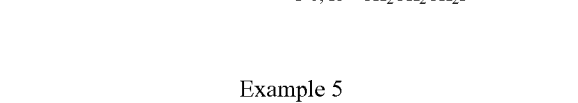

1-5, R = CH$_2$CH$_2$F
1-6, R = CH$_2$CH$_2$CH$_2$F

Example 5

Preparation of 2-(4-nitrophenyl)-4-(2-fluoroethoxy) benzothiophene (1-5)

Potassium carbonate (611 mg, 4.42 mmol) and 2-fluoroethyl methane sulfonate (FCH$_2$CH$_2$OMs, 251 mg, 1.77 mmol) were added to 2-(4-nitrophenyl)-6-hydroxybenzothiophene (1-4, 400 mg, 1.47 mmol) obtained in Example 4 dissolved in a solution of dimethylformamide (DMF, 100 mL), heated at 80° C. for 8 hours, cooled to room temperature, followed by adding water. The resulting product was extracted with ethyl acetate, evaporated after a treatment with sodium sulfate under reduced pressure. Purification was performed by column chromatograph to give the target compound 2-(4-nitrophenyl)-4-(2-fluoroethoxy)benzothiophene (1-5, 224 mg, 48%) as a yellow solid. The obtained target compound 1-5 had a melting point of 176.5-178.0° C., and the following physical data;

$^1$H NMR (400 MHz, CDCl$_3$) δ 4.30 (dt, J=27.6, 4.2 Hz, 2H), 4.81 (dt, J=47.6, 4.2 Hz, 2H), 7.06 (dd, J=8.8, 2.4 Hz, 1H), 7.34 (d, J=2.4 Hz, 1H), 7.64 (s, 1H), 7.72 (d, J=8.8 Hz, 1H), 7.82 (d, J=8.8 Hz, 2H), 8.27 (d, J=8.8 Hz, 2H); $^{13}$C NMR (100 MHz, CDCl$_3$) δ 67.6 (d, J=20.5 Hz), 81.8 (d, J=169.8 Hz), 105.7, 115.5, 121.9, 124.3, 125.0, 126.2, 126.4, 134.6, 140.5, 141.6, 146.7, 156.9.

Example 6

Preparation of 2-(4-nitrophenyl)-6-(3-fluoropropoxy) benzothiophene (1-6)

2-(4-Nitrophenyl)-4-(3-fluoropropoxy)benzothiophene (1-6, 224 mg, 92%) was prepared as a yellow solid in the same manner as in Example 5 using sodium carbonate (305 mg, 2.21 mmol), 3-fluoropropyl methanesulfonate (FCH$_2$CH$_2$CH$_2$OMs, 137 mg, 0.88 mmol) and 2-(4-nitrophenyl)-6-hydroxy benzothiophene (1-4, 200 mg, 0.74 mmol). The obtained target compound 1-6 had a melting point of 128.9-130.3° C., and the following physical data;

$^1$H NMR (400 MHz, CDCl$_3$) δ 1.98 (dt, J=26.4, 5.8 Hz, 2H), 4.23 (t, J=6.0 Hz, 2H), 4.72 (dt, J=47.2, 5.2 Hz, 2H), 6.75-6.78 (m, 1H), 7.06 (d, J=2.0 Hz, 1H), 7.35 (s, 1H), 7.66 (d, J=8.0 Hz, 1H), 7.75 (d, J=8.8 Hz, 2H), 8.21 (d, J=8.4 Hz, 2H); $^{13}$C NMR (100 MHz, CDCl$_3$) δ 30.4 (d, J=19.7 Hz), 63.9 (d, J=5.3 Hz), 80.6 (d, J=162.9 Hz), 105.4, 115.4, 121.9, 124.2, 124.9, 126.1, 126.3, 134.3, 138.4, 140.5, 141.7, 146.5, 157.3.

Examples 7-10

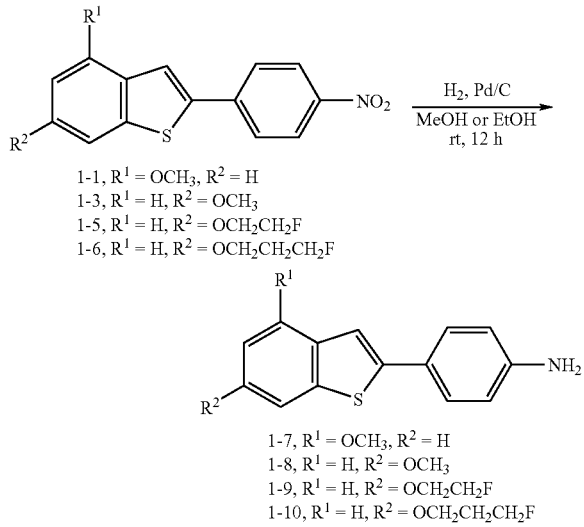

1-1, $R^1$ = OCH$_3$, $R^2$ = H
1-3, $R^1$ = H, $R^2$ = OCH$_3$
1-5, $R^1$ = H, $R^2$ = OCH$_2$CH$_2$F
1-6, $R^1$ = H, $R^2$ = OCH$_2$CH$_2$CH$_2$F 1-7, $R^1$ = OCH$_3$, $R^2$ = H
1-8, $R^1$ = H, $R^2$ = OCH$_3$
1-9, $R^1$ = H, $R^2$ = OCH$_2$CH$_2$F
1-10, $R^1$ = H, $R^2$ = OCH$_2$CH$_2$CH$_2$F

Example 7

Preparation of 2-(4-aminophenyl)-4-methoxybenzothiophene (1-7)

2-(4-Nitrophenyl)-4-methoxybenzothiophene (1-1, 200 mg, 0.71 mmol) obtained in Example 1 and 10% palladium on charcoal (Pd/C, 5 mg) were added to a round bottom flask containing anhydrous methanol (10 mL) and sealed with a septum. Then, the flask is filled with hydrogen gas, provided with a hydrogen balloon and stirred at room temperature for 12 hours. Then, the resulting product was filtered using celite, and a methanol solvent was removed under reduced pressure to give the target compound 2-(4-aminophenyl)-4-methoxybenzothiophene (1-7, 151 mg, 88%).

$^1$H NMR (400 MHz, DMSO-d$_6$) δ 3.79 (br, 2H), 3.97 (s, 3H), 6.66-6.72 (m, 3H), 7.18 (t, J=8.0 Hz, 1H), 7.37 (dd, J=8.0 Hz, 0.8 Hz, 1H), 7.49-7.51 (m, 2H), 7.54 (d, J=0.4 Hz, 1H); $^{13}$C NMR (100 MHz, DMSO-d$_6$) δ 55.4, 104.1, 113.8, 114.6, 115.2, 124.6, 124.9, 127.5, 131.6, 140.2, 143.2, 146.5, 154.5.

Example 8

Preparation of 2-(4-aminophenyl)-6-methoxybenzothiophene (1-8)

2-(4-Aminophenyl)-6-methoxybenzothiophene (1-8, 129 mg, 92%) was prepared as a pale orange solid in the same manner as in Example 7 using 2-(4-nitrophenyl)-6-methoxybenzothiophene (1-3, 160 mg, 0.56 mmol) obtained in Example 3.

$^1$H NMR (200 MHz, DMSO-d$_6$) δ 3.77 (s, 2H), 3.87 (s, 3H), 6.71 (d, J=8.4 Hz, 2H), 6.81 (dd, J=8.4 Hz, 2.6 Hz, 1H), 7.28 (s, 2H), 7.48 (d, J=8.4 Hz, 2H), 7.59 (d, J=8.8 Hz, 1H); $^{13}$C NMR (50 MHz, DMSO-d$_6$) δ 55.3, 105.0, 113.8, 113.9, 115.4, 121.2, 123.3, 126.5, 134.6, 138.9, 141.9, 148.8, 156.3.

Example 9

Preparation of 2-(4-aminophenyl)-6-(2-fluoroethoxy)benzothiophene (1-9)

2-(4-Aminophenyl)-6-(2-fluoroethoxy)benzothiophene (1-9, 136 mg, 68%) was prepared as a pale orange solid in the same manner as in Example 7 using 2-(4-nitrophenyl)-6-(2-fluoroethoxy)benzothiophene (1-5, 222 mg, 0.67 mmol) obtained in Example 5 in a solvent of ethanol (10 mL). The obtained target compound 1-9 had a melting point of 165.6-168.5° C., and the following physical data;

$^1$H NMR (400 MHz, DMSO-d$_6$) δ 4.28 (dt, J=30.4, 3.4 Hz, 2H), 4.76 (dt, J=47.6, 3.4 Hz, 2H), 5.41 (s, 1H), 6.62 (d, J=8.0 Hz, 2H), 6.98 (dd, J=8.4, 1.2 Hz, 1H), 7.37 (s, 1H), 7.40 (d, J=5.2 Hz, 2H), 7.50 (s, 1H), 7.62 (d, J=8.4 Hz, 1H); $^{13}$C NMR (100 MHz, DMSO-d$_6$) δ 67.3 (d, J=18.9 Hz), 82.0 (d, J=165.2 Hz), 106.0, 113.8, 114.3, 115.4, 121.0, 123.4, 126.5, 134.9, 138.8, 142.2, 148.9, 155.1.

Example 10

Preparation of 2-(4-aminophenyl)-6-(3-fluoropropoxy)benzothiophene (1-10)

2-(4-Aminophenyl)-6-(3-fluoropropoxy)benzothiophene (1-10, 175 mg, 79%) was prepared as a pale orange solid in the same manner as in Example 7 using 2-(4-nitrophenyl)-6-(3-fluoropropoxy)benzothiophene (1-6, 244 mg, 0.735 mmol) obtained in Example 6. The obtained target compound 1-10 had a melting point of 119.6-123.2° C., and the following physical data;

$^1$H NMR (200 MHz, CDCl$_3$) δ 1.70 (dt, J=26.0, 6.1 Hz, 2H), 3.78 (s, 2H), 4.16 (t, J=3.0 Hz, 2H), 4.67 (dt, J=47.4, 5.9 Hz, 2H), 6.71 (d, J=7.8 Hz, 1H), 6.95 (dd, J=7.9, 2.3 Hz, 1H), 7.26-7.29 (m, 1H), 7.47 (d, J=7.8 Hz, 2H), 7.58 (d, J=8.4 Hz, 1H); $^{13}$C NMR (50 MHz, CDCl$_3$) δ 30.5 (d, J=19.7 Hz), 64.0 (d, J=5.3 Hz), 80.7 (d, J=163.0 Hz), 105.8, 114.4, 115.1, 116.6, 123.5, 124.9, 127.2, 135.1, 140.1, 142.3, 146.2, 155.9.

Examples 11-13

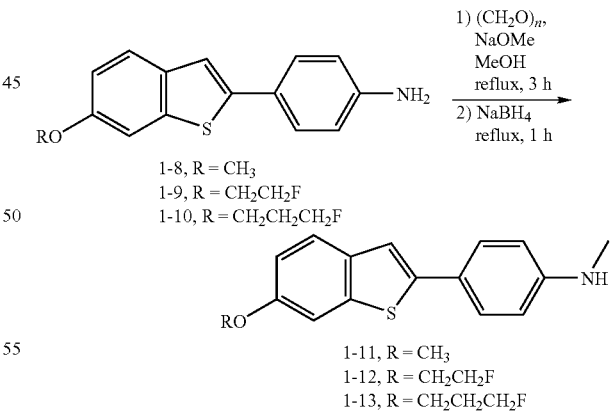

1-8, R = CH$_3$
1-9, R = CH$_2$CH$_2$F
1-10, R = CH$_2$CH$_2$CH$_2$F 1-11, R = CH$_3$
1-12, R = CH$_2$CH$_2$F
1-13, R = CH$_2$CH$_2$CH$_2$F

Example 11

Preparation of 2-[4-(N-monomethylamino)phenyl]-6-methoxy benzothiophene (1-11)

2-(4-Aminophenyl)-6-methoxybenzothiophene (1-8, 100 mg, 0.41 mmol) obtained in Example 8, sodium methoxide (NaOMe, 45 mg, 0.83 mmol) and p-formaldehyde $(CH_2O)_n$ (60 mg, 2.08 mmol) were added to a methanol solvent (15 mL), and the reaction mixture was heated to reflux for 3 hours and cooled to room temperature. Next, sodium borohydride ($NaBH_4$, 70 mg, 1.85 mmol) was added to the resulting mixture, heated to reflux again for one hour and cooled to room temperature, followed by adding water. Organic compounds were extracted using dichloromethane and evaporated after a treatment with sodium sulfate. Purification was performed by column chromatograph to give the target compound 2-[4-(N-monomethylamino)phenyl]-6-methoxybenzothiophene (1-11, 97 mg, 87%) as a white solid.

$^1$H NMR (400 MHz, DMSO-$d_6$) δ 2.85 (s, 3H) 3.84 (s, 3H), 6.60 (d, J=8.4 Hz, 2H), 6.91 (dd, J=6.4, 2.4 Hz, 1H) 7.23-7.25 (m, 2H), 7.48 (d, J=8.8 Hz, 2H), 7.55 (d, J=8.8 Hz, 1H); $^{13}$C NMR (100 MHz, DMSO-$d_6$) δ 30.7, 55.6, 104.9, 112.4, 114.0, 116.2, 123.4, 123.6, 127.2, 135.1, 140.1, 142.4, 149.0, 156.8.

Example 12

Preparation of 2-[4-(N-monomethylamino)phenyl]-6-(2-fluoroethoxy)benzothiophene (1-12)

2-[4-(N-Monomethylamino)phenyl]-6-(2-fluoroethoxy)benzothiophene (1-12, 54 mg, 74%) was prepared as a pale orange solid in the same manner as in Example 11 using 2-(4-aminophenyl)-6-(2-fluoroethoxy)benzothiophene (1-9, 70 mg, 0.244 mmol) obtained in Example 9. The obtained target compound 1-12 had a melting point of 156.9-159.7° C., and the following physical data;

$^1$H NMR (400 MHz, DMSO-$d_6$) δ 2.88 (s, 3H), 4.27 (dt, J=27.6, 4.2 Hz, 2H), 4.78 (dt, J=47.2, 4.4 Hz, 2H), 6.64 (d, J=8.8 Hz, 2H), 6.98 (dd, J=8.8, 2.4 Hz, 1H), 7.27 (s, 1H), 7.29 (d, J=2.4 Hz, 1H), 7.51 (d, J=8.4 Hz, 2H), 7.59 (d, J=8.8 Hz, 1); $^{13}$C NMR (100 MHz, DMSO-$d_6$) δ 30.6. 67.6 (d, J=19.7 Hz), 81.9 (d, J=169.8 Hz), 106.1, 112.4, 114.4, 116.1, 123.4, 123.5, 127.2, 135.5, 139.9, 142.9, 149.0, 155.5.

Example 13

Preparation of 2-[4-(N-monomethylamino)phenyl]-6-(3-fluoropropoxy)benzothiophene (1-13)

2-[4-(N-Monomethylamino)phenyl]-6-(3-fluoropropoxy)benzothiophene (1-13, 128 mg, 62%) was prepared as a pale orange solid in the same manner as in Example 11 using 2-(4-aminophenyl)-6-(3-fluoropropoxy)benzothiophene (1-10, 197 mg, 0.655 mmol) obtained in Example 10. The obtained target compound 1-13 had a melting point of 121.4-123.1° C., and the following physical data;

$^1$H NMR (200 MHz, CDCl$_3$) δ 2.13-2.32 (m, 2H), 2.90 (s, 3H), 3.92 (br s, 1H), 4.18 (t, J=5.8 Hz, 2H), 4.70 (dt, J=47.2, 5.9 Hz, 2H), 6.65 (d, J=8.8 Hz, 2H), 6.97 (dd, J=8.6, 2.4 Hz, 1H), 7.29 (s, 1H), 7.31 (d, J=2.6 Hz, 1H), 7.54 (d, J=8.8 Hz, 2H), 7.61 (d, J=8.4 Hz, 1H); $^{13}$C NMR (100 MHz, CDCl$_3$) δ 30.6, (d, J=27.3 Hz), 63.9 (d, J=5.3 Hz), 80.7 (d, J=163.0 Hz), 105.8, 112.4, 114.3, 116.1, 123.4, 123.5, 127.1, 135.2, 140.6, 142.5, 148.9, 155.8.

Examples 14-15

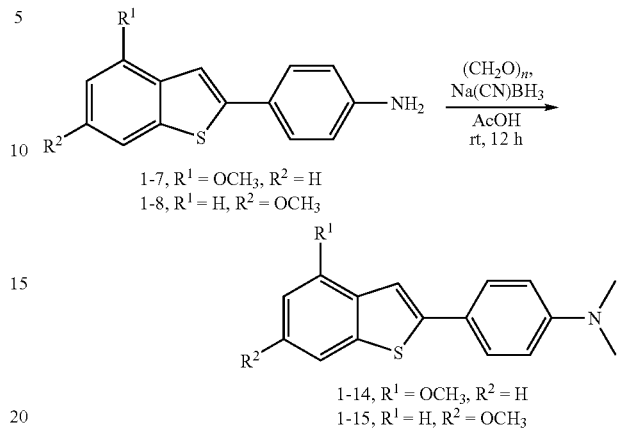

1-7, R$^1$ = OCH$_3$, R$^2$ = H
1-8, R$^1$ = H, R$^2$ = OCH$_3$ 1-14, R$^1$ = OCH$_3$, R$^2$ = H
1-15, R$^1$ = H, R$^2$ = OCH$_3$

Example 14

Preparation of 2-[4-(N,N-dimethylamino)phenyl]-4-methoxybenzothiophene (1-14)

2-(4-Aminophenyl)-4-methoxybenzothiophene (1-7, 100 mg, 0.40 mmol) obtained in Example 7, p-formaldehyde $(CH_2O)_n$, (120 mg, 4.00 mmol) and sodium cyanoborohydride (Na(CN)BH$_3$ (72 mg, 1.17 mmol) were dissolved in acetic acid (10 mL), and the reaction mixture was stirred at room temperature for 12 hours, followed by adding water. Then, sodium carbonate was added so as to adjust a pH level to be in a range of 8-9. Organic compounds were extracted with dichloromethane and evaporated after a treatment with sodium sulfate. Purification was performed by column chromatograph to give the target compound 2-[4-(N,N-dimethylamino)phenyl]-4-methoxybenzothiophene (1-14, 106 mg, 91%).

$^1$H NMR (200 MHz, CDCl$_3$) δ 2.96 (s, 6H), 3.93 (s, 3H), 6.69-6.72 (m, 3H), 7.15-7.19 (m, 1H), 7.36 (d, J=8 Hz, 1H), 7.53-7.59 (m, 3H); $^{13}$C NMR (50 MHz, CDCl$_3$) δ 40.3, 55.4, 104.1, 112.4, 113.2, 114.6, 122.6, 124.4, 127.3, 131.7, 140.1, 143.5, 150.2, 154.4.

Example 15

Preparation of 2-[4-(N,N-dimethylamino)phenyl]-6-methoxybenzothiophene (1-15)

2-[4-(N,N-Dimethylamino)phenyl]-6-methoxybenzothiophene (1-15, 100 mg, 86%) was prepared in the same manner as in Example 14 using 2-(4-aminophenyl)-6-methoxybenzothiophene (1-8, 100 mg, 0.40 mmol) obtained in Example 8, p-formaldehyde $(CH_2O)_n$, (120 mg, 4.00 mmol) and sodium cyanoborohydride (Na(CN)BH$_3$ (72 mg, 1.17 mmol). The obtained target compound 1-15 had a melting point of 130-133° C., and the following physical data;

$^1$H NMR (400 MHz, CDCl$_3$) δ 3.00 (s, 6H), 3.87 (s, 3H), 6.74 (d, J=8.8 Hz, 2H), 6.94 (dd, J=6.0, 2.8 Hz, 1H) 7.26 (d, J=8 Hz, 2H), 7.54-7.59 (m, 3H); $^{13}$C NMR (100 MHz, CDCl$_3$) δ 40.44, 55.43, 104.07, 112.31, 113.18, 114.53, 122.55, 124.30, 127.19, 131.65, 140.06, 143.45, 150.17, 154.28.

Examples 16-17

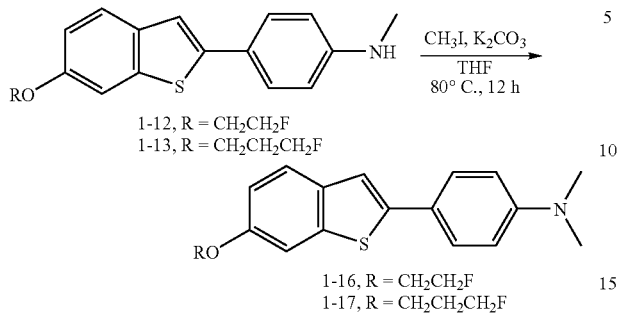

1-12, R = CH₂CH₂F
1-13, R = CH₂CH₂CH₂F 1-16, R = CH₂CH₂F
1-17, R = CH₂CH₂CH₂F

Example 16

Preparation of 2-[4-(N,N-dimethylamino)phenyl]-6-(2-fluoroethoxy)benzothiophene (1-16)

Potassium carbonate (35 mg, 0.245 mmol) and iodomethane (CH₃I, 21 μL, 0.330 mmol) were added to an anhydrous tetrahydrofuran (5 mL) solution having the 2-[4-(N-monomethylamino)phenyl]-6-(2-fluoroethoxy)benzothiophene (1-12, 50 mg, 0.165 mmol) prepared in Example 12 dissolved therein, and stirred at 80° C. for 12 hours. The reaction mixture was cooled to room temperature and water was added. Organic compounds were extracted with ethyl acetate and evaporated after a treatment with sodium sulfate. Purification was performed by column chromatograph to give the target compound 2-[4-(N,N-dimethylamino)phenyl]-6-(2-fluoroethoxy)benzothiophene (1-16, 24 mg, 46%). The obtained target compound 1-16 had a melting point of 183.9-195.9° C., and the following physical data;

$^1$H NMR (200 MHz, CDCl₃) δ 3.00 (s, 6H), 4.27 (dt, J=27.8, 4.2 Hz, 2H), 4.78 (dt, J=47.2, 4.2 Hz, 2H), 6.28 (dd, J=8.6, 2.4 Hz, 1H), 6.74 (d, J=8.8 Hz, 1H), 7.28-7.30 (m, 2H), 7.52-7.62 (m, 3H); $^{13}$C NMR (100 MHz, CDCl₃) δ 40.6, 67.6 (d, J=20.4 Hz), 81.9 (d, J=169.0 Hz), 106.1, 112.5, 114.5, 116.2, 123.5, 127.0, 135.5, 140.0, 142.8, 149.9, 155.4.

Example 17

Preparation of 2-[4-(N,N-dimethylamino)phenyl]-6-(3-fluoropropoxy)benzothiophene (1-17)

2-[4-(N,N-Dimethylamino)phenyl]-6-(3-fluoropropoxy)benzothiophene (1-17, 89 mg, 71%) was prepared in the same manner as in Example 16 using 2-[4-(N-monomethylamino)phenyl]-6-(3-fluoropropoxy)benzothiophene (1-13, 120 mg, 0.380 mmol) obtained in Example 13. The obtained target compound 1-17 had a melting point of 177.7-183.0° C., and the following physical data;

$^1$H NMR (400 MHz, CDCl₃) δ 2.16-2.25 (m, 2H), 3.00 (s, 6H), 4.16 (t, J=6.2 Hz, 2H), 4.68 (dt, J=46.8, 5.8 Hz, 2H), 6.75 (d, J=8.8 Hz, 2H), 6.95 (dd, J=8.6, 2.2 Hz, 1H), 7.28 (s, 1H), 7.29 (d, J=2.4 Hz, 1H), 7.56 (d, J=8.8 Hz, 2H), 7.58 (d, J=8.8 Hz, 1H); $^{13}$C NMR (100 MHz, CDCl₃) δ 30.5 (d, J=20.5 Hz), 40.4, 64.0 (d, J=5.3 Hz), 80.7 (d, J=163.0 Hz), 105.8, 112.3, 114.3, 116.1, 123.4, 127.0, 135.2, 140.0, 150.6, 155.8.

Preparation Examples 12-14

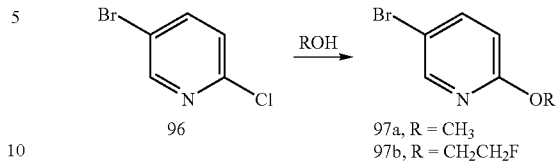

96

97a, R = CH₃
97b, R = CH₂CH₂F
97c, R = CH₂CH₂CH₂F

Preparation Example 12

Preparation of 2-methoxy-5-bromopyridine (97a)

A 0.5 M sodium methoxide methanol solution (NaOMe in MeOH, 10.4 mL, 5.19 mmol) was added to 5-bromo-2-chloropyridine (96, 500 mg, 2.59 mmol) dissolved in methanol (10 mL) at room temperature, stirred at 90° C. for 24 hours, followed by adding water. Organic compounds were extracted with ethyl acetate and evaporated after a treatment with sodium sulfate. Purification was performed by column chromatograph to give the target compound 2-methoxy-5-bromopyridine (97a, 160 mg, 33%).

$^1$H NMR (400 MHz, CDCl₃) δ 3.98 (s, 3H), 6.39 (d, J=2.4 Hz, 1H), 7.47 (dd, J=8.8, 2.4 Hz, 1H), 8.16 (d, J=2.4 Hz, 1H); $^{13}$C NMR (100 MHz, CDCl₃) δ 14.1, 53.5, 60.3, 111.6, 112.5, 140.9, 147.4, 162.9.

Preparation Example 13

Preparation of 2-(2-fluoroethoxy)-5-bromopyridine (97b)

2-Fluoroethanol (259 mg, 3.90 mmol) was added to a solution of anhydrous tetrahydrofuran (10 mL) containing sodium hydride (NaH 60%, 94 mg, 3.90 mmol) under nitrogen, stirred for 5 minutes, and 5-bromo-2-chloropyridine (96, 500 mg, 2.59 mmol) was added thereto and stirred at room temperature for 3 hours. Water was added to the reaction mixture and organic compounds were extracted with ethyl acetate and evaporated after a treatment with sodium sulfate. Purification was performed by column chromatograph to give the target compound 2-(2-fluoroethoxy)-5-bromopyridine (97b, 230 mg, 40%).

$^1$H NMR (400 MHz, CDCl₃,) δ 4.53 (dt, J=28.8, 4.0 Hz, 2H), 4.73 (dt, J=48.0, 4.0 Hz, 2H), 6.72 (d, J=8.8 Hz, 1H), 7.65 (dd, J=8.4, 2.4 Hz, 1H), 8.16 (d, J=2.8 Hz, 1H); $^{13}$C NMR (100 MHz, CDCl₃,) δ 70.4 (d, J=27.0 Hz), 83.1 (d, J=160.0 Hz), 97.3, 111.9, 112.9, 141.1, 147.3.

Preparation Example 14

Preparation of 2-(3-fluoropropoxy)-5-bromopyridine (97c)

2-(3-Fluoropropoxy)-5-bromopyridine (97c, 600 mg, 98%) was prepared in the same manner as in Preparation Example 13 using sodium hydride (94 mg, 3.90 mmol), 3-fluoropropanol (305 mg, 3.90 mmol) and 5-bromo-2-chloropyridine (96, 500 mg, 2.60 mmol).

$^1$H NMR (400 MHz, CDCl₃) δ 2.09-2.21 (m, 2H), 4.39 (t, J=5.8 Hz, 2H), 4.62 (dt, J=46.8, 5.8 Hz, 2H), 6.63 (d, J=8.8 Hz, 1H), 7.62 (dd, J=8.4, 2.4 Hz, 1H), 8.19 (d, J=2.8 Hz, 1H);

$^{13}$C NMR (100 MHz, CDCl$_3$) δ 30.97 (d, J=19.7 Hz), 62.77 (d, J=6.1 Hz), 81.6 (d, J=161.4 Hz), 111.7, 112.6, 141.0, 147.4, 162.4.

Preparation Example 15

Preparation of 2-(N,N-dimethylamino)-5-iodopyridine

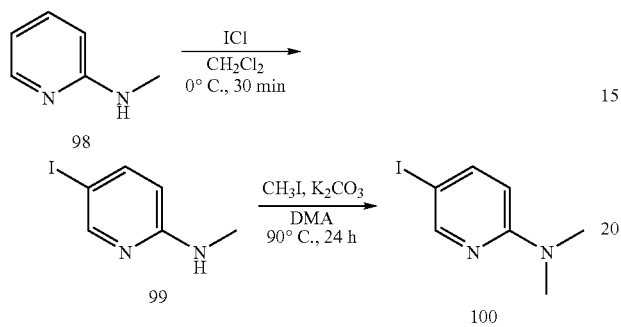

2-(N-Monomethylamino)pyridine (98, 1.00 g, 5.55 mmol) was dissolved in dichloromethane (20 mL) and a 1 M iodine monochloride (ICl, 6.10 mL, 6.10 mmol) dichloromethane solution was slowly added at 0° C., and stirred for 30 minutes. To the reaction mixture was added a 10% aqueous solution of sodium sulfite (Na$_2$S$_2$O$_3$) and organic compounds were extracted with dichloromethane and evaporated after a treatment with sodium sulfate. Purification was performed by column chromatograph to give the target compound 2-(N-monomethylamino)-5-iodopyridine (99, 800 mg, 62%) as a yellow solid.

$^1$H NMR (400 MHz, CDCl$_3$) δ 2.88 (s, 3H), 4.57 (s, 1H), 6.24 (d, J=8.4 Hz, 1H), 7.62 (dd, J=8.8, 2.4 Hz, 1H), 8.23 (d, J=2.4 Hz, 1H); $^{13}$C NMR (100 MHz, CDCl$_3$) δ 28.9, 76.2, 108.5, 144.8, 153.8, 158.3

The obtained 2-(N-monomethylamino)-5-iodopyridine (99, 1.00 g, 4.27 mmol), potassium carbonate (2.95 g, 21.36 mmol) and iodomethane (145 mg, 8.546 mmol) were dissolved in dimethylacetamide (30 mL), and the reaction mixture was heated at 90° C. for 24 hours, followed by adding water. Organic compounds were extracted with ethyl acetate and evaporated after a treatment with sodium sulfate. Purification was performed by column chromatograph to give the target compound 2-(N,N-dimethylamino)-5-iodopyridine (100, 603 mg, 57%).

$^1$H NMR (400 MHz, CDCl$_3$) δ 3.08 (s, 6H), 6.34 (d, J=8.4 Hz, 1H), 7.60 (dd, J=8.8, 2.4 Hz, 1H), 8.27 (d, J=2.4 Hz, 1H); $^{13}$C NMR (100 MHz, CDCl$_3$) δ 38.1, 105.9, 107.1, 139.2, 148.3, 157.7.

Examples 18-26

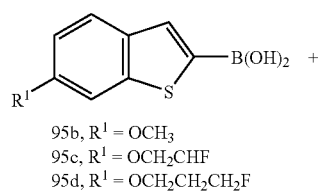

95b, R$^1$ = OCH$_3$
95c, R$^1$ = OCH$_2$CHF
95d, R$^1$ = OCH$_2$CH$_2$F

-continued

97a, HaI = Br, R$^2$ = OCH$_3$
97b, HaI = Br, R$^2$ = OCH$_2$CH$_2$F
97c, HaI = BrR$^2$ = OCH$_2$CH$_2$CH$_2$F
99, HaI = I, R$^2$ = NH(CH$_3$)
100, HaI = I, R$^2$ = N(CH$_3$)$_2$
101, HaI = I, R$^2$ = NH$_2$ 1-18, R$^1$ = OCH$_3$, R$^2$ = OCH$_2$CH$_2$F
1-19, R$^1$ = OCH$_3$, R$^2$ = OCH$_2$CH$_2$CH$_2$F
1-20, R$^1$ = OCH$_2$CH$_2$F, R$^2$ = OCH$_3$
1-21, R$^1$ = OCH$_2$CH$_2$F, R$^2$ = NH$_2$
1-22, R$^1$ = OCH$_2$CH$_2$F, R$^2$ = NH(CH$_3$)
1-23, R$^1$ = OCH$_2$CH$_2$F, R$^2$ = N(CH$_3$)$_2$
1-24, R$^1$ = OCH$_2$CH$_2$CH$_2$F, R$^2$ = NH$_2$
1-25, R$^1$ = OCH$_2$CH$_2$CH$_2$F, R$^2$ = NH(CH$_3$)
1-26, R$^1$ = OCH$_2$CH$_2$CH$_2$F, R$^2$ = N(CH$_3$)$_2$

Example 18

Preparation of 2-[2-(2-fluoroethoxy)pyridine-5-yl]-6-methoxybenzothiophene (1-18)

2-[2-(2-Fluoroethoxy)pyridine-5-yl]-6-methoxybenzothiophene (1-18, 74 mg, 78%) was prepared in the same manner as in Example 1 using 6-methoxy benzothiophene-2-boronic acid (95b, 80 mg, 0.385 mmol) obtained in Preparation Example 8 and 2-(2-fluoroethoxy)-5-bromopyridine (97b, 77 mg, 0.350 mmol) obtained in Preparation Example 13.

$^1$H NMR (400 MHz, CDCl$_3$) δ 3.87 (s, 3H), 4.61 (dt, J=28.8, 4.4 Hz, 2H), 4.77 (dt, J=47.6, 4.0 Hz, 2H), 6.85 (d, J=8.4 Hz, 1H), 6.98 (dd, J=8.8, 2.4 Hz, 1H), 7.29 (d, J=2.0 Hz, 1H), 7.34 (s, 1H), 7.63 (d, J=8.8 Hz, 1H), 7.85 (dd, J=8.8, 2.4 Hz, 1H), 8.42 (d, J=2.4 Hz, 1H); $^{13}$C NMR (100 MHz, CDCl$_3$) δ 56.1, 65.5 (d, J=19.7 Hz), 81.5 (d, J=168.2 Hz), 105.3, 111.8, 115.1, 119.3, 124.5, 125.0, 134.9, 137.1, 138.1, 141.2, 144.4, 157.9, 163.1.

Example 19

Preparation of 2-[2-(3-fluoropropoxy)pyridine-5-yl]-6-methoxybenzothiophene (1-19)

2-[2-(3-Fluoropropoxy)pyridine-5-yl]-6-methoxybenzothiophene (1-19, 54 mg, 49%) was prepared in the same manner as in Example 1 using 6-methoxybenzothiophene-2-boronic acid (95b, 80 mg, 0.385 mmol) obtained in Preparation Example 8 and 2-(3-fluoropropoxy)-5-bromopyridine (97c, 82 mg, 0.350 mmol) obtained in Preparation Example 14.

$^1$H NMR (400 MHz, acetone-d$_6$) δ 2.13-2.22 (dm, J=25.2 Hz, 2H), 3.88 (s, 3H), 4.47 (t, J=6.4 Hz, 2H), 4.64 (dt, J=47.2, 6.0 Hz, 2H), 6.85 (d, J=8.8 Hz, 1H), 7.00 (dd, J=8.8, 2.4 Hz, 1H), 7.47 (d, J=2.4 Hz, 1H), 7.58 (s, 1H), 7.70 (d, J=8.8 Hz, 1H), 7.99 (dd, J=8.4, 2.4 Hz, 1H), 8.47 (d, J=2.4 Hz, 1H); $^{13}$C NMR (100 MHz, acetone-d$_6$) δ 30.97 (d, J=19.7 Hz), 55.9, 62.77 (d, J=6.1 Hz), 81.6 (d, J=161.4 Hz), 101.5, 105.6, 111.9, 115.5, 120.0, 125.0, 135.5, 137.2, 138.2, 141.5, 144.7, 158.6, 164.0.

Example 20

Preparation of 2-(2-methoxypyridine-5-yl)-6-(2-fluoroethoxy)benzothiophene (1-20)

2-(2-Methoxypyridine-5-yl)-6-(2-fluoroethoxy)benzothiophene (1-20, 36 mg, 29%) was prepared in the same manner as in Example 1 using 6-(2-fluoroethoxy)benzothiophene-2-boronic acid (95c, 100 mg, 0.417 mmol) obtained in Preparation Example 9 and 2-methoxy-5-bromopyridine (97a, 78 mg, 0.379 mmol) obtained in Preparation Example 12.
$^1$H NMR (400 MHz, CDCl$_3$) δ 3.98 (s, 3H), 4.29 (dt, J=27.6, 4.0 Hz, 2H), 4.79 (dt, J=47.6, 4.4 Hz, 2H), 6.80 (d, J=8.4 Hz, 1H), 7.02 (dd, J=8.8, 2.4 Hz, 1H), 7.31 (d, J=2.0 Hz, 1H), 7.36 (s, 1H), 7.66 (d, J=8.4 Hz, 1H), 7.84 (dd, J=8.8, 2.8 Hz, 1H), 8.47 (d, J=2.4 Hz, 1H); $^{13}$C NMR (100 MHz, CDCl$_3$) δ 53.6, 67.5 (d, J=20.4 Hz), 81.7 (d, J=169.8 Hz), 105.8, 110.9, 114.8, 118.5, 123.8, 124.0, 134.9, 136.3, 138.2, 140.4, 144.0, 155.9, 163.5.

Example 21

Preparation of 2-(2-aminopyridine-5-yl)-6-(2-fluoroethoxy)benzothiophene (1-21)

2-(2-Aminopyridine-5-yl)-6-(2-fluoroethoxy)benzothiophene (1-21, 39 mg, 33%) was prepared in the same manner as in Example 1 using 6-(2-fluoroethoxy)benzothiophene-2-boronic acid (95c, 101 mg, 0.421 mmol) obtained in Preparation Example 9 and 2-amino-5-iodopyridine (101, 84 mg, 0.383 mmol).
$^1$H NMR (400 MHz, THF-d$_8$) δ 4.26 (dt, J=28.4, 4.0 Hz, 2H), 4.71 (dt, J=48.0, 4.0 Hz, 2H), 5.61 (brs, 2H), 6.46 (d, J=8.8 Hz, 1H), 6.96 (dd, J=8.8 Hz, 1H), 7.33 (s, 1H), 7.39 (d, J=2.0 Hz, 1H), 7.58 (d, J=8.8 Hz, 1H), 7.65 (dd, J=8.4, 2.4 Hz, 1H), 8.31 (s, 1H); $^{13}$C NMR (100 MHz, THF-d$_8$) δ 68.7 (d, J=19.7 Hz), 82.8 (d, J=168.3 Hz), 106.6, 108.5, 115.5, 117.5, 120.4, 124.4, 135.3, 136.3, 140.7, 141.0, 146.6, 157.2, 160.5.

Example 22

Preparation of 2-[2-(N-monomethylamino)pyridine-5-yl]-6-(2-fluoroethoxy)benzothiophene (1-22)

2-[2-(N-Monomethylamino)pyridine-5-yl]-6-(2-fluoroethoxy)benzothiophene (1-22, 56 mg, 49%) was prepared in the same manner as in Example 1 using 6-(2-fluoroethoxy)benzothiophene-2-boronic acid (95c, 102 mg, 0.425 mmol) obtained in Preparation Example 9 and 2-(N-monomethylamino)-5-iodopyridine (99, 90 mg, 0.384 mmol) obtained in Preparation Example 15.
$^1$H NMR (400 MHz, THF-d$_8$) δ 2.89 (d, J=4.8 Hz, 3H), 4.25 (dt, J=28.4, 4.4 Hz, 2H), 4.71 (dt, J=48.0, 4.4 Hz, 2H), 5.94 (brd, J=4 Hz, 1H), 6.41 (d, J=8.8 Hz, 1H), 6.95 (dd, J=8.4, 2.4 Hz, 1H), 7.32 (s, 1H), 7.38 (d, J=2.0 Hz, 1H), 7.57 (d, J=8.8 Hz, 1H), 7.65 (dd, J=8.8, 2.4 Hz, 1H), 8.37 (d, J=2.4 Hz, 1H); $^{13}$C NMR (100 MHz, THF-d$_8$) δ 28.9, 68.7 (d, J=20.5 Hz), 82.8 (d, J=169.1 Hz), 106.6, 107.7, 115.5, 117.3, 119.8, 124.3, 134.9, 136.4, 140.8, 141.0, 146.6, 157.1, 160.4.

Example 23

Preparation of 2-[2-(N,N-dimethylamino)pyridine-5-yl]-6-(2-fluoroethoxy)benzothiophene (1-23)

2-[2-(N,N-Dimethylamino)pyridine-5-yl]-6-(2-fluoroethoxy)benzothiophene (1-23, 61 mg, 51%) was prepared in the same manner as in Example 1 using 6-(2-fluoroethoxy)benzothiophene-2-boronic acid (95c, 101 mg, 0.421 mmol) obtained in Preparation Example 9 and 2-(N,N-dimethylamino)-5-iodopyridine (100, 95 mg, 0.383 mmol) obtained in Preparation Example 15.
$^1$H NMR (400 MHz, CDCl$_3$) δ 3.13 (s, 6H), 4.27 (dt, J=28.0, 4.4 Hz, 2H), 4.78 (dt, J=47.2, 4.0 Hz, 2H), 6.54 (d, J=8.8 Hz, 1H), 6.99 (dd, J=8.4, 2.4 Hz, 1H), 7.26 (s, 1H), 7.29 (d, J=2.0 Hz, 1H), 7.60 (d, J=8.8 Hz, 1H), 7.70 (dd, J=8.8, 2.4 Hz, 1H), 8.49 (d, J=2.4 Hz, 1H); $^{13}$C NMR (100 MHz, CDCl$_3$) δ 38.7, 68.1 (d, J=20.5 Hz), 82.45 (d, J=169.0 Hz) 106.0, 106.6, 115.1, 117.1, 118.9, 124.1, 135.3, 135.8, 140.3, 140.5, 146.0, 156.1, 159.0.

Example 24

Preparation of 2-(2-aminopyridine-5-yl)-6-(3-fluoropropoxy)benzothiophene (1-24)

2-(2-Aminopyridine-5-yl)-6-(3-fluoropropoxy)benzothiophene (1-24, 53 mg, 58%) was prepared in the same manner as in Example 1 using 6-(3-fluoropropoxy)benzothiophene-2-boronic acid (95d, 80 mg, 0.315 mmol) obtained in Preparation Example 10 and 2-amino-5-iodopyridine (101, 63 mg, 0.286 mmol).
$^1$H NMR (400 MHz, acetone-d$_6$) δ 2.13-2.25 (dm, J=25.2, 2H), 4.18 (t, J=6.4 Hz, 2H), 4.66 (dt, J=47.2, 6.0 Hz, 2H), 5.71 (brs, 2H), 6.63 (d, J=8.4 Hz, 1H), 6.99 (dd, J=8.4, 2.4 Hz, 1H), 7.43 (s, 1H), 7.46 (d, J=2.4 Hz, 1H), 7.65 (d, J=8.8 Hz, 1H), 7.74 (dd, J=8.4, 2.4 Hz, 1H), 8.34 (d, J=2.4 Hz, 1H); $^{13}$C NMR (100 MHz, acetone-d$_6$) δ 31.2 (d, J=19.7 Hz), 64.8 (d, J=6.1 Hz), 81.4 (d, J=161.4 Hz), 106.6, 108.9, 115.5, 117.8, 120.5, 124.5, 135.5, 135.9, 140.1, 140.8, 146.2, 157.2, 160.2.

Example 25

Preparation of 2-[2-(N-monomethylamino)pyridine-5-yl]-6-(3-fluoropropoxy)benzothiophene (1-25)

2-[2-(N-Monomethylamino)pyridine-5-yl]-6-(3-fluoropropoxy)benzothiophene (25, 36 mg, 39%) was prepared in the same manner as in Example 1 using 6-(3-fluoropropoxy)benzothiophene-2-boronic acid (95d, 80 mg, 0.315 mmol) obtained in Preparation Example 10 and 2-(N-monomethylamino)-5-iodopyridine (99, 67 mg, 0.286 mmol) obtained in Preparation Example 15.
$^1$H NMR (400 MHz, CDCl$_3$) δ 2.14-2.64 (dm, J=25.6 Hz, 2H), 2.96 (d, J=5.2 Hz, 3H), 4.15 (t, J=6.0 Hz, 2H), 4.61 (t, J=6.0 Hz, 1H), 4.73 (t, J=5.6 Hz, 2H), 6.42 (d, J=8.8 Hz, 1H), 6.95 (dd, J=8.4, 2.0 Hz, 1H), 7.26 (s, 1H), 7.28 (d, J=2.0 Hz, 1H), 7.59 (d, J=8.8 Hz, 1H), 7.70 (dd, J=8.4, 2.4 Hz, 1H), 8.42 (d, J=2.0 Hz, 1H); $^{13}$C NMR (100 MHz, CDCl$_3$) δ 29.7, 31.0 (d, J=10.5 Hz), 64.5 (d, J=5.3 Hz), 81.2 (d, J=163.0 Hz), 106.3, 106.5, 115.1, 117.5, 120.5, 124.1, 135.4, 135.7, 139.7, 140.6, 146.2, 156.6, 159.3.

Example 26

Preparation of 2-[2-(N,N-dimethylamino)pyridine-5-yl]-6-(3-fluoropropoxy)benzothiophene (1-26)

2-[2-(N,N-Dimethylamino)pyridine-5-yl]-6-(3-fluoropropoxy)benzothiophene (1-26, 34 mg, 36%) was prepared in the same manner as in Example 1 using 6-(3-fluoropropoxy)benzothiophene-2-boronic acid (95d, 80 mg, 0.315 mmol)

obtained in Preparation Example 10 and 2-(N,N-dimethylamino)-5-iodopyridine (100, 71 mg, 0.286 mmol) obtained in Preparation Example 15

$^1$H NMR (400 MHz, CDCl$_3$) δ 2.14-2.26 (dm, J=26.0 Hz, 2H), 3.13 (s, 6H), 4.15 (t, J=6.0 Hz, 2H), 4.67 (dt, J=46.8, 5.6 Hz, 2H), 6.54 (d, J=8.8 Hz, 1H), 6.95 (dd, J=8.8, 2.4 Hz, 1H), 7.25 (s, 1H), 7.287 (d, J=2.4 Hz, 1H), 7.32 (d, J=8.4 Hz, 1H), 7.70 (dd, J=8.8, 2.4 Hz, 1H), 8.49 (d, J=2.4 Hz, 1H); $^{13}$C NMR (100 MHz, CDCl$_3$) δ 30.7 (d, J=20.4 Hz), 38.4, 64.2 (d, J=21.2 Hz), 80.9 (d, J=163.0 Hz), 105.7, 106.0, 114.7, 116.8, 118.7, 123.7, 135.0, 135.2, 139.7, 140.3, 145.6, 156.2, 158.7.

Preparation Examples 16-18

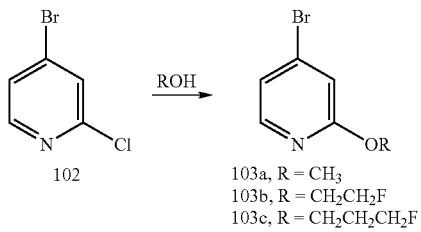

Preparation Example 16

Preparation of 2-methoxy-4-bromopyridine (103a)

2-Methoxy-4-bromopyridine (103a, 192 mg, 98%) was prepared in the same manner as in Preparation Example 12 except that 4-bromo-2-chloropyridine, instead of 5-bromo-2-chloropyridine, was used.

$^1$H NMR (400 MHz, CDCl$_3$) δ 3.85 (s, 3H), 6.75 (dd, J=6.0, 2.4 Hz), 6.83 (d, J=2.0, 1H), 8.18 (d, J=6.0 Hz, 1H); $^{13}$C NMR (100 MHz, CDCl$_3$) δ 55.4, 109.29, 109.56, 150.0, 152.4, 167.1.

Preparation Example 17

Preparation of 2-(2-fluoroethoxy)-4-bromopyridine (103b)

2-(2-Fluoroethoxy)-4-bromopyridine (103b, 185 mg, 81%) was prepared in the same manner as in Preparation Example 12 except that 4-bromo-2-chloropyridine, instead of 5-bromo-2-chloropyridine, was used.

$^1$H NMR (400 MHz, CDCl$_3$) δ 4.27 (dt, J=27.6, 3.6, 2H), 4.77 (dt, J=47.2, 3.6 Hz, 1H), 6.79 (dd, J=5.2, 2.0, 1H), 6.87 (d, J=2.0, 1H), 8.22 (d, J=6.0 Hz, 1H); $^{13}$C NMR (100 MHz, CDCl$_3$) δ 67.3 (d, J=20.5 Hz), 81.1 (d, J=171.3 Hz), 109.9, 110.0, 150.4, 152.7, 166.1.

Preparation Example 18

Preparation of 2-(3-fluoroethoxy)-4-bromopyridine (103c)

2-(3-Fluoroethoxy)-4-bromopyridine (103c, 190 mg, 78%) was prepared in the same manner as in Preparation Example 12 except that 4-bromo-2-chloropyridine, instead of 5-bromo-2-chloropyridine, was used.

$^1$H NMR (400 MHz, CDCl$_3$) δ 2.16 (dq, J=25.6, 6.0 Hz, 2H), 4.43 (t, J=6.0 Hz, 2H), 4.61 (dt, J=46.8, 6.0 Hz, 1H), 6.95 (d, J=1.2, 1H), 7.02 (dd, J=5.2, 1.6 Hz, 1H), 7.97 (d, J=6.4 Hz, 1H); $^{13}$C NMR (100 MHz, CDCl$_3$) δ 30.1 (d, J=19.7 Hz), 62.2 (d, J=6.0 Hz), 80.8 (d, J=163.7 Hz), 114.3, 120.4, 133.8, 147.5, 164.3.

Examples 27-30

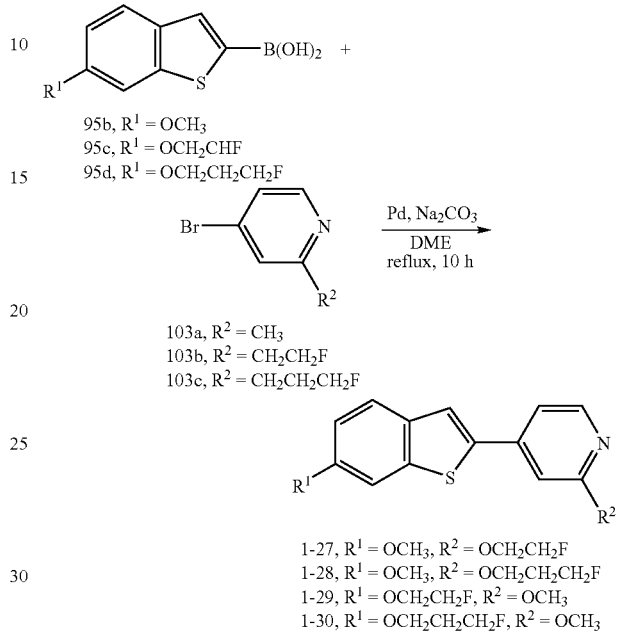

Example 27

Preparation of 2-[2-(2-fluoroethoxy)pyridine-4-yl]-6-methoxybenzothiophene (1-27)

2-[2-(2-Fluoroethoxy)pyridine-4-yl]-6-methoxybenzothiophene (1-27, 20 mg, 30%) was prepared in the same manner as in Example 1 as a yellow solid using 6-methoxybenzothiophene-2-boronic acid (95b, 50 mg, 0.24 mmol) obtained in Preparation Example 8 and 2-(2-fluoroethoxy)-4-bromopyridine (103b, 48 mg, 0.22 mmol) obtained in Preparation Example 17.

$^1$H NMR (400 MHz, acetone-d$_6$) δ 3.89 (s, 3H), 4.50 (dt, J=29.2, 4.0 Hz, 2H), 4.84 (dt, J=47.6, 4.0 Hz, 2H), 6.90 (dd, J=5.6, 2.4 Hz, 1H), 7.00 (dd, J=8.8, 2.4 Hz, 1H), 7.49 (d, J=2.4 Hz, 1H), 7.58 (d, J=2.4 Hz, 1H), 7.73 (d, J=8.8 Hz, 1H), 7.99 (s, 1H), 8.38 (d, J=5.6 Hz, 1H); $^{13}$C NMR (100 MHz, acetone-d$_6$) δ 56.0, 68.4 (d, J=19.7 Hz), 82.6 (d, J=167.5 Hz), 101.6, 105.5, 105.8, 110.2, 115.6, 121.9, 125.6, 135.3, 143.3, 151.5, 155.1, 159.1, 166.1.

Example 28

Preparation of 2-[2-(3-fluoropropoxy)pyridine-4-yl]-6-methoxybenzothiophene (1-28)

2-[2-(3-Fluoropropoxy)pyridine-4-yl]-6-methoxybenzothiophene (1-28, 25 mg, 23%) was prepared in the same manner as in Example 1 as a yellow solid using 6-methoxybenzothiophene-2-boronic acid (95b, 80 mg, 0.38 mmol) obtained in Preparation Example 8 and 2-(3-fluoropropoxy)-4-bromopyridine (103c, 82 mg, 0.35 mmol) obtained in Preparation Example 18.

$^1$H NMR (200 MHz, acetone-$d_6$) δ 2.10-2.35 (m, 2H), 3.89 (s, 1H), 4.32 (t, J=6.4 Hz, 2H), 4.67 (dt, J=47.2, 5.8 Hz, 2H), 6.87 (dd, J=5.8, 2.6 Hz, 1H), 6.99 (dd, J=8.8, 2.2 Hz, 1H), 7.48 (d, J=2.4 Hz, 1H), 7.56 (d, J=2.2 Hz, 1H), 7.72 (d, J=8.6 Hz, 1H), 7.98 (s, 1H), 8.36 (d, J=5.8 Hz, 1H); $^{13}$C NMR (100 MHz, acetone-$d_6$) δ 30.9 (d, J=19.7 Hz), 55.9, 64.9 (d, J=5.3 Hz), 81.3 (d, J=161.4 Hz), 101.6, 105.5, 105.7, 110.3, 115.6, 121.8, 125.6, 135.3, 143.3, 151.4, 155.0, 159.1, 166.3.

Example 29

Preparation of 2-(2-methoxypyridine-4-yl)-6-(2-fluoroethoxy)benzothiophene (1-29)

2-(2-Methoxypyridine-4-yl)-6-(2-fluoroethoxy)benzothiophene (1-29, 40 mg, 44%) was prepared in the same manner as in Example 1 as a yellow solid using 6-(2-fluoroethoxy)benzothiophene-2-boronic acid (95c, 80 mg, 0.33 mmol) obtained in Preparation Example 9 and 2-methoxy-4-bromopyridine (103a, 82 mg, 0.35 mmol) obtained in Preparation Example 16.

$^1$H NMR (400 MHz, acetone-$d_6$) δ 3.97 (s, 3H), 4.38 (dt, J=29.2, 4.0 Hz, 2H), 4.82 (dt, J=47.6, 4.0 Hz, 2H), 6.86 (dd, J=5.6, 2.4 Hz, 1H), 7.04 (dd, J=8.8, 2.4 Hz, 1H), 7.52 (d, J=2.4 Hz, 1H), 7.54 (d, J=2.4 Hz, 1H), 7.75 (d, J=8.4 Hz, 1H), 7.98 (s, 1H), 8.37 (d, J=5.6 Hz, 1H); $^{13}$C NMR (100 MHz, acetone-$d_6$) δ 55.9, 68.6 (d, J=19.7 Hz), 82.9 (d, J=166.7 Hz), 101.6, 105.3, 106.5, 110.0, 115.9, 121.7, 125.8, 135.7, 143.2, 151.4, 154.9, 157.9, 167.2.

Example 30

Preparation of 2-(2-methoxypyridine-4-yl)-6-(3-fluoropropoxy)benzothiophene (1-30)

2-(2-Methoxypyridine-4-yl)-6-(3-fluoropropoxy)benzothiophene (1-30, 10 mg, 10%) was prepared in the same manner as in Example 1 as a yellow solid using 6-(3-fluoropropoxy)benzothiophene-2-boronic acid (95d, 90 mg, 0.35 mmol) obtained in Preparation Example 10 and 2-methoxy-4-bromopyridine (103a, 60 mg, 0.32 mmol) obtained in Preparation Example 16.

$^1$H NMR (400 MHz, acetone-$d_6$) δ 2.15-2.27 (m, 2H), 3.97 (s, 1H), 4.23 (t, J=6.4 Hz, 2H), 4.68 (dt, J=47.2, 6.0 Hz, 2H), 6.86 (dd, J=5.6, 2.4 Hz, 1H), 7.02 (dd, J=8.8, 2.4 Hz, 1H), 7.51 (d, J=2.4 Hz, 1H), 7.53 (d, J=2.4 Hz, 1H), 7.74 (d, J=8.4 Hz, 1H), 7.97 (s, 1H), 8.36 (d, J=5.6 Hz, 1H); $^{13}$C NMR (100 MHz, acetone-$d_6$) δ 31.2 (d, J=19.7 Hz), 55.9, 64.9 (d, J=6.1 Hz), 81.5 (d, J=161.4 Hz), 101.6, 105.3, 106.4, 109.9, 115.8, 121.7, 125.7, 135.5, 143.3, 151.4, 154.9, 158.2, 167.2.

Preparation Examples 19-21

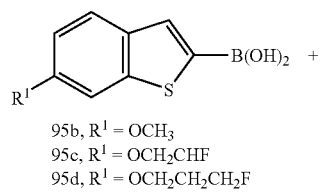

95b, R$^1$ = OCH$_3$
95c, R$^1$ = OCH$_2$CHF
95d, R$^1$ = OCH$_2$CH$_2$CH$_2$F

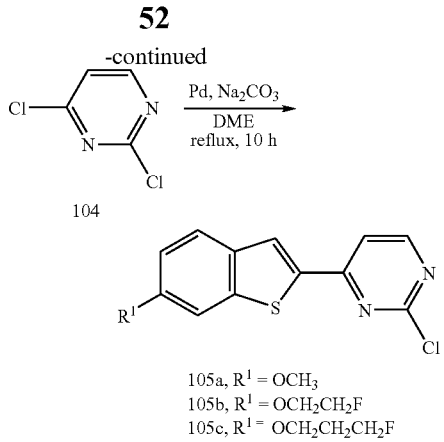

105a, R$^1$ = OCH$_3$
105b, R$^1$ = OCH$_2$CH$_2$F
105c, R$^1$ = OCH$_2$CH$_2$CH$_2$F

Preparation Example 19

Preparation of 2-(2-chloropyrimidine-4-yl)-6-methoxybenzothiophene (105a)

2-(2-Chloropyrimidine-4-yl)-6-methoxybenzothiophene (105a, 365 mg, 55%) was prepared in the same manner as in Example 1 using 6-methoxybenzothiophene-2-boronic acid (95b, 500 mg, 2.40 mmol) obtained in Preparation Example 8 and 2,6-dichloropyrimidine (104, 394 mg, 2.64 mmol).

$^1$H NMR (400 MHz, THF-$d_8$) δ 3.88 (s, 3H), 7.00 (dd, J=8.8, 2.4 Hz, 1H), 7.48 (d, J=2.4, 1H), 7.75 (d, J=8.8 Hz, 1H), 7.81 (d, J=5.2 Hz, 1H), 8.18 (s, 1H), 8.58 (d, J=5.2 Hz, 1H); $^{13}$C NMR (100 MHz, THF-$d_8$) δ 56.0, 105.5, 115.1, 116.9, 126.7, 127.4, 135.0, 138.7, 145.0, 160.72, 160.77, 162.6, 163.4.

Preparation Example 20

Preparation of 2-(2-chloropyrimidine-4-yl)-6-(2-fluoroethoxy)benzothiophene (105b)

2-(2-Chloropyrimidine-4-yl)-6-(2-fluoroethoxy)benzothiophene (105b, 469 mg, 73%) was prepared in the same manner as in Example 1 using 6-(2-fluoroethoxy)benzothiophene-2-boronic acid (95c, 500 mg, 2.08 mmol) obtained in Preparation Example 9 and 2,6-dichloropyrimidine (104, 341 mg, 2.29 mmol).

$^1$H NMR (200 MHz, DMSO-$d_6$) δ 4.36 (dt, J=30.0, 5.2 Hz, 2H), 4.81 (dt, J=47.6, 5.2 Hz, 2H), 7.11 (dd, J=8.8, 2.2 Hz, 1H), 7.67 (s, 1H), 7.87 (d, J=8.8 Hz, 1H), 8.12 (dd, J=5.2, 1.4 Hz, 1H), 8.45 (s, 1H), 8.76 (dd, J=5.2, 1.4 Hz, 1H); $^{13}$C NMR (50 MHz, DMSO-$d_6$) δ 67.8, 82.1 (d, J=165.4 Hz), 105.9, 114.8, 116.1, 126.3, 127.5, 133.8, 137.2, 143.0, 149.5, 157.9, 160.4, 161.8.

Preparation Example 21

Preparation of 2-(2-chloropyrimidine-4-yl)-6-(3-fluoropropoxy)benzothiophene (105c)

2-(2-Chloropyrimidine-4-yl)-6-methoxybenzothiophene (105c, 426 mg, 67%) was prepared in the same manner as in Example 1 using 6-(3-fluoropropoxy)benzothiophene-2-boronic acid (95d, 500 mg, 1.97 mmol) obtained in Preparation Example 10 and 2,6-dichloropyrimidine (104, 322 mg, 2.16 mmol).

$^1$H NMR (200 MHz, DMSO-$d_6$) δ 2.14 (dqt, J=24.6, 5.8 Hz, 2H), 4.16 (t, J=5.2 Hz, 2H), 4.62 (dt, J=48.4, 5.2 Hz, 2H), 7.05 (dd, J=8.8, 2.2 Hz, 1H), 7.62 (s, 1H), 7.81 (dd, J=8.8, 2.2 Hz, 1H), 8.07 (dd, J=5.2, 1.8 Hz, 1H), 8.39 (d, J=1.4 Hz, 1H), 8.72 (dd, J=5.0, 1.8 Hz, 1H); $^{13}$C NMR (50 MHz, DMSO-$d_6$) δ 29.7 (d, J=19.4 Hz), 64.0, 80.8 (d, J=161.3 Hz), 105.7, 114.8, 116.0, 126.2, 127.5, 133.6, 137.0, 143.1, 149.6, 158.1, 160.3, 161.8.

Examples 31-39

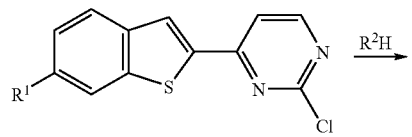

105a, R$^1$ = OCH$_3$
105b, R$^1$ = OCH$_2$CH$_2$F
105c, R$^1$ = OCH$_2$CH$_2$CH$_2$F

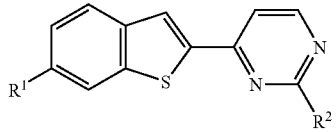

1-31, R$^1$ = OCH$_3$, R$^2$ = OCH$_2$CH$_2$F
1-32, R$^1$ = OCH$_3$, R$^2$ = OCH$_2$CH$_2$CH$_2$F
1-33, R$^1$ = OCH$_3$, R$^2$ = NH(CH$_2$CH$_2$F)
1-34, R$^1$ = OCH$_2$CH$_2$F, R$^2$ = OCH$_3$
1-35, R$^1$ = OCH$_2$CH$_2$F, R$^2$ = NH(CH$_3$)
1-36, R$^1$ = OCH$_2$CH$_2$F, R$^2$ = N(CH$_3$)$_2$
1-37, R$^1$ = OCH$_2$CH$_2$CH$_2$F, R$^2$ = OCH$_3$
1-38, R$^1$ = OCH$_2$CH$_2$CH$_2$F, R$^2$ = NH(CH$_3$)
1-39, R$^1$ = OCH$_2$CH$_2$CH$_2$F, R$^2$ = N(CH$_3$)

Example 31

Preparation of 2-[2-(2-fluoroethoxy)pyrimidine-4-yl]-6-methoxybenzothiophene (1-31)

2-Fluoroethanol (32 μL, 0.54 mmol) and sodium hydride (NaH, 22 mg, 0.54 mmol) were dissolved in a solvent of anhydrous tetrahydrofuran (4 mL) under nitrogen, and the mixture was added to a solution of anhydrous tetrahydrofuran (3 mL) containing 2-(2-chloropyrimidine-4-yl)-6-methoxybenzothiophene (105a, 100 mg, 0.36 mmol) obtained in Preparation Example 19 dissolved therein at room temperature, heated at 60° C. for 10 hours, cooled to room temperature, followed by adding water. Organic compounds were extracted with ethyl acetate and evaporated after a treatment with sodium sulfate. Column chromatography was performed to give the target compound 2-[2-(2-fluoroethoxy)pyrimidine-4-yl]-6-methoxybenzothiophene (1-31, 79 mg, 72%) as a pale yellow solid.
$^1$H NMR (400 MHz, acetone-$d_6$) δ 3.89 (s, 3H,), 4.66 (dt, J=29.2, 4.0 Hz, 2H), 4.83 (dt, J=47.6, 4.0 Hz, 2H), 7.01 (dd, J=8.8, 2.4 Hz, 1H), 7.48 (d, J=2.4 Hz, 1H), 7.53 (d, J=5.2 Hz, 1H), 7.75 (d, J=9.2 Hz, 1H), 8.12 (s, 1H), 8.52 (d, J=5.2 Hz, 1H); $^{13}$C NMR (100 MHz, acetone-$d_6$) δ 55.9, 67.3 (d, J=19 Hz), 82.5 (d, J=166 Hz), 105.3, 110.4, 116.1, 125.9, 126.4, 134.7, 139.9, 143.9, 159.8, 160.2, 162.1, 165.7.

Example 32

Preparation of 2-[2-(3-fluoropropoxy)pyrimidine-4-yl]-6-methoxybenzothiophene (1-32)

2-[2-(3-Fluoropropoxy)pyrimidine-4-yl]-6-methoxybenzothiophene (1-32, 75 mg, 65%) was prepared in the same manner as in Example 31 as a pale yellow solid using 3-fluoro-1-propanol (40 mL, 0.54 mmol), sodium hydride (NaH, 22 mg, 0.54 mmol) and 2-(2-chloropyrimidine-4-yl)-6-methoxybenzothiophene (105a, 100 mg, 0.36 mmol) obtained in Preparation Example 19.
$^1$H NMR (400 MHz, acetone-$d_6$) δ 2.16-2.29 (dm, J=25.2 Hz, 2H), 3.90 (s, 3H), 4.52 (t, J=6.4 Hz, 2H), 4.67 (dt, J=47.6, 6.0 Hz, 2H), 7.02 (dd, J=8.8, 2.4 Hz, 1H), 7.50 (d, J=2.4 Hz, 1H), 7.52 (d, J=5.2 Hz, 1H), 7.67 (d, J=8.8 Hz, 1H), 8.13 (s, 1H), 8.52 (d, J=5.6 Hz, 1H); $^{13}$C NMR (100 MHz, acetone-$d_6$) δ 30.76 (d, J=19.7 Hz), 55.9, 64.0 (d, J=5.3 Hz), 81.53 (d, J=162.2 Hz), 105.4, 110.1, 116.1, 125.8, 126.4, 134.7, 140.1, 143.8, 159.8, 160.2, 162.0, 165.9.

Example 33

Preparation of 2-[2-(N-(2-fluoroethyl)amino)pyrimidine-4-yl]-6-methoxybenzothiophene (1-33)

2-(2-Chloropyrimidine-4-yl)-6-methoxybenzothiophene (105a, 200 mg, 0.72 mmol) obtained in Preparation Example 19 and 2-fluoroethylamine-hydrochloride (FCH$_2$CH$_2$NH$_2$—HCl, 86 mg, 0.87 mmol) were dissolved in dimethylacetamide (DMA, 7 mL), and dimethylacetamide (DMA, 3 mL) containing potassium hydroxide (60 mg, 1.1 mmol) was added to the reaction mixture, followed by heating at 90° C. for 20 hours. Water was added to the reaction mixture, and organic compounds were extracted with ethyl acetate and evaporated after a treatment with sodium sulfate. Column chromatography was performed to give the target compound 2-[2-(N-(2-fluoroethyl)amino)pyrimidine-4-yl]-6-methoxybenzothiophene (1-33, 90 mg, 41%) as a yellow solid.
$^1$H NMR (400 MHz, acetone-$d_6$) δ 3.89 (s, 3H,), 4.66 (dt, J=29.2, 4.0 Hz, 2H), 4.83 (dt, J=47.6, 4.0 Hz, 2H), 7.01 (dd, J=8.8, 2.4 Hz, 1H), 7.48 (d, J=2.4 Hz, 1H), 7.53 (d, J=5.2 Hz, 1H), 7.75 (d, J=9.2 Hz, 1H), 8.12 (s, 1H), 8.52 (d, J=5.2 Hz, 1H).

Example 34

Preparation of 2-(2-methoxypyrimidine-4-yl)-6-(2-fluoroethoxy)benzothiophene (1-34)

2-(2-Chloropyrimidine-4-yl)-6-(2-fluoroethoxy)benzothiophene (105b, 80 mg, 0.26 mmol) obtained in Preparation Example 20 was dissolved in anhydrous tetrahydrofuran (4 mL). A 0.5 M sodium methoxide methanol solution (NaOMe in MeOH, 1.0 mL, 0.5 mmol) was added to the reaction mixture and stirred at room temperature for 18 hours. To the reaction mixture was added water, and organic compounds were extracted with ethyl acetate and evaporated after a treatment with sodium sulfate. Column chromatography was performed to give the target compound 2-(2-methoxypyrimidine-4-yl)-6-(2-fluoroethoxy)benzothiophene (1-34, 60 mg, 70%) as a yellow solid.
$^1$H NMR (400 MHz, acetone-$d_6$) δ 4.01 (s, 3H), 4.39 (dt, J=29.2, 4.0 Hz, 2H), 4.83 (dt, J=48.0, 4.0 Hz, 2H), 7.08 (dd, J=8.8, 2.4 Hz, 1H), 7.55 (d, J=1.6 Hz, 1H), 7.56 (d, J=5.6 Hz, 1H), 7.81 (d, J=8.8 Hz, 1H), 8.17 (s, 1H), 8.54 (d, J=5.2 Hz, 1H); $^{13}$C NMR (100 MHz, acetone-$d_6$) δ 54.9, 68.55 (d, J=19.7 Hz), 82.77 (d, J=166.7 Hz), 106.3, 110.1, 116.4, 125.8, 126.5, 135.1, 140.5, 143.7, 158.7, 160.3, 162.0, 166.5.

Example 35

Preparation of 2-[2-(N-monomethylamino)pyrimidine-4-yl]-6-(2-fluoroethoxy)benzothiophene (1-35)

2-(2-Chloropyrimidine-4-yl)-6-(2-fluoroethoxy)benzothiophene (105b, 80 mg, 0.26 mmol) obtained in Preparation Example 20 was dissolved in anhydrous tetrahydrofuran (4 mL). A 2.0 M methylamine methanol solution (NH$_2$Me in MeOH, 0.26 mL, 0.52 mmol) was added to the reaction mixture and stirred at room temperature for 3 days. To the reaction mixture was added water and organic compounds were extracted with ethyl acetate and evaporated after a treatment with sodium sulfate. Column chromatography was performed to give the target compound 2-[2-(N-monomethylamino)pyrimidine-4-yl]-6-(2-fluoroethoxy)benzothiophene (1-35, 50 mg, 63%) as a yellow solid.

$^1$H NMR (200 MHz, acetone-d$_6$) δ 3.00 (d, J=9.2 Hz, 3H), 4.39 (dt, J=28.8, 4.0 Hz, 2H), 4.82 (dt, J=48.0, 4.0 Hz, 2H), 6.32 (brs, 1H), 7.07 (dd, J=8.8, 2.2 Hz, 1H), 7.12 (d, J=5.6 Hz, 1H), 7.55 (d, J=2.4 Hz, 1H), 7.80 (d, J=8.6 Hz, 1H), 8.07 (s, 1H), 8.30 (d, J=5.2 Hz, 1H); $^{13}$C NMR (100 MHz, THF-d$_8$) δ 28.5, 68.7 (d, J=20.5 Hz), 82.3 (d, J=169.0 Hz), 105.1, 106.5, 116.2, 124.2, 126.1, 135.6, 142.7, 143.9, 158.7, 159.1, 160.5, 164.5.

Example 36

Preparation of 2-[2-(N,N-dimethylamino)pyrimidine-4-yl]-6-(2-fluoroethoxy)benzothiophene (1-36)

2-[2-(N,N-Dimethylamino)pyrimidine-4-yl]-6-(2-fluoroethoxy)benzothiophene (1-36, 77 mg, 93%) was prepared in the same manner as in Example 35 as a yellow solid using 2-(2-chloropyrimidine-4-yl)-6-(2-fluoroethoxy)benzothiophene (105b, 80 mg, 0.26 mmol) obtained in Preparation Example 20 and a 2.0 M dimethylamine methanol solution (NHMe$_2$ in MeOH, 0.26 mL, 0.52 mmol).

$^1$H NMR (400 MHz, acetone-d$_6$) δ 3.19 (s, 6H,), 4.39 (dt, J=29.2, 4.0 Hz, 2H), 4.82 (dt, J=47.6, 4.0 Hz, 2H), 6.51 (d, J=6.0 Hz, 1H), 7.06 (dd, J=8.8, 2.4 Hz, 1H), 7.52 (d, J=2.4 Hz, 1H), 7.81 (d, J=8.8 Hz, 1H), 8.12 (s, 1H), 8.19 (d, J=6.0 Hz, 1H); $^{13}$C NMR (100 MHz, acetone-d$_6$) δ 36.9, 68.54 (d, J=19.7 Hz), 82.67 (d, J=16.7 Hz), 101.5, 104.1, 106.5, 116.0, 124.2, 126.2, 135.3, 142.5, 143.4, 158.3, 158.8, 159.8.

Example 37

Preparation of 2-(2-methoxypyrimidine-4-yl)-6-(3-fluoropropoxy)benzothiophene (1-37)

2-(2-Methoxypyrimidine-4-yl)-6-(3-fluoropropoxy)benzothiophene (1-37, 75 mg, 99%) was prepared in the same manner as in Example 34 as a yellow solid using 2-(2-chloropyrimidine-4-yl)-6-(3-fluoropropoxy)benzothiophene (105c, 70 mg, 0.22 mmol) obtained in Preparation Example 21 and a 0.5 M sodium methoxide methanol solution (0.66 mL, 0.33 mmol).

$^1$H NMR (200 MHz, acetone-d$_6$) δ 2.09-2.34 (dm, J=25.6 Hz, 2H), 4.00 (s, 3H), 4.22 (t, J=6.4 Hz, 2H), 4.68 (dt, J=47.2, 6.0 Hz, 2H), 7.04 (dd, J=8.8, 2.2 Hz 1H), 7.52 (s, 1H), 7.53 (d, J=5.2 Hz, 1H), 7.78 (d, J=8.8 Hz, 1H), 8.15 (s, 1H), 8.53 (d, J=5.0 Hz, 1H); $^{13}$C NMR (50 MHz, acetone-d$_6$) δ 31.14 (d, J=13.7 Hz), 54.9, 64.93 (d, J=5.7 Hz), 81.47 (d, J=162.4 Hz), 106.4, 110.2, 116.5, 125.9, 126.6, 135.0, 140.5, 144.0, 159.2, 160.4, 162.3, 166.7.

Example 38

Preparation of 2-[2-(N-monomethylamino)pyrimidine-4-yl]-6-(3-fluoropropoxy)benzothiophene (1-38)

2-[2-(N-Monomethylamino)pyrimidine-4-yl]-6-(3-fluoropropoxy)benzothiophene (1-38, 56 mg, 81%) was prepared in the same manner as in Example 35 as a yellow solid using 2-(2-chloropyrimidine-4-yl)-6-(3-fluoropropoxy)benzothiophene (105c, 70 mg, 0.22 mmol) obtained in Preparation Example 21 and a 2.0 M methylamine methanol solution (NH$_2$Me in MeOH, 0.17 mL, 0.34 mmol).

$^1$H NMR (400 MHz, THF-d$_8$) δ 2.17 (dquintet, J=24.8, 6.0 Hz, 2H), 2.96 (s, 3H), 4.17 (t, J=6.0 Hz, 2H), 4.61 (dt, J=47.2, 6.0 Hz, 2H), 6.42 (brs, 1H), 6.98 (d, J=5.6 Hz, 1H), 6.99 (dd, J=8.0, 2.4 Hz, 1H), 7.43 (d, J=2.4 Hz, 1H), 7.68 (d, J=8.8 Hz, 1H), 7.93 (s, 1H), 8.22 (s, 1H); $^{13}$C NMR (100 MHz, THF-d$_8$) δ 28.5, 31.5 (d, J=20.5 Hz), 65.0 (d, J=6.1 Hz), 81.4 (d, J=163.8 Hz), 105.1, 106.4, 116.1, 124.2, 126.0, 135.4, 142.6, 143.9, 158.4, 158.9, 160.5, 164.5.

Example 39

Preparation of 2-[2-(N,N-dimethylamino)pyrimidine-4-yl]-6-(3-fluoropropoxy)benzothiophene (1-39)

2-[2-(N,N-Dimethylamino)pyrimidine-4-yl]-6-(3-fluoropropoxy)benzothiophene (1-39, 50 mg, 70%) was prepared in the same manner as in Example 36 as a yellow solid using 2-(2-chloropyrimidine-4-yl)-6-(3-fluoro propoxy)benzothiophene (105c, 70 mg, 0.22 mmol) obtained in Preparation Example 21 and a 2.0 M dimethylamine methanol solution (NHMe$_2$ in MeOH, 0.17 mL, 0.34 mmol).

$^1$H NMR (400 MHz, acetone-d$_6$) δ 2.16-2.25 (dm, J=25.2 Hz, 2H,), 3.21 (s, 6H), 4.21 (t, J=6.0 Hz, 2H), 4.67 (dt, J=47.2, 6.0 Hz, 2H), 7.03 (dd, J=8.8, 2.0 Hz, 1H), 7.05 (d, J=5.2 Hz, 1H), 7.51 (d, J=2.4 Hz, 1H), 7.76 (d, J=8.8 Hz, 1H), 8.03 (s, 1H), 8.32 (d, J=4.8 Hz, 1H); $^{13}$C NMR (100 MHz, acetone-d$_6$) δ 31.1 (d, J=19.7 Hz), 36.8, 64.8 (d, J=5.3 Hz), 81.4 (d, J=161.5 Hz), 101.5, 104.0, 106.3, 116.0, 124.2, 126.1, 135.0, 142.2, 143.4, 158.5, 158.8, 159.8, 162.9.

Preparation Examples 22-24

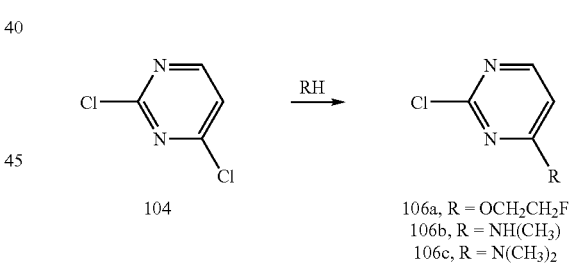

104

106a, R = OCH$_2$CH$_2$F
106b, R = NH(CH$_3$)
106c, R = N(CH$_3$)$_2$

Preparation Example 22

Preparation of 2-chloro-4-(2-fluoroethoxy)pyrimidine (106a)

2-Fluoroethanol (0.30 mL, 4.95 mmol) was added to an anhydrous tetrahydrofuran (5 mL) solution containing sodium hydride (60% NaH, 200 mg, 4.95 mmol), and an anhydrous tetrahydrofuran (5 mL) solution having 2,4-dichloropyrimidine (104, 500 mg, 3.30 mmol) dissolved therein was slowly added. The reaction mixture was stirred for 30 minutes and water was added. Organic compounds were extracted with ethyl acetate. Then, the recovered organic solution was washed with an aqueous solution of saturated sodium chloride and evaporated after a treatment with sodium sulfate. Purification was performed by column chromatograph to give 2-chloro-4-(2-fluoroethoxy)pyrimidine (106a, 237 mg, 41%) as a white solid.

$^1$H NMR (200 MHz, CDCl$_3$) δ 4.63 (dd, J=14.2, 3.2 Hz, 2H), 4.82 (dd, J=34.0, 3.2 Hz, 2H), 6.80 (d, J=6.0 Hz, 1H), 8.37 (d, J=5.8 Hz, 1H); $^{13}$C NMR (50 MHz, CDCl$_3$) δ 65.8 (d, J=19.4 Hz), 80.6 (d, J=170.0 Hz), 106.8, 158.8, 159.4, 169.4.

Preparation Example 23

Preparation of 2-chloro-4-(N-monomethylamino)pyrimidine (106b)

2,4-Dichloropyrimidine (104, 500 mg, 3.30 mmol) was dissolved in methanol (5 mL) having 2.0 M monomethylamine dissolved therein, stirred at room temperature for 3 hours. Then, the methanol solvent was removed under reduced pressure and water was added to the reaction mixture. Organic compounds were extracted with ethyl acetate and evaporated after a treatment with sodium sulfate. Purification was performed by column chromatograph to give the target compound 2-chloro-4-(N-monomethylamino)pyrimidine (106b, 128 mg, 27%) as a yellow solid.

$^1$H NMR (400 MHz, CDCl$_3$) δ 3.01 (d, J=5.2 Hz, 3H), 5.97 (brs, 1H), 6.55 (d, J=5.2, 1H), 8.16 (s, 1H); $^{13}$C NMR (100 MHz, CDCl$_3$) δ 28.3, 109.6, 159.0, 162.9.

Preparation Example 24

Preparation of 2-chloro-4-(N,N-dimethylamino)pyrimidine (106c)

2,4-dichloropyrimidine (104, 500 mg, 3.30 mmol) was dissolved in methanol (5 mL) having 2.0 M dimethylamine dissolved therein, stirred at room temperature for 3 hours. Then, the methanol solvent was removed under reduced pressure and water was added to the reaction mixture. Organic compounds were extracted with ethyl acetate, and the recovered organic solution was washed with a saturated aqueous solution of sodium chloride and evaporated after a treatment with sodium sulfate. Purification was performed by column chromatograph to give the target compound 2-chloro-4-(N,N-dimethylamino)pyrimidine (106c, 426 mg, 80%) as a white solid.

$^1$H NMR (400 MHz, CDCl$_3$) δ 3.11 (s, 6H), 6.32 (d, J=6.0 Hz, 1H), 7.99 (d, J=6.4 Hz, 1H); $^{13}$C NMR (100 MHz, CDCl$_3$) δ 37.0, 100.9, 156.3, 160.1, 162.8.

Examples 40-43

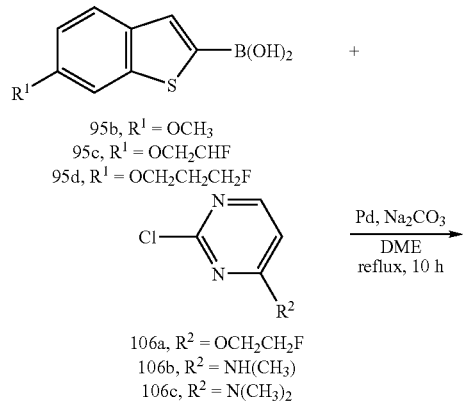

95b, R$^1$ = OCH$_3$
95c, R$^1$ = OCH$_2$CHF
95d, R$^1$ = OCH$_2$CH$_2$F

106a, R$^2$ = OCH$_2$CH$_2$F
106b, R$^2$ = NH(CH$_3$)
106c, R$^2$ = N(CH$_3$)$_2$

Pd, Na$_2$CO$_3$
DME
reflux, 10 h

-continued

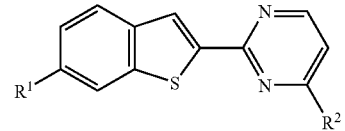

1-40, R$^1$ = OCH$_3$, R$^2$ = OCH$_2$CH$_2$F
1-41, R$^1$ = OCH$_2$CH$_2$F, R$^2$ = NH(CH$_3$)
1-42, R$^1$ = OCH$_2$CH$_2$F, R$^2$ = N(CH$_3$)$_2$
1-43, R$^1$ = OCH$_2$CH$_2$CH$_2$F, R$^2$ = NH(CH$_3$)

Example 40

Preparation of 2-[4-(2-fluoroethoxy)pyrimidine-2-yl]-6-methoxybenzothiophene (1-40)

2-[4-(2-Fluoroethoxy)pyrimidine-2-yl]-6-methoxybenzothiophene (1-40, 22 mg, 21%) was prepared in the same manner as in Example 1 as a yellow solid using 6-methoxybenzothiophene-2-boronic acid (95b, 80 mg, 0.38 mmol) obtained in Preparation Example 8 and 2-chloro-4-(2-fluoroethoxy)pyrimidine (106a, 60 mg, 0.336 mmol) obtained in Preparation Example 22.

$^1$H NMR (400 MHz, acetone-d$_6$) δ 3.91 (s, 3H,), 4.78 (dt, J=22.0, 2.4 Hz, 2H), 4.88 (dt, J=38.4, 4.4 Hz, 2H), 6.78 (d, J=5.6 Hz, 1H), 7.04 (dd, J=8.8, 2.4 Hz, 1H), 7.52 (d, J=2.0 Hz, 1H), 7.83 (d, J=8.8 Hz, 1H), 8.22 (s, 1H), 8.53 (d, J=5.6 Hz, 1H); $^{13}$C NMR (100 MHz, THF-d$_8$) δ 55.9, 67.9 (d, J=22.0 Hz), 82.4 (d, J=168.2 Hz), 105.5, 106.9, 116.1, 126.30, 126.40, 135.1, 141.6, 144.9, 159.0, 160.1, 162.2, 169.8.

Example 41

Preparation of 2-[4-(N-monomethylamino)pyrimidine-2-yl]-6-(2-fluoroethoxy)benzothiophene (1-41)

2-[4-(N-Monomethylamino)pyrimidine-2-yl]-6-(2-fluoroethoxy)benzothiophene (1-41, 60 mg, 48 mmol) was prepared in the same manner as in Example 1 as a yellow solid using 6-(2-fluoroethoxy)benzothiophene-2-boronic acid (95c, 100 mg, 0.42 mmol) obtained in Preparation Example 9 and 2-chloro-4-(N-monomethylamino)pyrimidine (106b, 46 mg, 0.32 mmol) obtained in Preparation Example 23.

$^1$H NMR (400 MHz, acetone-d$_6$) δ 3.00 (d, J=4.8 Hz, 3H), 4.39 (dt, J=29.2, 4.0 Hz, 2H), 4.82 (dt, J=47.6, 4.0 Hz, 2H), 6.33 (brs, 1H), 7.07 (dd, J=8.8, 2.4 Hz, 1H), 7.12 (d, J=5.2 Hz, 1H), 7.545 (d, J=2.4 Hz, 1H), 7.80 (d, J=8.8 Hz, 1H), 8.07 (s, 1H), 8.30 (s, 1H); $^{13}$C NMR (100 MHz, THF-d$_8$) δ 28.5, 68.8 (d, J=19.7 Hz), 82.8 (d, J=169.0 Hz), 105.1, 106.5, 116.2, 124.1, 126.1, 135.6, 142.7, 143.9, 158.7, 159.2, 160.6, 164.5.

Example 42

Preparation of 2-[4-(N,N-dimethylamino)pyrimidine-2-yl]-6-(2-fluoroethoxy)benzothiophene (1-42)

2-[4-(N,N-Dimethylamino)pyrimidine-2-yl]-6-(2-fluoroethoxy)benzothiophene (1-42, 22 mg, 29 mmol) was prepared in the same manner as in Example 1 as a yellow solid using 6-(2-fluoroethoxy)benzothiophene-2-boronic acid (95c, 100 mg, 0.42 mmol) obtained in Preparation Example 9 and 2-chloro-4-(N,N-Dimethylamino)pyrimidine (106c, 50 mg, 0.32 mmol) obtained in Preparation Example 24.

$^1$H NMR (400 MHz, acetone-d$_6$) δ 3.19 (s, 6H,), 4.39 (dt, J=29.2, 4.0 Hz, 2H), 4.82 (dt, J=47.6, 4.0 Hz, 2H), 6.51 (d, J=6.0 Hz, 1H), 7.06 (d, J=8.8, 2.4, 1H), 7.52 (d, J=2.4 Hz, 1H), 7.81 (d, J=8.8 Hz, 1H), 8.12 (s, 1H), 8.19 (d, J=6.0 Hz, 1H); $^{13}$C NMR (100 MHz, THF-d$_8$) δ 37.0, 68.7 (d, J=20.5 Hz), 82.9 (d, J=169.0 Hz), 101.4, 106.5, 115.5, 124.9, 126.0, 135.7, 144.06, 144.41, 156.4, 158.4, 161.4, 163.0.

Example 43

Preparation of 2-[4-(N-monomethylamino)pyrimidine-2-yl]-6-(3-fluoropropoxy)benzothiophene (1-43)

2-[4-(N-Monomethylamino)pyrimidine-2-yl]-6-(3-fluoropropoxy)benzothiophene (1-43, 47 mg, 61%) was prepared in the same manner as in Example 1 as a yellow solid using 6-(2-fluoropropoxy)benzothiophene-2-boronic acid (95d, 80 mg, 0.31 mmol) obtained in Preparation Example 10 and 2-chloro-4-(N-monomethylamino)pyrimidine (106b, 35 mg, 0.24 mmol) obtained in Preparation Example 23.

$^1$H NMR (400 MHz, THF-d$_8$) δ 2.17 (dq, J=25.2, 6.0 Hz, 2H), 2.96 (s, 3H), 4.17 (t, J=6.4 Hz, 2H), 4.61 (dt, J=47.2, 6.0 Hz, 2H), 6.42 (brs, 1H), 6.96 (d, J=5.2 Hz, 1H), 6.97 (dd, J=8.8, 2.4 Hz, 1H), 7.43 (d, J=2.0, 1H), 7.68 (d, J=8.8 Hz, 1H), 7.93 (s, 1H), 8.22 (s, 1H); $^{13}$C NMR (100 MHz, THF-d$_8$) δ 28.5, 31.5 (d, J=19.7 Hz), 65.0 (d, J=6.1 Hz), 81.4 (d, J=163.8 Hz), 105.1, 106.4, 116.1, 124.2, 126.0, 135.4, 142.6, 143.9, 158.4, 158.9, 161.0, 164.5.

Preparation Examples 25-30

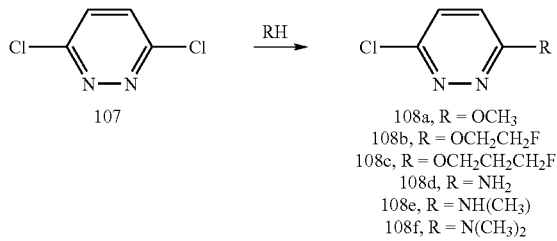

107 → 108a, R = OCH$_3$
108b, R = OCH$_2$CH$_2$F
108c, R = OCH$_2$CH$_2$CH$_2$F
108d, R = NH$_2$
108e, R = NH(CH$_3$)
108f, R = N(CH$_3$)$_2$

Preparation Example 25

Preparation of 3-methoxy-6-chloropyridazine (108a)

A 0.5 M sodium methoxide methanol solution (NaOMe in MeOH, 7.4 mL, 3.69 mmol) was slowly added to an anhydrous tetrahydrofuran (12 mL) solution having 3,6-dichloropyridazine (107, 500 mg, 3.36 mmol) dissolved therein, stirred at room temperature for one hour, followed by adding water. Organic compounds were extracted with ethyl acetate. Then, the recovered organic solution was washed with an aqueous solution of saturated sodium chloride and evaporated after a treatment with sodium sulfate. Purification was performed by column chromatograph to give the target compound 3-methoxy-6-chloropyridazine (108a, 436 mg, 90%) as a white solid.

$^1$H NMR (400 MHz, CDCl$_3$) δ 4.12 (s, 3H), 6.98 (d, J=9.2 Hz, 1H), 7.38 (d, J=9.2 Hz, 1H); $^{13}$C NMR (100 MHz, CDCl$_3$) δ 55.2, 119.9, 130.6, 150.9, 164.2.

Preparation Example 26

Preparation of 3-(2-fluoroethoxy)-6-chloropyridazine (108b)

To anhydrous tetrahydrofuran (5 mL) containing sodium hydride (NaH 60%, 121 mg, 3.02 mmol) was slowly added anhydrous tetrahydrofuran (2 mL) having 3,6-dichloropyridazine (107, 300 mg, 2.01 mmol) dissolved therein at 0° C., and added dropwise 2-fluoroethanol (194 mg, 3.02 mmol). The reaction mixture was stirred for one minutes and water was carefully added. Organic compounds were extracted with ethyl acetate, and the recovered organic solution was washed with an aqueous solution of saturated sodium chloride and evaporated after a treatment with sodium sulfate. Purification was performed by column chromatograph to give the target compound 3-(2-fluoroethoxy)-6-chloropyridazine (108b, 295 mg, 83%) as a white solid.

$^1$H NMR (400 MHz, CDCl$_3$) δ 4.73 (dm, J=12.0 Hz, 2H), 4.83 (dm, J=26.8 Hz, 2H), 7.43 (d, J=8.8 Hz, 1H), 7.06 (d, J=9.2 Hz, 1H); $^{13}$C NMR (100 MHz, CDCl$_3$) δ 66.6 (d, J=19.7 Hz), 81.3 (d, J=169.1 Hz), 120.1, 131.0, 151.3, 163.6.

Preparation Example 27

Preparation of 3-(3-fluoropropoxy)-6-chloropyridazine (108c)

3-(3-Fluoropropoxy)-6-chloropyridazine (108c, 557 mg, 87%) was prepared in the same manner as in Example 26 as a white solid using sodium hydride (NaH 60%, 202 mg, 5.04 mmol), 3,6-dichloropyridazine (107, 500 mg, 3.36 mmol) and 3-fluoro-1-propanol (393 mg, 5.04 mmol).

$^1$H NMR (400 MHz, CDCl$_3$) δ 2.23 (dm, J=25.6 Hz, 2H), 4.63 (t, J=6.0 Hz, 2H), 4.64 (dt, J=46.8, 6.0 Hz, 2H), 7.01 (d, J=9.2 Hz, 1H), 7.42 (d, J=9.2 Hz, 1H); $^{13}$C NMR (CDCl$_3$, 100 MHz) δ 29.5 (d, J=19.7 Hz), 63.4 (d, J=5.3 Hz), 80.2 (d, J=163.7 Hz), 119.8, 130.5, 150.5, 163.7.

Preparation Example 28

Preparation of 3-amino-6-chloropyridazine (108d)

3,6-Dichloropyridazine (107, 500 mg, 3.36 mmol) was slowly added to a 2.0 M ammonia methanol solution (NH$_3$ in MeOH, 17 mL, 33.6 mmol), heated at 130° C. for 96 hours and cooled to room temperature, and water was carefully added. Organic compounds were extracted with ethyl acetate, and the recovered organic solution was washed with an aqueous solution of saturated sodium chloride and evaporated after a treatment with sodium sulfate. Purification was performed by column chromatograph to give the target compound 3-amino-6-chloropyridazine (108d, 265 mg, 61%) as a white solid.

$^1$H NMR (400 MHz, CD$_3$OD) δ 6.95 (d, J=9.6 Hz, 1H), 7.34 (d, J=9.2 Hz, 1H); $^{13}$C NMR (100 MHz, CD$_3$OD) δ 119.8, 131.1, 147.1, 161.5.

Preparation Example 29

Preparation of 3-(N-monomethylamino)-6-chloropyridazine (108e)

3,6-Dichloropyridazine (107, 500 mg, 3.36 mmol) was slowly added to a 2.0 M methylamine methanol solution (NH$_2$Me in MeOH, 5 mL, 10 mmol) and stirred at room temperature for 24 hours. Water was added to the reaction mixture, and organic compounds were extracted with ethyl acetate. The recovered organic solution was washed with an aqueous solution of saturated sodium chloride and evaporated after a treatment with sodium sulfate. Purification was performed by column chromatograph to give the target compound 3-(N-monomethylamino)-6-chloropyridazine (108e, 505 mg, 88%) as a white solid.

$^1$H NMR (400 MHz, DMSO-$d_6$) δ 2.84 (d, J=4.4 Hz, 3H), 6.87 (d, J=9.2 Hz, 1H), 7.06 (brd, J=4.0 Hz, 1H), 7.33 (d, J=9.2 Hz, 1H); $^{13}$C NMR (100 MHz, DMSO-$d_6$) δ 27.9, 117.9, 128.2, 144.9, 158.6.

Preparation Example 30

Preparation of 3-(N,N-dimethylamino)-6-chloropyridazine (108f)

3-(N,N-Dimethylamino)-6-chloropyridazine (108f, 510 mg, 96%) was prepared in the same manner as in Example 29 as a white solid using 3,6-dichloropyridazine (107, 500 mg, 3.36 mmol) and a 2.0 M dimethylamine methanol solution (NHMe$_2$ in MeOH, 5 mL, 10 mmol).

$^1$H NMR (400 MHz, CDCl$_3$) δ 3.09 (s, 6H), 6.72 (d, J=9.6 Hz, 1H), 7.10 (d, J=9.6 Hz, 1H); $^{13}$C NMR (100 MHz, CDCl$_3$) δ 38.2, 113.9, 128.2, 145.3, 158.6.

Examples 44-53

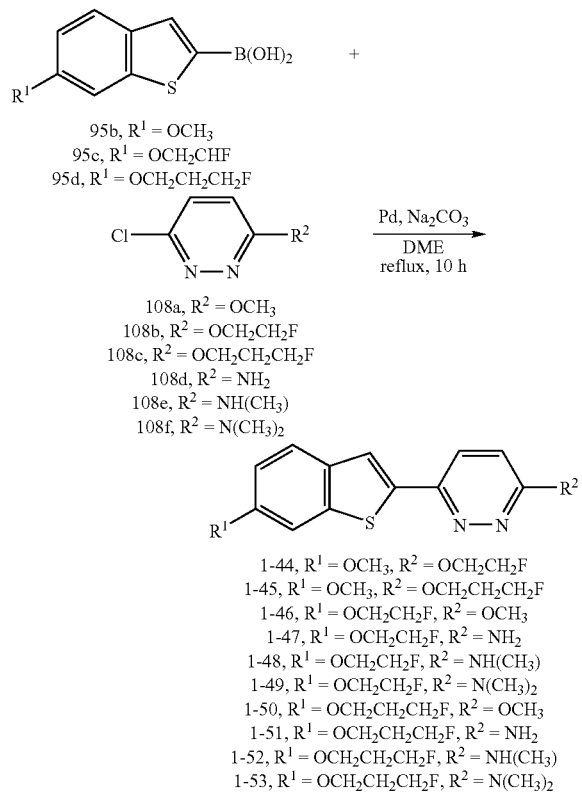

95b, R$^1$ = OCH$_3$
95c, R$^1$ = OCH$_2$CHF
95d, R$^1$ = OCH$_2$CH$_2$CH$_2$F

108a, R$^2$ = OCH$_3$
108b, R$^2$ = OCH$_2$CH$_2$F
108c, R$^2$ = OCH$_2$CH$_2$CH$_2$F
108d, R$^2$ = NH$_2$
108e, R$^2$ = NH(CH$_3$)
108f, R$^2$ = N(CH$_3$)$_2$ 1-44, R$^1$ = OCH$_3$, R$^2$ = OCH$_2$CH$_2$F
1-45, R$^1$ = OCH$_3$, R$^2$ = OCH$_2$CH$_2$CH$_2$F
1-46, R$^1$ = OCH$_2$CH$_2$F, R$^2$ = OCH$_3$
1-47, R$^1$ = OCH$_2$CH$_2$F, R$^2$ = NH$_2$
1-48, R$^1$ = OCH$_2$CH$_2$F, R$^2$ = NH(CH$_3$)
1-49, R$^1$ = OCH$_2$CH$_2$F, R$^2$ = N(CH$_3$)$_2$
1-50, R$^1$ = OCH$_2$CH$_2$CH$_2$F, R$^2$ = OCH$_3$
1-51, R$^1$ = OCH$_2$CH$_2$CH$_2$F, R$^2$ = NH$_2$
1-52, R$^1$ = OCH$_2$CH$_2$CH$_2$F, R$^2$ = NH(CH$_3$)
1-53, R$^1$ = OCH$_2$CH$_2$CH$_2$F, R$^2$ = N(CH$_3$)$_2$

Example 44

Preparation of 2-[3-(2-fluoroethoxy)pyridazine-6-yl]-6-methoxybenzothiophene (1-44)

2-[3-(2-Fluoroethoxy)pyridazine-6-yl]-6-methoxybenzothiophene (1-44, 104 mg, 98%) was prepared in the same manner as in Example 1 using 6-methoxybenzothiophene-2-boronic acid (95b, 73 mg, 0.342 mmol) obtained in Preparation Example 8 and 3-(2-fluoroethoxy)-6-chloropyridazine (108b, 74 mg, 0.419 mmol) obtained in Preparation Example 26.

$^1$H NMR (400 MHz, CDCl$_3$) δ 3.89 (s, 3H), 4.80-4.76 (m, 2H), 4.90-4.84 (m, 2H), 6.98 (dd, J=8.8, 2.4 Hz, 1H), 7.07 (d, J=9.2 Hz, 1H), 7.34 (d, J=2.4 Hz, 1H), 7.64 (s, 1H), 7.66 (d, J=8.8 Hz, 1H), 7.82 (d, J=9.2 Hz, 1H); $^{13}$C NMR (100 MHz, CDCl$_3$) δ 55.5, 66.4 (d, J=19.7 Hz), 81.6 (d, J=168.3 Hz), 104.7, 114.9, 117.7, 121.5, 124.7, 126.0, 133.8, 137.9, 142.4, 151.6, 158.2, 163.2.

Example 45

Preparation of 2-[3-(3-fluoropropoxy)pyridazine-6-yl]-6-methoxybenzothiophene (1-45)

2-[3-(2-Fluoroethoxy)pyridazine-6-yl]-6-methoxybenzothiophene (45, 80 mg, 72%) was prepared in the same manner as in Example 1 using 6-methoxybenzothiophene-2-boronic acid (95b, 73 mg, 0.342 mmol) obtained in Preparation Example 8 and 3-(3-fluoropropoxy)-6-chloropyridazine (108c, 80 mg, 0.419 mmol) obtained in Preparation Example 27.

$^1$H NMR (400 MHz, CDCl$_3$) δ 2.26 (dm, J=25.2 Hz, 2H), 3.89 (s, 3H), 4.65 (dt, J=47.2, 6.0 Hz, 2H), 4.70 (t, J=6.0 Hz, 2H), 6.98 (dd, J=8.8, 2.4 Hz, 1H), 6.99 (d, J=9.2 Hz, 1H), 7.34 (d, J=2.4 Hz, 1H), 7.63 (d, J=0.8 Hz, 1H), 7.66 (d, J=8.4 Hz, 1H), 7.79 (d, J=9.2 Hz, 1H); $^{13}$C NMR (100 MHz, CDCl$_3$) δ 30.0 (d, J=19.7 Hz), 55.6, 63.4 (d, J=5.3 Hz), 80.7 (d, J=163.8 Hz), 104.7, 114.9, 117.6, 121.3, 124.7, 125.8, 133.8, 138.1, 142.4, 151.3, 158.2, 163.5.

Example 46

Preparation of 2-(3-methoxypyridazine-6-yl)-6-(2-fluoroethoxy)benzothiophene (1-46)

2-(3-Methoxypyridazine-6-yl)-6-(2-fluoroethoxy)benzothiophene (1-46, 42 mg, 32%) was prepared in the same manner as in Example 1 using 6-(2-fluoroethoxy)benzothiophene-2-boronic acid (95c, 103 mg, 0.431 mmol) obtained in Preparation Example 9 and 3-methoxy-6-chloropyridazine (108a, 75 mg, 0.518 mmol) obtained in Preparation Example 25.

$^1$H NMR (400 MHz, CDCl$_3$) δ 4.18 (s, 3H), 4.30 (dm, J=27.6 Hz, 2H), 4.80 (dm, J=47.6 Hz, 2H), 7.01 (d, J=9.2 Hz, 1H), 7.03 (dd, J=8.8, 2.4 Hz, 1H), 7.35 (d, J=2.4 Hz, 1H), 7.65 (d, J=0.4 Hz, 1H), 7.69 (d, J=8.4 Hz, 1H), 7.80 (d, J=9.2 Hz, 1H); $^{13}$C NMR (100 MHz, CDCl$_3$) δ 55.0, 67.5 (d, J=20.5 Hz), 81.8 (d, J=169.1 Hz), 105.7, 115.3, 117.6, 121.2, 124.8, 125.7, 134.3, 138.7, 142.3, 151.2, 156.9, 164.0.

Example 47

Preparation of 2-(3-aminopyridazine-6-yl)-6-(2-fluoroethoxy)benzothiophene (1-47)

2-(3-Aminopyridazine-6-yl)-6-(2-fluoroethoxy)benzothiophene (47, 73 mg, 67%) was prepared in the same manner as in Example 1 using 6-(2-fluoroethoxy)benzothiophene-2-boronic acid (95c, 95 mg, 0.395 mmol) obtained in Preparation Example 9 and 3-amino-6-chloropyridazine (108d, 61 mg, 0.474 mmol) obtained in Preparation Example 28.

Example 48

Preparation of 2-[3-(N-monomethylamino)pyridazine-6-yl]-6-(2-fluoroethoxy)benzothiophene (1-48)

2-[3-(N-Monomethylamino)pyridazine-6-yl]-6-(2-fluoroethoxy)benzothiophene (1-48, 72 mg, 63%) was prepared in the same manner as in Example 1 using 6-(2-fluoroethoxy)benzothiophene-2-boronic acid (95c, 90 mg, 0.377 mmol) obtained in Preparation Example 9 and 3-(N-monomethylamino)-6-chloropyridazine (108e, 65 mg, 0.452 mmol) obtained in Preparation Example 29.

$^1$H NMR (400 MHz, THF-$d_8$) δ 3.02 (d, J=5.2 Hz, 3H), 4.29 (dm, J=28.4 Hz, 2H), 4.73 (dm, J=48.0 Hz, 2H), 6.26 (brd, J=4.8 Hz, 1H), 6.73 (d, J=9.2 Hz, 1H), 6.95 (dd, J=8.8, 2.4 Hz, 1H), 7.44 (d, J=2.0 Hz, 1H), 7.59 (d, J=0.8 Hz, 1H), 7.61 (d, J=8.4 Hz, 1H), 7.70 (d, J=9.2 Hz, 1H); $^{13}$C NMR (100 MHz, THF-$d_8$) δ 29.0, 68.7 (d, J=19.7 Hz), 82.9 (d, J=168.3 Hz), 106.5, 114.1, 115.6, 119.5, 124.2, 124.9, 135.8, 142.1, 142.9, 147.8, 157.9, 159.7.

Example 49

Preparation of 2-[3-(N,N-dimethylamino)pyridazine-6-yl]-6-(2-fluoroethoxy)benzothiophene (1-49)

2-(3-Dimethylaminopyridazine-6-yl)-6-(2-fluoroethoxy)benzothiophene (1-49, 45 mg, 38%) was prepared in the same manner as in Example 1 using 6-(2-fluoroethoxy)benzothiophene-2-boronic acid (95c, 90 mg, 0.373 mmol) obtained in Preparation Example 9 and 3-(N,N-dimethylamino)-6-chloro pyridazine (108f, 70 mg, 0.448 mmol) obtained in Preparation Example 30.

$^1$H NMR (400 MHz, CDCl$_3$) δ 3.20 (s, 6H), 4.28 (dm, J=27.6 Hz, 2H), 4.79 (dm, J=47.2 Hz, 2H), 6.79 (d, J=9.6 Hz, 1H), 6.99 (dd, J=8.8, 2.4 Hz, 1H), 7.33 (d, J=2.4 Hz, 1H), 7.48 (d, J=0.8 Hz, 1H), 7.59 (d, J=9.6 Hz, 1H), 7.62 (d, J=8.8 Hz, 1H); $^{13}$C NMR (100 MHz, CDCl$_3$) δ 38.1, 67.5 (d, J=20.5 Hz), 81.8 (d, J=169.8 Hz), 105.8, 111.3, 114.9, 118.8, 123.7, 124.3, 134.6, 141.7, 146.0, 156.4, 158.4.

Example 50

Preparation of 2-(3-methoxypyridazine-6-yl)-6-(3-fluoropropoxy)benzothiophene (1-50)

2-(3-Methoxypyridazine-6-yl)-6-(3-fluoropropoxy)benzothiophene (1-50, 69 mg, 75%) was prepared in the same manner as in Example 1 using 6-(3-fluoropropoxy)benzothiophene-2-boronic acid (95d, 73 mg, 0.289 mmol) obtained in Preparation Example 10 and 3-methoxy-6-chloropyridazine (108a, 50 mg, 0.347 mmol) obtained in Preparation Example 25.

$^1$H NMR (400 MHz, CDCl$_3$) δ 2.21 (dm, J=25.6 Hz, 2H), 4.16 (s, 3H), 4.18 (t, J=6.0 Hz, 2H), 4.68 (dt, J=46.8, 6.0 Hz, 2H), 6.97 (dd, J=8.8, 2.4 Hz, 1H), 6.98 (d, J=9.2 Hz, 1H), 7.34 (d, J=2.4 Hz, 1H), 7.61 (d, J=0.4 Hz, 1H), 7.65 (d, J=8.8 Hz, 1H), 7.77 (d, J=9.2 Hz, 1H); $^{13}$C NMR (100 MHz, CDCl$_3$) δ 30.4 (d, J=19.7 Hz), 63.9 (d, J=5.3 Hz), 54.9, 80.6 (d, J=163.0 Hz), 105.6, 115.0, 117.5, 121.2, 124.7, 125.7, 134.0, 138.4, 142.4, 151.2, 157.3, 163.9.

Example 51

Preparation of 2-(3-aminopyridazine-6-yl)-6-(3-fluoropropoxy)benzothiophene (1-51)

2-(3-Aminopyridazine-6-yl)-6-(3-fluoropropoxy)benzothiophene (1-51, 70 mg, 80%) was prepared in the same manner as in Example 1 using 6-(3-fluoropropoxy)benzothiophene-2-boronic acid (95d, 73 mg, 0.289 mmol) obtained in Preparation Example 10 and 3-amino-6-chloropyridazine (108d, 45 mg, 0.347 mmol) obtained in Preparation Example 28.

$^1$H NMR (400 MHz, DMSO-$d_6$) δ 2.14 (dm, J=25.6 Hz, 2H), 4.15 (t, J=6.0 Hz, 2H), 4.63 (dt, J=47.2, 6.0 Hz, 2H), 6.60 (brs, 2H), 6.85 (d, J=9.6 Hz, 1H), 6.99 (dd, J=8.8, 2.0 Hz, 1H), 7.56 (d, J=2.0 Hz, 1H), 7.70 (d, J=8.8 Hz, 1H), 7.90 (d, J=9.2 Hz, 1H), 7.79 (s, 1H); $^{13}$C NMR (100 MHz, DMSO-$d_6$) δ 29.8 (d, J=19.7 Hz), 63.9 (d, J=6.1 Hz), 80.8 (d, J=160.7 Hz), 105.9, 114.1, 114.6, 119.4, 124.29, 124.33, 133.9, 139.8, 140.7, 146.3, 156.4, 159.6.

Example 52

Preparation of 2-[3-(N-monomethylamino)pyridazine-6-yl]-6-(3-fluoropropoxy)benzothiophene (1-52)

2-[3-(N-Monomethylamino)pyridazine-6-yl]-6-(3-fluoropropoxy)benzothiophene (1-52, 53 mg, 60%) was prepared in the same manner as in Example 1 using 6-(3-fluoropropoxy)benzothiophene-2-boronic acid (95d, 90 mg, 0.354 mmol) obtained in Preparation Example 10 and 3-(N-monomethylamino)-6-chloropyridazine (108e, 61 mg, 0.428 mmol) obtained in Preparation Example 29.

$^1$H NMR (400 MHz, THF-$d_8$) δ 2.17 (dq, J=24.8, 6.0 Hz, 2H), 3.01 (d, J=4.8 Hz, 3H), 4.17 (t, J=6.4 Hz, 2H), 4.62 (dt, J=47.2, 6.0 Hz, 2H), 6.21 (brd, J=4.4 Hz, 1H), 6.71 (d, J=9.2 Hz, 1H), 6.92 (dd, J=8.8, 2.4 Hz, 1H), 7.43 (d, J=2.4 Hz, 1H), 7.58 (d, J=0.4 Hz, 1H), 7.59 (d, J=8.8 Hz, 1H), 7.69 (d, J=9.2 Hz, 1H); $^{13}$C NMR (100 MHz, THF-$d_8$) δ 29.0, 31.6 (d, J=19.7 Hz), 64.9 (d, J=5.4 Hz), 81.5 (d, J=162.9 Hz), 106.5, 113.9, 115.4, 119.5, 124.2, 124.8, 135.6, 142.0, 143.0, 147.8, 158.1, 159.7.

Example 53

Preparation of 2-[3-(N,N-dimethylamino)pyridazine-6-yl]-6-(3-fluoropropoxy)benzothiophene (1-53)

2-[3-(N,N-Dimethylamino)pyridazine-6-yl]-6-(3-fluoropropoxy)benzothiophene (1-53, 66 mg, 62%) was prepared in the same manner as in Example 1 using 6-(3-fluoropropoxy)benzothiophene-2-boronic acid (95d, 82 mg, 0.323 mmol) obtained in Preparation Example 10 and 3-(N,N-dimethylamino)-6-chloropyridazine (108f, 60 mg, 0.385 mmol) obtained in Preparation Example 30.

$^1$H NMR (400 MHz, CDCl$_3$) δ 2.20 (dm, J=26.0 Hz, 2H), 3.15 (s, 3H), 4.15 (t, J=6.0 Hz, 2H), 4.66 (dt, J=47.2, 6.0 Hz, 2H), 6.72 (d, J=9.6 Hz, 1H), 6.93 (dd, J=8.4, 2.4 Hz, 1H), 7.32 (d, J=2.4 Hz, 1H), 7.43 (d, J=0.8 Hz, 1H), 7.52 (d, J=9.6 Hz, 1H), 7.58 (d, J=8.8 Hz, 1H); $^{13}$C NMR (100 MHz, CDCl$_3$) δ

30.4 (d, J=19.8 Hz), 38.0, 63.9 (d, J=5.3 Hz), 80.6 (d, J=163.7 Hz), 105.7, 111.2, 114.6, 118.8, 123.6, 124.1, 134.3, 139.8, 141.7, 145.9, 156.7, 158.3.

Preparation Example 31

2-(2-chloropyrazine-6-yl)-6-methoxybenzothiophene (110)

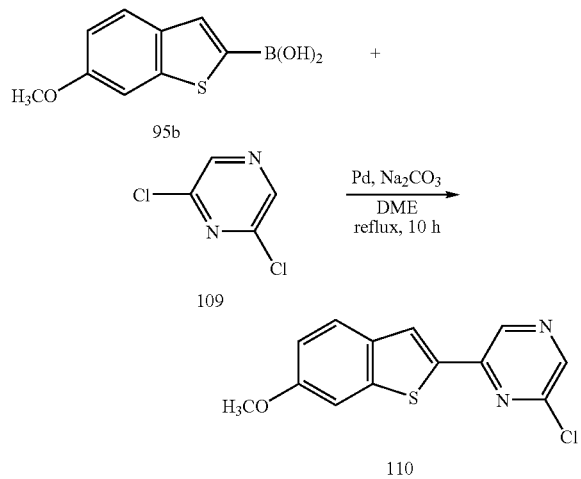

2-(2-Chloropyrazine-6-yl)-6-methoxybenzothiophene (110, 345 mg, 52%) was prepared in the same manner as in Example 1 using 6-methoxybenzothiophene-2-boronic acid (95b, 500 mg, 2.40) obtained in Preparation Example 8 and 2,6-dichloropyrazine (109, 394 mg, 2.64).

Examples 54-55

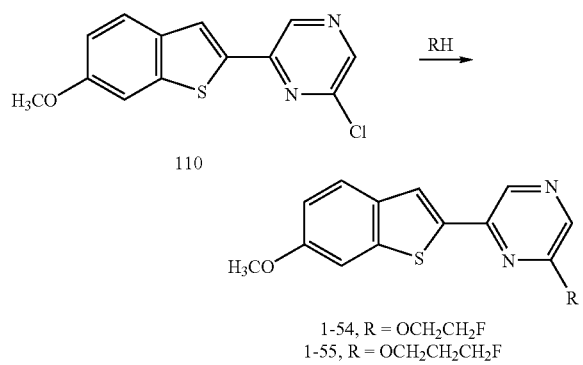

1-54, R = OCH$_2$CH$_2$F
1-55, R = OCH$_2$CH$_2$CH$_2$F

Example 54

Preparation of 2-[2-(2-fluoroethoxy)pyrazine-6-yl]-6-methoxybenzothiophene (1-54)

2-[2-(2-Fluoroethoxy)pyrazine-6-yl]-6-methoxybenzothiophene (1-54, 69 mg, 63%) was prepared in the same manner as in Example 31 using 2-(2-chloropyrazine-6-yl)-6-methoxybenzothiophene (110, 100 mg, 0.36 mmol) obtained in Preparation Example 31, sodium hydride (13 mg, 0.54 mmol) and 2-fluoroethanol (25 mg, 0.40 mmol).

$^1$H NMR (400 MHz, CDCl$_3$) δ 3.88 (s, 3H), 4.69 (dt, J=24, 4.8 Hz, 2H), 4.81 (dt, J=43.2, 4.4 Hz, 2H), 7.00 (dd, J=6.4, 2.0 Hz, 1H), 7.30 (s, 1H), 7.68 (d, J=8.8 Hz, 1H), 7.80 (s, 1H), 8.13 (s, 1H), 8.60 (s, 1H); $^{13}$C NMR (100 MHz, CDCl$_3$) δ 55.6, 65.2 (d, J=20.5 Hz), 81.5 (d, J=169.1 Hz), 104.7, 115.0, 122.0, 125.0, 132.3, 133.1, 134.1, 138.2, 142.3, 144.7, 158.2, 158.5.

Example 55

Preparation of 2-[2-(3-fluoropropoxy)pyrazine-6-yl]-6-methoxybenzothiophene (1-55)

2-[2-(3-Fluoropropoxy)pyrazine-6-yl]-6-methoxybenzothiophene (1-55, 68 mg, 59%) was prepared in the same manner as in Example 31 using 2-(2-chloropyrazine-6-yl)-6-methoxybenzothiophene (110, 100 mg, 0.36 mmol) obtained in Preparation Example 31, sodium hydride (13 mg, 0.54 mmol) and 3-fluoro-1-propanol (31 mg, 0.40 mmol).

$^1$H NMR (400 MHz, CDCl$_3$) δ 2.20-2.30 (m, 2H), 3.89 (s, 3H), 4.58 (t, J=6.4 Hz, 2H), 4.67 (dt, J=47.2, 6.4 Hz, 2H), 6.99 (dd, J=7.6, 2.4 Hz, 1H), 7.31 (s, 1H), 7.70 (d, J=8.8 Hz, 1H), 7.82 (s, 1H), 8.07 (s, 1H), 8.57 (s, 1H); $^{13}$C NMR (100 MHz, CDCl$_3$) δ 30.3 (d, J=20.5 Hz), 55.9, 62.5 (d, J=5.3 Hz), 81.0 (d, J=163 Hz), 94.6, 105.0, 115.2, 132.2, 133.3, 134.4, 138.4, 138.7, 142.6, 145.2, 158.4, 159.3.

Experimental Example

Binding Assay using β-amyloid peptide 1-1: Preparation of β-amyloid (Aβ$_{1-42}$) fibrils β-Amyloid peptide (Aβ$_{1-42}$, 1 mg, Bachem) was completely dissolved in 1 mL of DMSO, 9 mL of phosphate buffered saline (PBS) (pH 7.4) was added thereto and well mixed. The resulting mixture was incubated at 37° C. for 60 minutes to form β-amyloid fibrils, 0.5 mL was taken and transferred to each e-tube and placed into a refrigerator maintained at −80° C.

1-2: Identification of β-amyloid (Aβ$_{1-42}$) fibrils

To determine whether β-amyloid peptide was properly formed into β-amyloid fibrils, 150 μL of 5 μM Thioflavin T (ThT) was added to 50 μL of incubated β-amyloid fibrils, the fluorescence intensity of ThT binding specifically to β-amyloid fibrils at excitation/emission wavelengths ($\lambda_{ex}/\lambda_{em}$), e.g., 450 nm/480 nm, was detected using a spectrometer.

1-3: Synthesis of 2-[4-(N,N-dimethylamino)phenyl]-6-[$^{125}$I]iodobenzothiazole

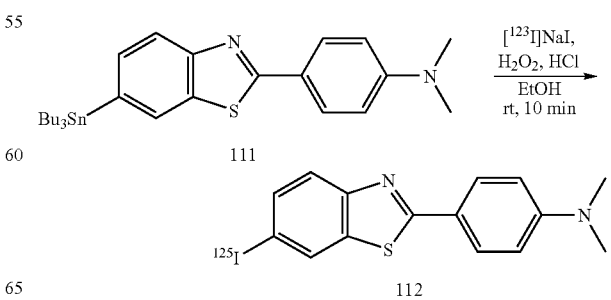

50 μL of A precursor compound (111, 1 mg) was taken from a solution having the precursor compound dissolved in 1 mL of ethanol and transferred to a test vial, and 30% hydrogen peroxide (50 μL), 1 N hydrogenchloride (50 μL) and ethanol (200 μL) were added to the resulting solution. To the mixed solution was added 1.0 mCi/100 μL of [$^{125}$I]NaI. The test vial was sealed and left undisturbed at room temperature for 10 minutes. After 10 minutes, the reaction was terminated by adding a 100 mL of saturated aqueous solution of NaHSO$_4$. The resulting product was extracted from organic layers using ethyl acetate solvent (500 μL×2), evaporated after a treatment with sodium sulfate. The organic solvent was removed from the resulting solution by blowing high purity nitrogen gas. After the organic solvent was completely removed, the resulting product was diluted with 200 μL of ethanol. The mixture was subjected to high performance liquid chromatography (HPLC) to give an I-123 labeled target compound 2-[4-(N,N-dimethylamino)phenyl]-6-[$^{125}$I]iodobenzothiazole (112, [$^{125}$I]TZDM). The final radiochemical yield was 89%.

1-4: Binding Assay 1-4-1. Dissociation Constant ($K_d$) of [$^{125}$I]TZDM (112)

β-Amyloid (Aβ$_{1-42}$) fibrils were prepared and placed into 12 mm×75 mm borosilicate test tubes at 10 nM concentrations (final), and 50 mL (0.046-5.9 pM) $^{125}$I labeled TZDM (112) was added and the test sample was dissolved in a 1 mL solution with 10% ethanol followed by incubation at room temperature for 3 hours. Following the incubation for 3 hours, the binding mixture was separated into [$^{125}$I]TZDM (112) binding to β-amyloid (Aβ$_{1-42}$) fibrils and non-binding [$^{125}$I] TZDM (112) using a cell harvester (M-24R, Brandel), and counted by a gamma counter. Then, the $K_d$ value was obtained. Here, the nonspecific binding was performed using 2 μM Thioflavin T (ThT). As a result, the dissociation constant ($K_d$) of TZDM, as determined using β-amyloid (Aβ$_{1-42}$) fibrils and [$^{125}$I]TZDM (112), was 0.13 nM.

1-4-2. Experiment of Inhibitory Binding Ratio 0.850 mL of 10% Ethanol was placed into 12 mm×75 mm borosilicate test tubes, and 50 μL of β-amyloid (Aβ$_{1-42}$) fibrils were added such that the final reaction concentration became 10 nM. Then, 50 μL of the inventive compounds (Compounds of the Examples present invention, which function as inhibitory agents were added to the test tubes such that the final reaction concentration became 1 mM. To be used as the control group, the PIB compound of Formula IV was added. To the resulting product was added 50 μL of [$^{125}$I] TZDM (112) (final concentration: 0.05 nM), followed by incubation at room temperature for 3 hours. Following the incubation for 3 hours, the binding mixture was separated into [$^{125}$I]TZDM (112) binding to β-amyloid (Aβ$_{1-42}$) fibrils and non-binding [$^{125}$I]TZDM (112) using a cell harvester, and counted by a gamma counter. Here, the nonspecific binding was performed using 2 μM Thioflavin T (ThT).

The relative binding affinity ($K_i$) values to [$^{125}$I]TZDM (112) are listed in Table 4.

TABLE 4

| | Structures of Compounds | Ki (nM) |
|---|---|---|
| Control Group | [benzothiazole structure: HO-benzothiazole-phenyl-NH-$^{11}$CH$_3$] | 0.78 |
| Example 1 | [OCH$_3$-benzothiophene-phenyl-NO$_2$] | 0.73 |
| Example 2 | [H$_3$CO-benzothiophene-phenyl-NO$_2$ (meta)] | 0.65 |
| Example 3 | [H$_3$CO-benzothiophene-phenyl-NO$_2$] | 2.30 |
| Example 4 | [HO-benzothiophene-phenyl-NO$_2$] | 1.07 |
| Example 5 | [F-CH$_2$CH$_2$-O-benzothiophene-phenyl-NO$_2$] | ND |

TABLE 4-continued
| | Structures of Compounds | Ki (nM) |
|---|---|---|
| Example 6 | 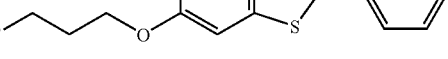 | ND |
| Example 7 | 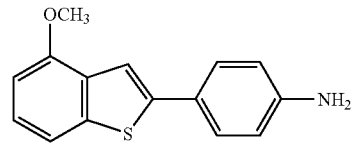 | ND |
| Example 8 | 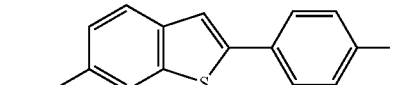 | 0.51 |
| Example 9 | 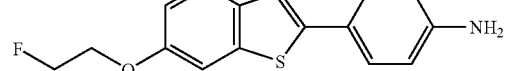 | 0.38 |
| Example 10 | 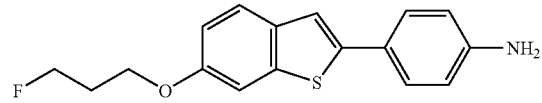 | 0.64 |
| Example 11 | 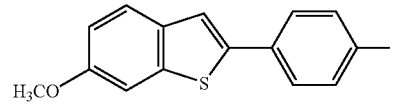 | 0.43 |
| Example 12 | 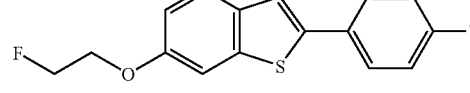 | 0.064 |
| Example 13 | 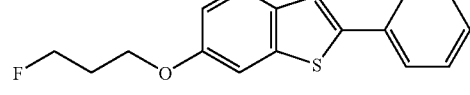 | 0.27 |
| Example 14 | 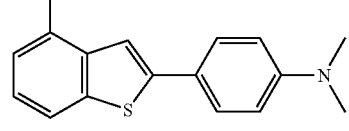 | 0.77 |
| Example 15 | 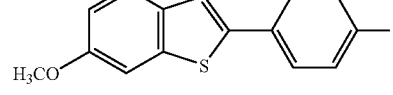 | 1.58 |
| Example 16 | 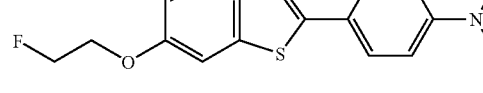 | 0.079 |
| Example 17 | 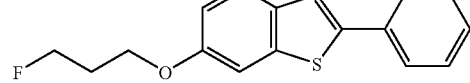 | 7.41 |

TABLE 4-continued
| | Structures of Compounds | Ki (nM) |
|---|---|---|
| Example 18 | 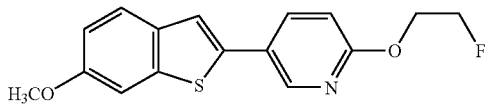 | 0.09 |
| Example 19 | 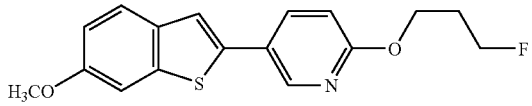 | 0.39 |
| Example 20 | 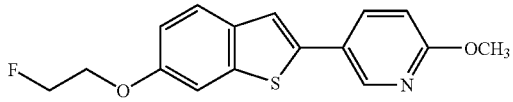 | 1.32 |
| Example 21 | 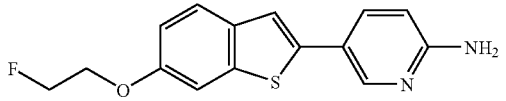 [SMILES: Nc1ccc(-c2cc3ccc(OCCF)cc3s2)cn1] | 1.11 |
| Example 22 | 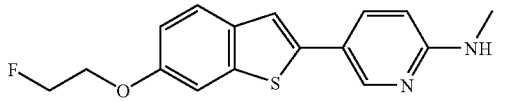 | 0.46 |
| Example 23 | 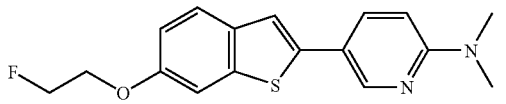 | 0.72 |
| Example 24 | 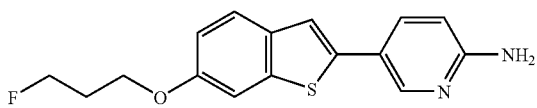 [SMILES: Nc1ccc(-c2cc3ccc(OCCCF)cc3s2)cn1] | 1.18 |
| Example 25 | 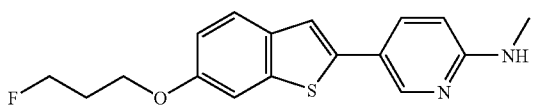 | 0.06 |
| Example 26 | 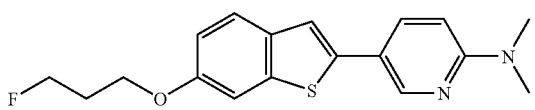 | 0.09 |
| Example 27 | 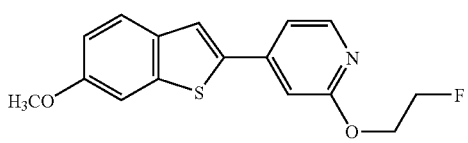 | 0.83 |
| Example 28 | 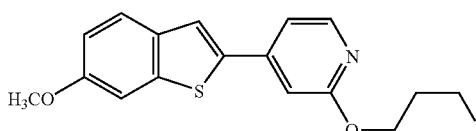 | 0.10 |
| Example 29 | 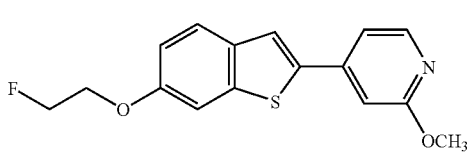 [SMILES: COc1cc(-c2cc3ccc(OCCF)cc3s2)ccn1] | ND |

TABLE 4-continued

| | Structures of Compounds | Ki (nM) |
|---|---|---|
| Example 30 | | 0.79 |
| Example 31 | | 0.61 |
| Example 32 | | 0.46 |
| Example 33 | | 0.53 |
| Example 34 | | 0.47 |
| Example 35 | | 0.55 |
| Example 36 | | ND |
| Example 37 | | 0.44 |
| Example 38 | | ND |
| Example 39 | | ND |

TABLE 4-continued

| | Structures of Compounds | Ki (nM) |
|---|---|---|
| Example 40 | 6-methoxybenzothiophene-2-yl linked to pyrimidine with 4-(2-fluoroethoxy) substituent | ND |
| Example 41 | 6-(2-fluoroethoxy)benzothiophene-2-yl linked to pyrimidine with 4-(methylamino) substituent | 0.53 |
| Example 42 | 6-(2-fluoroethoxy)benzothiophene-2-yl linked to pyrimidine with 4-(dimethylamino) substituent | 0.25 |
| Example 43 | 6-(3-fluoropropoxy)benzothiophene-2-yl linked to pyrimidine with 4-(methylamino) substituent | 0.37 |
| Example 44 | 6-methoxybenzothiophene-2-yl linked to pyridazine with 3-(2-fluoroethoxy) substituent | 0.065 |
| Example 45 | 6-methoxybenzothiophene-2-yl linked to pyridazine with 3-(3-fluoropropoxy) substituent | 1.00 |
| Example 46 | 6-(2-fluoroethoxy)benzothiophene-2-yl linked to pyridazine with 3-methoxy substituent | 0.08 |
| Example 47 | 6-(2-fluoroethoxy)benzothiophene-2-yl linked to pyridazine with 3-amino substituent | 0.44 |
| Example 48 | 6-(2-fluoroethoxy)benzothiophene-2-yl linked to pyridazine with 3-(methylamino) substituent | 0.30 |
| Example 49 | 6-(2-fluoroethoxy)benzothiophene-2-yl linked to pyridazine with 3-(dimethylamino) substituent | 0.43 |
| Example 50 | 6-(3-fluoropropoxy)benzothiophene-2-yl linked to pyridazine with 3-methoxy substituent | 0.18 |
| Example 51 | 6-(3-fluoropropoxy)benzothiophene-2-yl linked to pyridazine with 3-amino substituent | 0.38 |

TABLE 4-continued

| | Structures of Compounds | Ki (nM) |
|---|---|---|
| Example 52 | | 0.55 |
| Example 53 | | 0.65 |
| Example 54 | | ND |
| Example 55 | | 0.45 |

As listed in Table 4, the compounds according to Examples of the present invention demonstrated substantially the same or higher β-amyloid binding affinity ($K_i$) values than the PIB as the control group, i.e., 0.78 nM. In particular, compounds 1-12, 1-16, 1-25 and 1-44 had exceedingly high binding affinity ($K_i$) values that is, 0.064 nM, 0.079 nM, 0.06 nM and 0.065 nM, respectively. In addition, it was confirmed that the derivatives according to the present invention had much higher ability of binding to β-amyloid peptide so as to inhibit binding of [$^{125}$I]TZDM (112, $K_d$=0.13 nM) known to have high efficacy of binding to β-amyloid.

Examples 56-58

Synthesis of Precursor for Fluorine-18 Labeling

Example 56

2-[4-(N-methyl-N-t-butoxycarbonyl)aminophenyl]-6-(2-methanesulfonyloxyethoxy)benzothiophene (2-58)

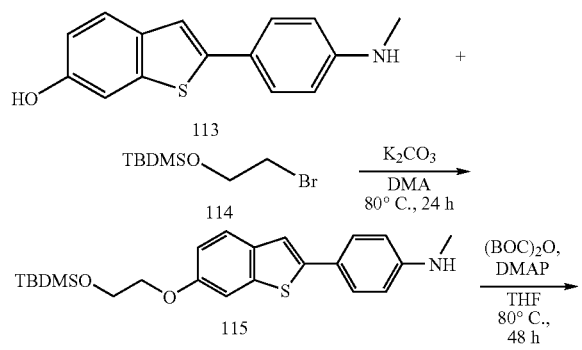

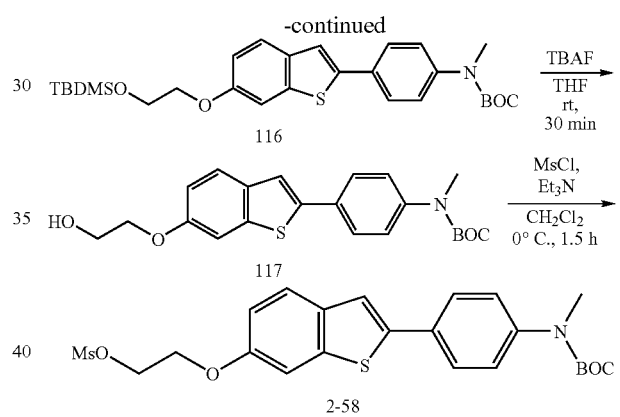

2-[4-(N-Monomethylamino)phenyl]-6-hydroxybenzothiophene (113, 1.56 g, 4.52 mmol) and potassium carbonate (1.88 g, 13.57 mmol) were dissolved in dimethylacetimide (40 mL), 1-(t-butyldimethylsilyloxy)ethyl bromide (TBDMSO-CH$_2$CH$_2$Br) (114, 1.08 g, 4.52 mmol) was added thereto, and the reaction mixture was heated at 80° C. for 24 hours. To the reaction mixture was added an aqueous solution of ammonium chloride, and organic compounds were extracted with ethyl acetate. The recovered organic solvent was washed with a brine solution and dried over sodium sulfate. Purification was performed by column chromatography to give 2-[4-(N-monomethylamino)phenyl]-6-[2-(t-butyldimethylsilyloxy)ethoxy]benzothiophene (115, 804 mg, 43%) as a yellow solid. The obtained target compound 115 had a melting point of 118-119° C., and the following physical data;

$^1$H NMR (CDCl$_3$, 200 MHz) δ 0.12 (s, 6H), 0.91 (s, 9H), 2.88 (s, 3H), 3.97-4.03 (m, 2H), 4.07-4.13 (m, 2H), 6.63 (d, J=8.8 Hz, 2H), 6.95 (dd, J=8.8, 2.2 Hz, 1H), 7.26 (s, 1H), 7.28 (d, J=2.2 Hz, 1H), 7.51 (d, J=8.8 Hz, 2H), 7.58 (d, J=8.8 Hz, 1H); $^{13}$C NMR (CDCl$_3$, 50 MHz) δ −5.2, 18.4, 25.9, 31.8, 62.1, 63.7, 105.9, 114.2, 114.6, 116.9, 123.6, 125.7, 127.3, 135.0, 140.3, 141.9, 146.9, 156.3.

2-[4-(N-Monomethylamino)phenyl]-6-[2-(t-butyldimethylsilyloxy)ethoxy]benzothiophene (115, 400 mg, 0.97 mmol) was dissolved in anhydrous tetrahydrofuran (10 mL), and (BOC)$_2$O (423 mg, 1.94 mmol) and 4-dimethylaminopyridine (DMAP, 60 mg, 0.49 mmol) were added thereto. To the reaction mixture was added one equivalent of (BOC)$_2$O (91 mg, 0.97 mmol) three times at every 12 hours with heating at 80° C. The reaction was terminated by adding water and organic compounds were extracted with ethyl acetate. The recovered organic solution was washed with a brine solution and dried over sodium sulfate. Purification was performed by column chromatography to give 2-[4-(N-methyl-N-t-butoxycarbonyl)aminophenyl]-6-[2-(t-butyldimethylsilyloxy)ethoxy]benzothiophene (116, 232 mg, 53%) as a white solid. The obtained target compound 116 had a melting point of 126-127° C., and the following physical data;

$^1$H NMR (CDCl$_3$, 200 MHz) δ 0.12 (s, 6H), 0.92 (s, 9H), 1.48 (s, 9H), 3.29 (s, 3H), 3.98-4.04 (m, 2H), 4.09-4.14 (m, 2H), 6.99 (dd, J=8.8, 2.2 Hz, 1H), 7.26-7.32 (m, 3H), 7.42 (s, 1H), 7.60-7.66 (m, 3H); $^{13}$C NMR (CDCl$_3$, 50 MHz) δ −5.2, 18.4, 25.9, 28.3, 37.1, 62.0, 69.7, 80.6, 105.8, 114.9, 118.8, 124.1, 125.6, 126.2, 131.4, 134.7, 140.8, 141.0, 143.3, 154.6, 156.7.

2-[4-(N-Methyl-N-t-butoxycarbonyl)aminophenyl]-6-[2-(t-butyldimethylsilyloxy)ethoxy]benzothiophene (116, 338 mg, 0.66 mmol) was dissolved in tetrahydrofuran (5 mL) and tetrabutylammonium fluoride (TBAF) (258 mg, 0.99 mmol) was added and stirred at room temperature for 30 minutes. Water was added to the reaction mixture and organic compounds were extracted with ethyl acetate. The recovered organic solution was washed with a brine solution and dried over sodium sulfate. Purification was performed by column chromatography to give 2-[4-(N-methyl-N-t-butoxycarbonyl)aminophenyl]-6-(2-hydroxyethoxy)benzothiophene (117, 200 mg, 90%) as a white solid. The obtained target compound 117 had a melting point of 152-153° C., and the following physical data;

$^1$H NMR (200 MHz, CDCl$_3$) δ 1.48 (s, 9H), 3.29 (s, 3H), 3.98-4.05 (m, 2H), 4.11-4.18 (m, 2H), 7.00 (dd, J=8.8, 2.0 Hz, 1H), 7.26-7.32 (m, 3H), 7.42 (s, 1H), 7.67-7.60 (m, 3H); $^{13}$C NMR (50 MHz, CDCl$_3$) δ 28.3, 37.1, 61.5, 69.6, 80.6, 105.8, 114.8, 118.8, 124.2, 125.6, 126.2, 131.3, 135.0, 140.8, 141.3, 143.4, 154.6, 156.3.

2-[4-(N-Methyl-N-t-butoxycarbonyl)aminophenyl]-6-(2-hydroxyethoxy)benzothiophene (117, 207 mg, 0.52 mmol) was dissolved in dichloromethane (5 mL), triethylamine (0.80 mL, 0.57 mmol) was added, and methanesulfonyl chloride (MsCl) (0.44 mL, 0.57 mmol) was slowly added at 0° C. After the reaction was left at 0° C. for 1.5 hours, an aqueous solution of sodium chloride was added to the reaction mixture and organic compounds were extracted with dichloromethane and dried over sodium sulfate. Purification was performed by column chromatography to give 2-[4-(N-methyl-N-t-butoxycarbonyl)aminophenyl]-6-(2-methanesulfonyloxyethoxy)benzothiophene (2-58, 209 mg, 97%) as a white solid. The obtained target compound 2-58 had a melting point of 146-147° C., and the following physical data;

$^1$H NMR (400 MHz, CDCl$_3$) δ 1.48 (s, 9H), 3.07 (s, 3H), 3.26 (s, 3H), 4.29-4.27 (m, 2H), 4.58-4.56 (m, 2H), 6.95 (dd, J=8.8, 2.4 Hz, 1H), 7.27-7.25 (m, 3H), 7.39 (s, 1H), 7.63-7.57 (m, 3H); $^{13}$C NMR (100 MHz, CDCl$_3$) δ 28.4, 37.1, 37.8, 66.3, 67.9, 80.6, 106.1, 114.5, 118.7, 124.3, 125.5, 126.2, 131.0, 135.3, 140.7, 141.6, 143.4, 154.4, 155.5.

Example 57

2-[4-(N,N-dimethylamino)phenyl]-6-(2-methanesulfonyloxyethoxy)benzothiophene (2-59)

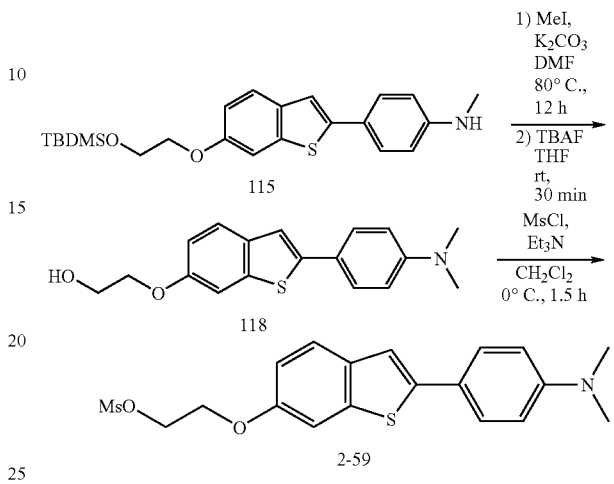

2-[4-(N-Monomethylamino)phenyl]-6-[2-(t-butyldimethylsilyloxy)ethoxy]benzothiophene (115, 150 mg, 0.36 mmol) obtained in Example 56 was dissolved in dimethylformamide (5 mL) and potassium carbonate (75 mg, 0.54 mmol) and iodomethane (0.23 mL, 0.36 mmol). The reaction mixture was stirred at 80° C. for 12 hours and an aqueous solution of sodium chloride and water were added to the reaction mixture and organic compounds were extracted with dichloromethane and extracted with ethyl acetate. The recovered organic solution was washed with a brine solution and dried over sodium sulfate to remove water and the solvent was removed under reduced pressure. The resulting mixture was dissolved in tetrahydrofuran (5 mL) and tetrabutylammonium fluoride (TBAF) (143 mg, 0.54 mmol) was added and stirred at room temperature for 30 minutes. Water was added to the reaction mixture and organic compounds were extracted with ethyl acetate. The recovered organic solution was washed with a saturated aqueous solution of sodium chloride and dried over sodium sulfate to remove water. Purification was performed by column chromatography to give 2-[4-(N,N-dimethylamino)phenyl]-6-(2-hydroxyethoxy)benzothiophene (118, 96 mg, 85%) as a white solid. The obtained target compound 118 had a melting point of 205-206° C., and the following physical data;

$^1$H NMR (200 MHz, DMSO-d$_6$) δ 2.94 (s, 6H), 3.74 (brs, 2H), 4.03 (t, J=4.8 Hz, 2H), 4.93 (brs, 1H), 6.76 (d, J=8.8 Hz, 2H), 6.96 (dd, J=8.8, 2.0 Hz, 1H), 7.48-7.54 (m, 4H), 7.62 (d, J=8.8 Hz, 1H); $^{13}$C NMR (50 MHz, DMSO-d$_6$) δ 59.6, 69.9, 105.9, 112.4, 114.6, 116.2, 121.5, 123.6, 126.6, 134.8, 139.3, 141.6, 150.1, 156.0.

2-[4-(N,N-Dimethylamino)phenyl]-6-(2-methanesulfonyloxyethoxy)benzothiophene (2-59, 86 mg, 96%) was prepared in the same manner as in Example 56 as a yellow solid using 2-[4-(N,N-dimethylamino)phenyl]-6-(2-hydroxyethoxy)benzothiophene (118, 72 mg, 0.23 mmol), triethylamine (0.39 mL, 0.28 mmol) and methanesulfonyl chloride (MsCl, 0.22 mL, 0.28 mmol). The obtained target compound 2-59 had a melting point of 193-194° C., and the following physical data;

$^1$H NMR (200 MHz, CDCl$_3$) δ 3.04 (s, 6H), 3.11 (s, 3H), 4.31-4.27 (m, 2H), 4.63-4.58 (m, 2H), 6.85 (br d, J=7.0 Hz,

2H), 6.95 (dd, J=8.8, 2.6 Hz, 1H), 7.27 (d, J=2.2 Hz, 1H), 7.31 (s, 1H), 7.55-7.63 (m, 3H); $^{13}$C NMR (50 MHz, CDCl$_3$) δ 37.8, 41.3, 66.3, 68.0, 106.2, 113.5, 114.3, 116.7, 123.9, 127.2, 135.8, 140.3, 142.6, 148.8, 155.2.

Example 58

Preparation of 2-[4-(N-methyl-N-t-butoxycarbonyl) aminophenyl]-6-(3-methanesulfonyloxypropoxy) benzothiophene (2-62)

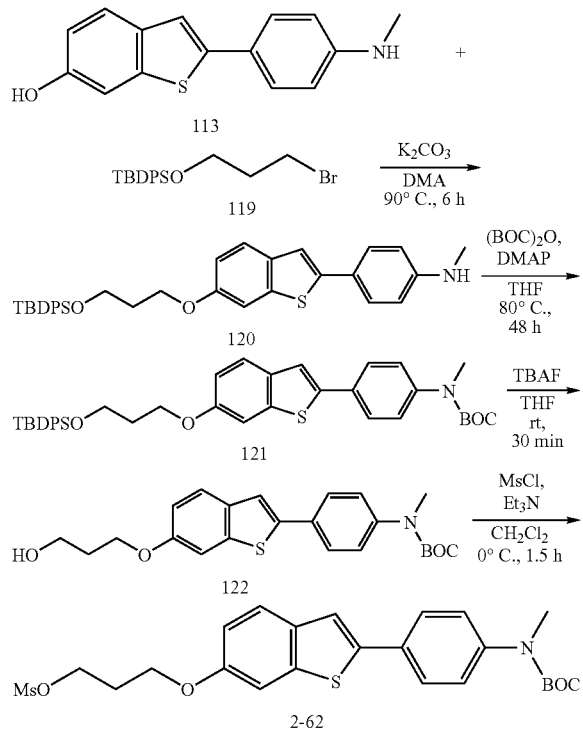

2-[4-(N-Monomethylamino)phenyl]-6-hydroxybenzothiophene (115, 150 mg, 0.59 mmol) and potassium carbonate (122 mg, 0.89 mmol) were dissolved in dimethylacetimide (10 mL), and 3-(t-butyldiphenylsilyloxy)propyl bromide (TBDMSO-CH$_2$CH$_2$CH$_2$Br) (444 mg, 1.18 mmol) was added. The reaction mixture was reacted at 90° C. for 6 hours. To the reaction mixture was added an aqueous solution of sodium chloride and organic compounds were extracted with ethyl acetate. The recovered organic solution was washed with a brine solution and dried over sodium sulfate. Purification was performed by column chromatography to give 2-[4-(N-monomethylamino)phenyl]-6-[3-(t-butyldiphenylsilyloxy)propoxy]benzothiophene (120, 225 mg, 69%) as a yellow solid.

$^1$H NMR (200 MHz, CDCl$_3$) δ 1.05 (s, 9H), 2.05 (m, 2H), 2.87 (s, 3H), 3.88 (t, J=5.8 Hz, 2H), 4.16 (t, J=6.2 Hz, 2H), 6.63 (d, J=8.6 Hz, 2H), 7.24 (dd, J=8.8, 2.2 Hz, 1H), 7.70 (m, 15H); $^{13}$C NMR (50 MHz, CDCl$_3$) δ 19.3, 27.0, 30.9, 32.4, 60.4, 65.0, 105.9, 112.8, 114.7, 116.5, 123.6, 124.1, 127.4, 127.8, 129.7, 133.9, 135.1, 135.7, 140.3, 142.5, 148.9, 156.4.

2-[4-(N-Methyl-N-t-butoxycarbonyl)aminophenyl]-6-[3-(t-butyldiphenylsilyloxy)propoxy]benzothiophene (121, 194 mg, 83%) was prepared in the same manner as in Example 56 as a yellow liquid using 2-[4-(N-monomethylamino)phenyl]-6-[3-(t-butyldiphenylsilyloxy)propoxy]benzothiophene (120, 200 mg, 0.36 mmol), (BOC)$_2$O (158 mg, 0.72 mmol) and 4-dimethylaminopyridine (DMAP, 22 mg, 0.18 mmol).

$^1$H NMR (200 MHz, CDCl$_3$) δ 1.05 (s, 9H), 1.47 (s, 9H), 2.06 (m, 2H), 3.29 (s, 3H), 3.89 (t, J=5.8 Hz, 2H), 4.17 (t, J=6.2 Hz, 2H), 6.94 (dd, J=8.8, 2.2 Hz, 1H), 7.25-7.42 (m, 10H), 7.59-7.69 (m, 7H); $^{13}$C NMR (50 MHz, CDCl$_3$) δ 19.2, 26.9, 28.3, 32.2, 37.1, 60.3, 64.9, 80.5, 105.7, 114.9, 118.9, 124.1, 125.6, 126.2, 127.6, 129.6, 131.5, 133.8, 134.7, 135.6, 140.9, 143.4, 154.6, 156.9.

2-[4-(N-Methyl-N-t-butoxycarbonyl)aminophenyl]-6-(3-hydroxypropoxy)benzothiophene (122, 90 mg, 84%) was prepared in the same manner as in Example 56 as a white solid using 2-[4-(N-methyl-N-t-butoxycarbonyl)aminophenyl]-6-[3-(t-butyldiphenylsilyloxy)propoxy]benzothiophene (121, 169 mg, 0.26 mmol) and tetrabutylammonium fluoride (TBAF) (102 mg, 0.39 mmol).

$^1$H NMR (200 MHz, CDCl$_3$) δ 1.48 (s, 9H), 2.09 (m, 2H), 3.29 (s, 3H), 3.89 (t, J=5.8 Hz, 2H), 4.19 (t, J=5.8 Hz, 2H), 6.97 (dd, J=8.8, 2.6 Hz, 1H), 7.30-7.31 (m, 2H), 7.41 (s, 1H), 7.66 (m, 3H); $^{13}$C NMR (50 MHz, CDCl$_3$) δ 28.3, 31.9, 37.1, 60.4, 66.1, 80.6, 105.7, 114.8, 118.8, 124.2, 125.6, 126.2, 131.3, 134.8, 140.8, 141.1, 143.4, 154.6, 156.5.

2-[4-(N-Methyl-N-t-butoxycarbonyl)aminophenyl]-6-(3-methanesulfonyloxypropoxy)benzothiophene (2-62, 89 mg, 99%) was prepared in the same manner as in Example 56 as a white solid using 2-[4-(N-methyl-N-t-butoxycarbonyl)aminophenyl]-6-(3-hydroxypropoxy)benzothiophene (121, 76 mg, 0.18 mmol), triethylamine (0.80 mL, 0.57 mmol) and methanesulfonyl chloride (MsCl) (0.44 mL, 0.57 mmol).

$^1$H NMR (200 MHz, CDCl$_3$) δ 1.47 (s, 9H), 2.23 (m, 2H), 2.97 (s, 3H), 3.27 (s, 3H), 4.12 (t, J=5.8 Hz, 2H), 4.44 (t, J=5.8 Hz, 2H), 6.95 (dd, J=8.8, 2.2 Hz, 1H), 7.25-7.29 (m, 3H), 7.40 (s, 1H), 7.57-7.64 (m, 3H); $^{13}$C NMR (50 MHz, CDCl$_3$) δ 28.0, 29.0, 37.0, 37.1, 63.6, 66.6, 80.4, 105.7, 114.6, 118.7, 124.1, 125.5, 126.1, 131.1, 135.0, 140.7, 141.2, 143.4, 154.4, 156.2.

Examples 59-60

Labeling with Fluorine-18

Example 59

Preparation of 2-[4-(N-monomethylamino)phenyl]-6-(2-[$^{18}$F]fluoroethoxy)naphthalene ([$^{18}$F]1-12)

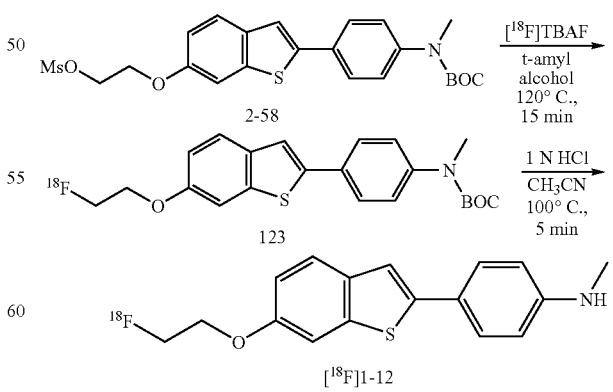

Distilled water (0.5 mL) having [$^{18}$F]fluoride (166.1 MBq) dissolved therein was placed in a reaction vessel and tetrabutylammonium bicarbonate (TBAHCO$_3$, 8 μL) was added, followed by adding an acetonitrile solution (1 mL) for azeotropical removal of residual solvent with water. Acetonitrile (1 mL) was added and heated with water until water was completely evaporated, thereby removing the solvent. After water was completely removed, methanesulfonate precursor (2-58, 2.0 mg, 4.18 mmol) obtained in Example 56 was placed in a reaction vessel and acetonitrile (0.1 mL) and t-amylalcohol (0.5 mL) were added thereto. The reaction mixture was heated at 120° C. for 15 minutes and the labeling yield was confirmed by a radio-TLC scanner. The solvent was removed by blowing nitrogen at 120° C. to afford 2-[4-(N-methyl-N-t-butoxycarbonyl)aminophenyl]-6-(2-[$^{18}$F]fluoroethoxy)naphthalene (123) in a 23% radiochemical yield.

The 2-[4-(N-methyl-N-t-butoxycarbonyl)aminophenyl]-6-(2-[$^{18}$F]fluoroethoxy)naphthalene (123) reaction mixture was dissolved in acetonitrile (0.1 mL) and a 1 N aqueous solution of hydrochloric acid (0.5 mL) was added and heated at 100° C. for 5 minutes. The reaction mixture was cooled at room temperature. The radiochemical yield of the target compound 2-[4-(N-monomethylamino)phenyl]-6-(2-[$^{18}$F]fluoroethoxy)naphthalene ([$^{18}$F]1-12) was 12%, as confirmed by radio-TLC.

Example 60

Preparation of 2-[4-(N,N-dimethylamino)phenyl]-6-(2-[$^{18}$F]fluoroethoxy)benzothiophene ([$^{18}$F]1-16)

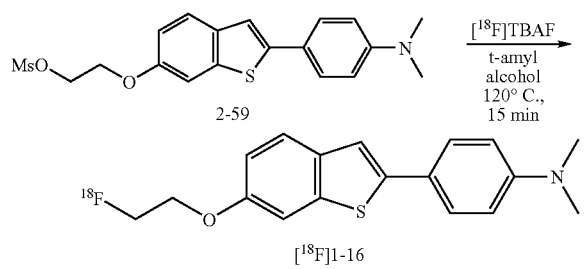

The target compound 2-[4-(N,N-dimethylamino)phenyl]-6-(2-[$^{18}$F]fluoroethoxy)benzothiophene ([$^{18}$F]1-16) was prepared in the same manner as in Example 59 using methane sulfonate precursor (2-59, 2.0 mg, 5.11 mmol) obtained in Example 57 and [$^{18}$F]fluoride (166.1 MBq) in a 11% radiochemical yield.

In another aspect, the compounds according to the present invention may be formulated in various forms according to use. Formulation methods of the aforementioned compositions as active ingredients are further illustrated by the following examples which should not be construed as constituting a limitation thereto.

Formulation Example 1

Preparation of Tablets

| 2-arylbenzothiophene derivative compound (Inventive) | 5.0 mg |
| Lactose | 14.1 mg |
| Crospovidone USNF | 0.8 mg |
| Magnesium stearic acid | 0.1 mg |

The 2-arylbenzothiophene derivative compound according to the present invention was sifted through a sieve, mixed with lactose, crospovidone USNF and magnesium stearic acid, and compressed and formulated into tablets.

Formulation Example 2

Preparation of Capsules

| 2-arylbenzothiophene derivative compound (Inventive) | 5.0 mg |
| Lactose | 14.8 mg |
| Polyvinyl pyrrolidone | 10.0 mg |
| Magnesium stearic acid | 0.2 mg |

The 2-arylbenzothiophene derivative compound according to the present invention was sifted through a sieve and mixed with lactose, polyvinyl pyrrolidone and magnesium stearic acid. The mixture was tablet-pressured according to the general capsule manufacturing method, encapsulated into a gelatin capsule and formulated into gelatin capsules.

Formulation Example 3

Preparation of Injections

| 2-arylbenzothiophene derivative compound (Inventive) | 100 mg |
| mannitol | 180 mg |
| $Na_2HPO_4 \cdot 12H_2O$ | 26 mg |
| distilled water | 2974 mg |

The 2-arylbenzothiophene derivative compound according to the present invention was dissolved in distilled water with mannitol and $Na_2HPO_4.12H_2O$, and sterilized by adjusting pH to about 7.5. Then, injections were manufactured by a conventional method.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:
1. A compound Formula 1 and pharmaceutically acceptable salts thereof:

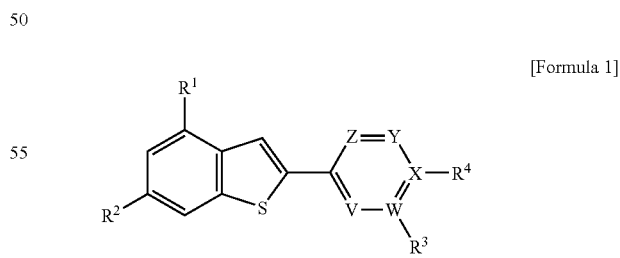

[Formula 1]

wherein:
$R^1$ is hydrogen;
$R^2$ is hydroxy, $C_1$-$C_4$ linear or branched alkoxy which is unsubstituted or substituted with hydroxy or fluorine;
$R^3$-$R^4$ are independently or optionally $C_1$-$C_4$ linear or branched alkoxy which is substituted with fluorine; nitro; amino; $C_1$-$C_4$ linear or branched alkylamino which is substituted with fluorine; or dimethylamino which is substituted with fluorine, and V, W, X, Y and Z are independently carbon or nitrogen, and at least two of V, W, X, Y and Z are nitrogen, where fluorine is in the form of $^{18}$F or $^{19}$F.

2. The compound according to claim 1, wherein R$^3$ and R$^4$ are independently or optionally C$_1$-C$_4$ linear or branched alkoxy which is substituted with fluorine; nitro; amino; C$_1$-C$_4$ linear or branched alkylamino which is substituted with fluorine.

3. The compound according to claim 1, wherein R$^3$ and R$^4$ are independently or optionally methoxy; ethoxy; fluoroethoxy; fluoropropoxy; nitro; amino; methylamino; or fluoroethylamino or fluoropropylamino.

4. The compound according to claim 1, wherein the compound is selected from the group consisting of:
(31) 2-[2-(2-fluoroethoxy)pyrimidine-4-yl]-6-methoxybenzothiophene;
(32) 2-[2-(3-fluoropropoxy)pyrimidine-4-yl]-6-methoxybenzothiophene;
(33) 2-[2-(N-(2-fluoroethyl)amino)pyrimidine-4-yl]-6-methoxybenzothiophene;
(34) 2-(2-methoxypyrimidine-4-yl)-6-(2-fluoroethoxy)benzothiophene;
(35) 2-[2-(N-monomethylamino)pyrimidine-4-yl]-6-(2-fluoroethoxy)benzothiophene;
(36) 2-[2-(N,N-dimethylamino)pyrimidine-4-yl]-6-(2-fluoroethoxy)benzothiophene;
(37) 2-(2-methoxypyrimidine-4-yl)-6-(3-fluoropropoxy)benzothiophene;
(38) 2-[2-(N-monomethylamino)pyrimidine-4-yl]-6-(3-fluoropropoxy)benzothiophene;
(39) 2-[2-(N,N-dimethylamino)pyrimidine-4-yl]-6-(3-fluoropropoxy)benzothiophene;
(40) 2-[4-(2-fluoroethoxy)pyrimidine-2-yl]-6-methoxybenzothiophene;
(41) 2-[4-(N-monomethylamino)pyrimidine-2-yl]-6-(2-fluoroethoxy)benzothiophene;
(42) 2-[4-(N,N-dimethylamino)pyrimidine-2-yl]-6-(2-fluoroethoxy)benzothiophene;
(43) 2-[4-(N-monomethylamino)pyrimidine-2-yl]-6-(3-fluoropropoxy)benzothiophene;
(44) 2-[3-(2-fluoroethoxy)pyridazine-6-yl]-6-methoxybenzothiophene;
(45) 2-[3-(3-fluoropropoxy)pyridazine-6-yl]-6-methoxybenzothiophene;
(46) 2-(3-methoxypyridazine-6-yl)-6-(2-fluoroethoxy)benzothiophene;
(47) 2-(3-aminopyridazine-6일)-6-(2-fluoroethoxy)benzothiophene;
(48) 2-[3-(N-monomethylamino)pyridazine-6-yl]-6-(2-fluoroethoxy)benzothiophene;
(49) 2-[3-(N,N-dimethylamino)pyridazine-6-yl]-6-(2-fluoroethoxy)benzothiophene;
(50) 2-(3-methoxypyridazine-6-yl)-6-(3-fluoropropoxy)benzothiophene;
(51) 2-(3-aminopyridazine-6-yl)-6-(3-fluoropropoxy)benzothiophene;
(52) 2-[3-(N-monomethylamino)pyridazine-6-yl]-6-(3-fluoropropoxy)benzothiophene;
(53) 2-[3-(N,N-dimethylamino)pyridazine-6-yl]-6-(3-fluoropropoxy)benzothiophene;
(54) 2-[2-(2-fluoroethoxy)pyrazine-6-yl]-6-methoxybenzothiophene; and
(55) 2-[2-(3-fluoropropoxy)pyrazine-6-yl]-6-methoxybenzothiophene.

5. A preparation method for compounds of Formula 1 or pharmaceutically acceptable salts thereof:

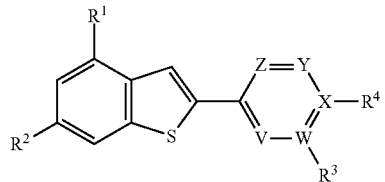

[Formula 1]

wherein

R$^1$ is hydrogen;

R$^2$ is hydroxy, C$_1$-C$_4$ linear or branched alkoxy which is unsubstituted or substituted with hydroxy or fluorine;

R$^3$-R$^4$ are independently or optionally C$_1$-C$_4$ linear or branched alkoxy which is substituted with fluorine; nitro; amino; C$_1$-C$_4$ linear or branched alkylamino which is substituted with fluorine; or dimethylamino which is substituted with fluorine, and V, W, X, Y and Z are independently carbon or nitrogen, and at least two of V, W, X, Y and Z are nitrogen, where fluorine is in the form of $^{18}$F or $^{19}$F;

the preparation method comprising, as given in the following Reaction Scheme 1:

(1) reacting a benzothiophene derivative of Formula 3 with a boron compound (iPrO)$_3$B in an organic solvent to obtain a compound of Formula 4; and (2) reacting the compound of Formula 4 with arylhalide in an organic solvent in the presence of catalyst to obtain the 2-arylbenzothiophene derivative:

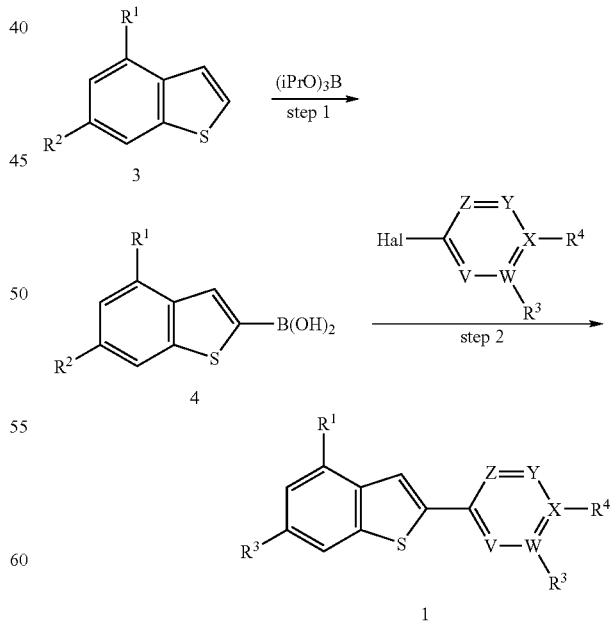

[Reaction Scheme 1]

wherein 'Hal' denotes halogen.

6. A precursor of Formula 2 for labeling the compound according to claim 1 with $^{18}$F:

[Formula 2]

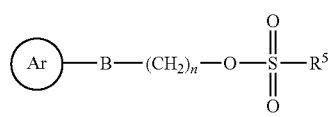

wherein

is a 2-arylbenzothiophene derivative of Formula 1:

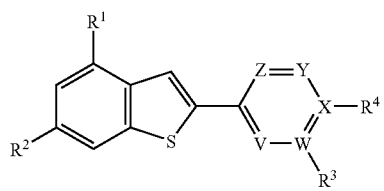

[Formula 1]

wherein

R¹ is hydrogen;

R² is hydroxy, $C_1$-$C_4$ linear or branched alkoxy which is unsubstituted or substituted with hydroxy or fluorine;

R³-R⁴ are independently or optionally $C_1$-$C_4$ linear or branched alkoxy which is substituted with fluorine; nitro; amino; $C_1$-$C_4$ linear or branched alkylamino which is substituted with fluorine; or dimethylamino which is substituted with fluorine, and V, W, X, Y and Z are independently carbon or nitrogen, and at least two of V, W, X, Y and Z are nitrogen, where fluorine is in the form of $^{18}F$ or $^{19}F$;

B is —NH— or —O—,

R⁵ is methyl, trifluoromethyl, p-toluenyl, or p-nitrophenyl, and n is 2 or 3.

7. The precursor according to claim 6, which is selected from the group consisting of:

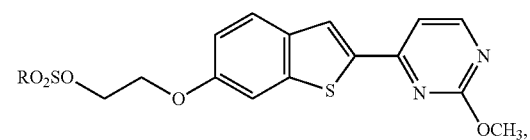

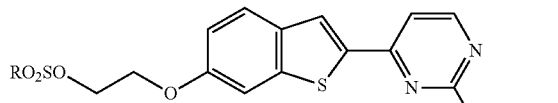

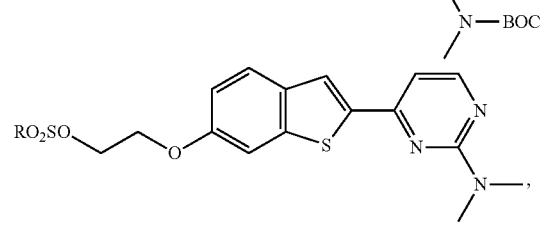

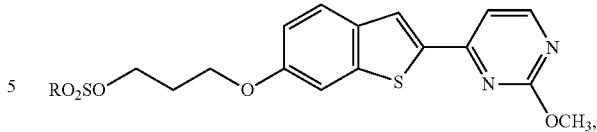

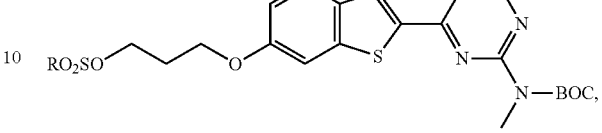

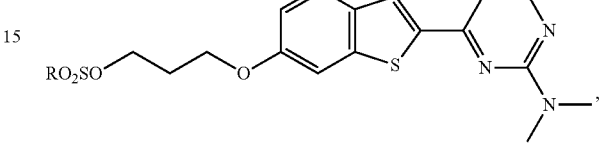

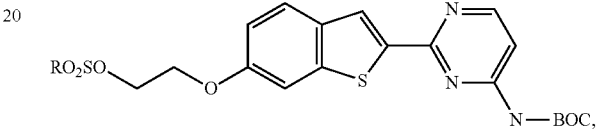

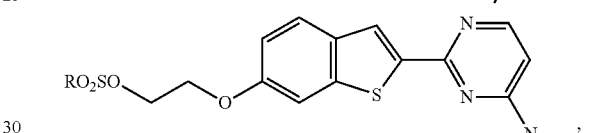

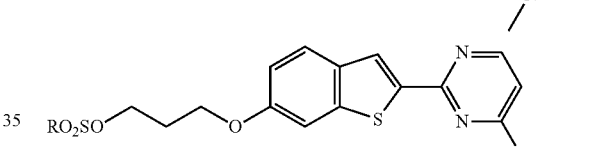

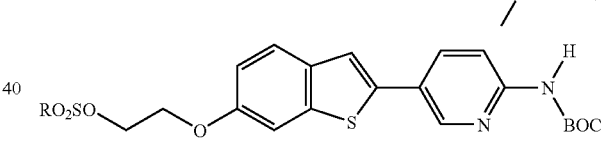

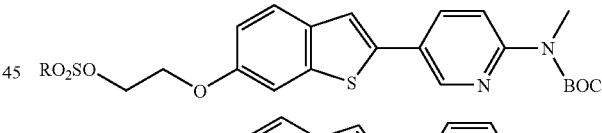

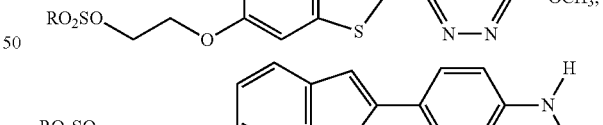

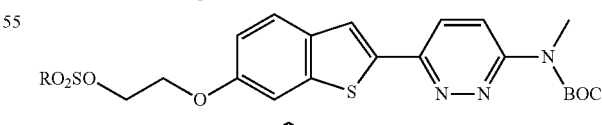

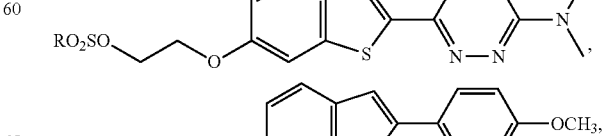

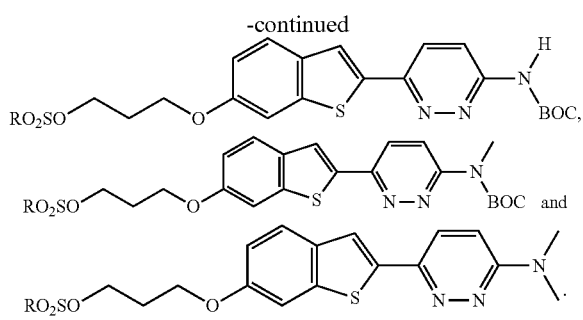

8. A preparation method of a precursor of Formula 2 for labeling the compound of Formula 1 or the pharmaceutically acceptable salt thereof with $^{18}$F, the preparation method comprising, as given in the following Reaction Scheme 2, reacting a compound of Formula 6 with $R^5SO_2Cl$ or $(R^5SO_2)O$ in an organic solvent and a base to obtain the precursor of the 2-arylbenzothiophene derivative:

[Reaction Scheme 2]

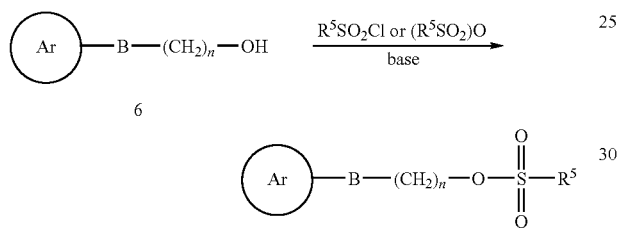

wherein

is a compound of Formula 1:

[Formula 1]

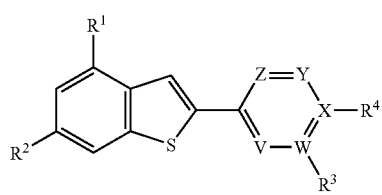

wherein
$R^1$ is hydrogen;
$R^2$ is hydroxy, $C_1$-$C_4$ linear or branched alkoxy which is unsubstituted or substituted with hydroxy or fluorine;
$R^3$-$R^4$ are independently or optionally $C_1$-$C_4$ linear or branched alkoxy which is substituted with fluorine; nitro; amino; $C_1$-$C_4$ linear or branched alkylamino which is substituted with fluorine; or dimethylamino which is substituted with fluorine, and V, W, X, Y and Z are independently carbon or nitrogen, and at least two of V, W, X, Y and Z are nitrogen, where fluorine is in the form of $^{18}$F or $^{19}$F;
B is —NH— or —O—, $R^5$ is methyl, trifluoromethyl, p-toluenyl, or p-nitrophenyl, and
n is 2 or 3.

9. A $^{18}$F labeling method comprising reacting a precursor of Formula 2 with $^{18}$F to obtain a $^{18}$F labeled compound of Formula 7 in an organic solvent, as given in the following Reaction Scheme 3:

[Reaction Scheme 3]

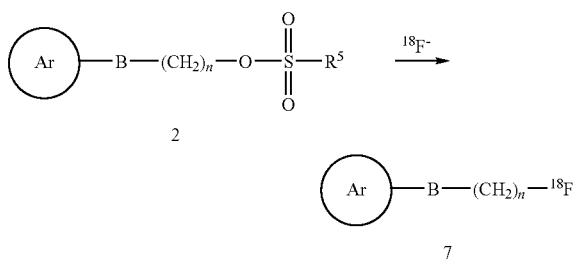

wherein is a compound of Formula 1:

[Formula 1]

wherein
$R^1$ is hydrogen;
$R^2$ is hydroxy, $C_1$-$C_4$ linear or branched alkoxy which is unsubstituted or substituted with hydroxy or fluorine;
$R^3$-$R^4$ are independently or optionally $C_1$-$C_4$ linear or branched alkoxy which is substituted with fluorine; nitro; amino; $C_1$-$C_4$ linear or branched alkylamino which is substituted with fluorine; or dimethylamino which is substituted with fluorine, and V, W, X, Y and Z are independently carbon or nitrogen, and at least two of V, W, X, Y and Z are nitrogen, where fluorine is in the form of $^{18}$F or $^{19}$F;
B is —NH— or —O—,
$R^5$ is methyl, trifluoromethyl, p-toluenyl, or p-nitrophenyl, and
n is 2 or 3.

10. A pharmaceutical composition comprising the compound of claim 1 and the pharmaceutically acceptable salts thereof as an active ingredient.

11. A radiolabeled tracer compound for Positron Emission Tomography (PET) comprising a of Formula 1 and pharmaceutically acceptable salts thereof:

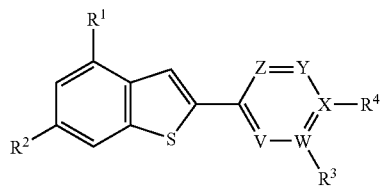

[Formula 1]

wherein:
$R^1$ is hydrogen;
$R^2$ is hydroxy, $C_1$-$C_4$ linear or branched alkoxy which is unsubstituted or substituted with hydroxy or fluorine;
$R^3$-$R^4$ are independently or optionally $C_1$-$C_4$ linear or branched alkoxy which is substituted with-fluorine; nitro; amino; $C_1$-$C_4$ linear or branched alkylamino which is with fluorine; or dimethylamino which is substituted with fluorine, and
  V, W, X, Y and Z are independently carbon or nitrogen, and at least two of V, W, X, Y and Z are nitrogen, where fluorine is in the form of $^{18}F$ or $^{19}F$,
wherein the compound binds to β-amyloid deposits in diseased brain tissue.

* * * * *